United States Patent [19]

Shiloh

[11] Patent Number: 5,858,661

[45] Date of Patent: Jan. 12, 1999

[54] ATAXIA-TELANGIECTASIA GENE AND ITS GENOMIC ORGANIZATION

[75] Inventor: Yosef Shiloh, Tel Aviv, Israel

[73] Assignee: RAMOT-University Authority for Applied Research and Industrial Development, Tel Aviv, Israel

[21] Appl. No.: 629,001

[22] Filed: Apr. 8, 1996

Related U.S. Application Data

[63] Continuation-in-part of Ser. No. 441,822, May 16, 1995, Pat. No. 5,756,288.

[51] Int. Cl.$^6$ .............................. C12Q 1/68; C07H 21/04
[52] U.S. Cl. ................................ 435/6; 536/23.5; 935/77; 935/78
[58] Field of Search .............................. 436/6, 91.2, 975; 536/23.5, 22.1, 24.3, 24.33

[56] References Cited

U.S. PATENT DOCUMENTS

| | | | |
|---|---|---|---|
| 3,791,932 | 2/1974 | Schuurs et al. | 195/103.5 R |
| 3,839,153 | 10/1974 | Schuurs et al. | 195/103.5 R |
| 3,850,578 | 11/1974 | McConnell | 424/23 |
| 3,850,752 | 11/1974 | Schuurs et al. | 195/103.5 R |
| 3,853,987 | 12/1974 | Dreyer | 424/23 |
| 3,867,517 | 2/1975 | Ling | 424/1 |
| 3,879,262 | 4/1975 | Schuurs et al. | 195/99 |
| 3,901,654 | 8/1975 | Gross | 424/23 |
| 3,935,074 | 1/1976 | Rubenstein et al. | 195/103.5 |
| 3,984,533 | 10/1976 | Uzgiris | 424/23 |
| 3,996,345 | 12/1976 | Ullman et al. | 424/23 |
| 4,034,074 | 7/1977 | Miles | 424/12 |
| 4,098,876 | 7/1978 | Piasio et al. | 424/1 |
| 4,736,866 | 4/1988 | Leder et al. | 800/1 |
| 4,879,219 | 11/1989 | Wands et al. | 435/7 |
| 5,011,771 | 4/1991 | Bellet et al. | 435/7.94 |
| 5,175,384 | 12/1992 | Krimpenfort et al. | 800/2 |
| 5,175,385 | 12/1992 | Wagner et al. | 800/2 |
| 5,217,865 | 6/1993 | Meyerowitz | 435/6 |
| 5,221,778 | 6/1993 | Byrne et al. | 800/2 |
| 5,281,521 | 1/1994 | Trojanowski et al. | 435/7.5 |
| 5,288,846 | 2/1994 | Quertermous et al. | 435/172.3 |
| 5,298,422 | 3/1994 | Schwartz et al. | 435/320.1 |
| 5,347,075 | 9/1994 | Sorge | 800/2 |
| 5,360,735 | 11/1994 | Weinshank et al. | 435/240.2 |
| 5,387,742 | 2/1995 | Cordell | 800/2 |
| 5,464,764 | 11/1995 | Capecchi et al. | 435/172.3 |
| 5,487,992 | 1/1996 | Capecchi et al. | 435/172.3 |

FOREIGN PATENT DOCUMENTS

| | | | |
|---|---|---|---|
| WO9314200 | of 1993 | WIPO | C12N 15/00 |
| WO9406908 | of 1994 | WIPO | C12N 15/00 |
| WO9423049 | of 1994 | WIPO | C12N 15/87 |
| WO9428123 | of 1994 | WIPO | C12N 15/00 |
| WO 9400572 | 1/1994 | WIPO | C12N 15/12 |
| WO 9503431 | 2/1995 | WIPO | C12Q 1/68 |

OTHER PUBLICATIONS

Kapp, "Cloning of a candidate gene for Ataxia–Telangiectasia Group D" *Am. J. Hum. Genet.*, 51:45–54 (1992).

Leonardt et al., "Nucleotide sequence analysis of a candidate gene for Ataxia–Telangiectasia Group D (ATDC)" *Genomics*, 19:130–136, (1994).

Aksentijevitch et al. "Familial mediterranean fever in Moroccan Jews: demonstration of a founder effect by extended haplotype analysis" *Am. J. Hum. Genet.*, 53:644–651 (1993).

Ambrose et al., "A physical map across chromosome 11q22–23 containing the major locus for ataxia–telangiectasia" *Genomics*, 21:612–619 (1994).

Attree et al., "The Lowe's oculocerebrorenal syndrome gene encodes a protein highly homologous to inositol . . . " *Nature*, 358:239–242 (1992).

Beamish and Lavin, "Radiosensitivity in ataxia–telangiectasia: anomalies in radiation–induced cell cycle delay" *J. Radiat. Biol.*, 65:175–184.

Berger et al., "Isolation of a candidate gene for Norrie disease by positional cloning" *Nature Genet.* 1:199–203 (1992).

Buckler et al., "Exon amplification: a strategy to isolate mammalian genes used on RNA splicing" *Proc. Natl. Acad. Sci. USA*, 88:4005–4009 (1991).

Chakravarti et al., "Nonuniform recombination within the human beta–globin gene cluster" *Am. J. Hum. Genet.*, 36:1239–1258 (1984).

Chelly et al., "Isolation of a candidate gene for Menkes disease that encodes a potential heavy metal binding protein" *Nature Genet.*, 3:14–19 (1993).

Church et al., "Isolation of genes from complex sources of mammalian genomic DNA using exon amplification" *Nature Genet.*, 6:98–104 (1993).

Collins, "Positional cloning: let's not call it reverse anymore" *Nature Genet.*, 1:3–6 (1992).

Duyk et al., "Exon trapping: a genetic screen to identify candidate transcribed sequences in cloned mammalian genomic DNA" *Proc. Natl. Acad. Sci. USA*, 87:8995–8999 (1990).

Foroud et al., "Localization of the AT locus to an 8 cM interval defined by STMY and S132" *Am. J. Hum. Genet.*, 49:1263–1279 (1991).

Frohman, *PCR Methods and Applications*, 4:S40–S58 (1994).

Frohman et al., *Proc. Natl. Sci. USA*, 85:8998–9002 (1988).

Gatti et al., "Localization of an ataxia–telangiectasia gene to chromosome 11q22–23" *Nature*, 336:557–580 (1988).

Hastbacka et al., "Linkage disequilibrium mapping in isolated founder populations: diastrophic dysplasia in Finland" *Nature Genet.*, 2:204–211 (1992).

Heim et al., "Heterozygous manifestations in four autosomal recessive human cancer–prone syndromes . . . " *Mutat. Res.*, 284:25–36 (1992).

Kastan et al., "A mammalian cell cycle checkpoint pathway utilizing p53 and GADD45 is defective in ataxia–telangiectasia" *Cell*, 71:587–597.

Kerem et al., "Identification of the cystic fibrosis gene: genetic analysis" *Science*, 245:1073–1080 (1989).

Khanna and Lavin, "Ionizing radiation and UV induction of p53 protein by different pathways in ataxia–telangiectasia cells" *Oncogene*, 8:3307–3312 (1993).

Lehesjoki et al., Localization of the EPM1 gene for progressive myoclonus epilepsy on chromosome 21: linkage disequilibrium . . . *Hum. Mol. Genet.*, 2:1229–1234 (1993).

Litt and Luty, "A hypervariable microsatellite revealed by in vitro amplification of a dinucleotide repeat within the cardiac muscle . . . " *Am. J. Hum. Genet.*, 44:397–401 (1989).

Llerena et al., "Spontaneous and induced chromosome breakage in chorionic villus samples . . . " *J. Med. Genet.*, 26:174–178 (1989).

McConville et al., *Hum. Mol. Genet.*, 2:969–974 (1993).

McConville et al., *Nucleic Acids Res.*, 18:4335–4343 (1990).

Miki et al., "A strong candidate for the breast and ovarian cancer susceptibility gene BRCA1" *Science*, 266:66–71 (1994).

Mitchison et al., "Fine genetic mapping of the Batten Disease locus (CLN3) by haplotype analysis and demonstration . . . " *Genomics*, 16:455–460 (1993).

Morgan et al., "The selective isolation of novel cDNAs encoded by the regions surrounding the human interleukin 4 and 5 genes" *Nucleic Acids Res.*, 20:5173–5179 (1992).

Oskato et al., "Ataxia–telangiectasia: allelic association with 11q22–23 markers in Moroccan–Jewish patients" *43rd Annual Meeting of the American Society of Human Genetics*, New Orleans, LA (1993).

Ozelius et al., "Strong allelic association between the torsion dystonia gene (DYT1) and loci on chromosome . . . " *Am. J. Hum. Genet.*, 50:619–628 (1992).

Parimoo et al., "cDNA selection: efficient PCR approach for the selection of cDNAs encoded in large chromosomal DNA fragments" *Proc. Natl. Acad. Sci. USA*, 88:9623–9627 (1991).

Sirugo et al., "Friedreich ataxia in Louisiana Acadians: demonstration of a founder effect by analysis . . . " *Am. J. Hum. Genet.*, 50:559–566 (1992).

Shiloh, "Ataxia–telangiectasia: closer to unraveling the mystery" *European Journal of Human Genetics* (3): 116–138 (1995).

Shiloh et al., "Carrier detection in ataxia–telangiectasia" *The Lancet*, I:689 (1986).

Swift et al., "Cancer predisposition of ataxia–telangiectasia heterozygotes" *Cancer Genet. Cytogenet.*, 46:21–27 (1990).

Swift et al., "Incidence of cancer in 1616 families affected by ataxia–telangiectasia" *New Engl. J. Med.*, 325:1831–1836 (1991).

Tagle et al., "Magnetic bead capture of expressed sequences encoded within large genomic segments" *Nature*, 361:751–753 (1993).

The European Polycystic Kidney Disease Consortium, "The polycystic kidney disease 1 gene encodes a 14 kb transcript . . . " *Cell*, 77:881–894 (1994).

The Huntington's Disease Collaborative Research Group, "A novel gene containing a trinucleotide repeat that is expanded . . . " *Cell*, 72:971–983 (1993).

Trofatter et al., "A novel moesin–, ezrin–, radixin–like gene is a candidate for the neurofibromatosis 2 tumor suppressor" *Cell*, 72:791–800 (1993).

Vanagaite et al., "Physical localization of microsatellite markers at the ataxia–telangiectasia locus at 11q22–23" *Genomics*, 22:231–233 (1994).

Vanagaite et al., "A high–density microsatellite map of the ataxia–telangiectasia locus" *Human Genetics* (in press) (1994).

Vetrie et al., "The gene involved in X–linked agammaglobulinemia is a member of the src family of protein–tyrosine kinases" *Nature*, 361:226–233 (1993).

Weber and May, "Abundant class of human DNA polymorphisms which can be typed using the polymerase chain reaction" *Am. J. Hum. Genet.*, 44:388–396 (1989).

Ziv et al., "Ataxia–telangiectasia: linkage analysis in highly inbred Arab and Druze Families and differentiation . . . " *Hum. Genet.*, 88:619–626 (1992).

Ziv et al., "The ATC (ataxia–telangiectasia complementation group C) locus localizes to 11q22–q23" *Genomics*, 9:373–375 (1991).

Porter et al., "A novel selection system for recombinational and mutational events within an intron of a eucaryotic gene" *Nucleic Acids Research*, vol. 18, No. 17, pp. 5173–5179 (1990).

Aicardi et al., "Ataxia–ocularmotor apraxia: A syndrome mimicking ataxia–telangiectasia" *Ann. Neurol.*, 24:497–502 (1988).

Ambrose et al., "Structure and expression of the Huntington's disease gene: evidence against simple inactivation . . . " *Som. Cell. Mol. Genet.*, 20:27–38 (1994).

Anderson and Kunkel, "The molecular and biochemical basis of Duchenne muscular dystrophy" *Trends Biochem. Sci.*, 17:289–292 (1992).

Ballabio et al., "Molecular heterogeneity of steroid sulfatase deficiency: a multicenter study on 57 unrelated patients . . . " *Genomics*, 4:36–40 (1989).

Barker, "A more robust, rapid alkaline denaturation sequencing method" *BioTechniques*, 14:168–169 (1993).

Barnes, "PCR amplification of up to 35–kb DNA with high fidelity and high yield from lambda bacteriophage templates" *Proc. Natl. Acad. Sci.,* 91:2216–2220 (1994).

Beaudet and Tsui, "A suggested nomeclature for designating mutations" *Hum. Mutat.,* 2:245–248 (1993).

Broughton et al., "Mutations in the xeroderma pigmentosum group D DNA repair/transcription gene in patients . . . " *Nature Genet.,* 7:189–194 (1994).

Broughton et al., "Molecular and cellular analysis of the DNA repair defect in a patient in xeroderma pigmentosum . . . " *Am. J. Hum. Genet.,* 56:167–174 (1995).

Brown et al., "Control of p70 S6 kinase by kinase activity of FRAP in vivo" *Nature,* 377:441–446 (1995).

Capecchi, "Altering the genome by homologous recombination" *Science,* 244:1288–1292 (1989).

Cheng et al., "Effective amplification in long targets from cloned inserts and human genomic DNA" *Proc. Natl. Acad. Sci.,* 91:5695–5699 (1994).

Chessa et al., "Heterogeneity in ataxia–telangiectasia: classical phenotype associated with intermediate cellular . . . " *Am. J. Med. Genet.,* 42:741–746 (1992).

Chillon et al., "Mutations in the cystic fibrosis gene in patients with gongenital absence of the vas deferens" *New Engl. J. Med.,* 332–1475–1480 (1995).

Cooper and Krawczak, in *Human Gene Mutation,* BIOS Scientific Publishers, London (1993), Chapters 8 and 10.

Davies et al., "Targeted alterations in yeast artificial chromosomes for inter–species gene transfer" *Nucleic Acids Research,* 20:2693–2698 (1992).

Derry et al., "WASP gene mutations in Wiskott–Aldrich syndrome and X–linked thrombocytopenia" *Hum. Mol. Genet.,* 4:1127–1135 (1995).

Dickinson et al., "High frequency gene targeting using insertional vectors" *Hum. Mol. Genet.,* 2:1299–1302 (1993).

Dietz and Kendzior, "Maintenance of an open reading frame as an additional level of scrutiny during splice site selection" *Nature Genet.,* 8:183–188 (1994).

Fiorilli et al., "Variant of ataxia–telangiectasia with low––level radiosensitivity" *Hum. Genet.,* 70:274–277 (1985).

Fodor et al., "Multiplexed biochemical assays with biological chips" *Nature,* 364:555–556 (1993).

Foord and Rose, "Long–distance PCR" *PCR Methods Appl.,* 3:S149–S161 (1994).

Friedman and Weitberg, "Ataxia–without telangiectasia" *Movement Disorders,* 8:223–226 (1993).

Gatti et al., "Genetic haplotyping of ataxia–telangiectasia families localizes the major gene to an 850 kb region . . . " Int. J. Radiat. Biol., (1994). 66:5247–5253.

Gibson et al., "A nonsense mutation and exon skipping in the Fanconi anaemia group C gene" *Hum. Mol. Genet.,* 2:797–799 (1993).

Gottlieb and Jackson, "Protein kinases and DNA damage" *Trends Biochem. Sci.,* 19:500–503 (1994).

Greenwell et al., "TEL1, a gene involved in controlling telomere length in *Saccharomyces cerevisiae,* is homologous . . . " *Cell,* 82:823–829 (1995).

Harding, "Clinical features and classification of inherited ataxias" *Adv. Neurol.,* 61:1–14 (1993).

Harnden, "The nature of ataxia–telangiectasia: problems and perspectives" *Int. J. Radiat. Biol.,* 66:S13–S19 (1994).

Hogervorst et al., "Rapid detection of BRCA1 mutations by the protein truncation test" Nature Genetics, 10:208–212 (1995).

Huxley et al., "The human HPRT gene on a yeast artificial chromosome is functional when transferred to mouse cells" *Genomics,* 9:742–750 (1991).

Jackson, "A reappraisal of non–consensus mRNA splice sites" *Nucleic Acids Res.,* 19:3795–3798 (1991).

Jakobovits et al., "Germ–line transmission and expression of a human–derived yeast artifical chromosome" *Nature,* 362:255–261 (1993).

James et al., "A radiation hybrid map of 506 STS markers spanning human chromosome 11" *Nature Genet.,* 8:70 (1994).

Jarvi et al., "Cystic fibrosis transmembrane conductance regulator and obstructive azoospermia" *The Lancet,* 345:1578 (1995).

Jasper et al., "Genetic complementation analysis of ataxia telangiectasia and Nijmegen breakage syndrome . . . " *Cytogenet. Cell. Genet.,* 49:259 (1988).

Kolluri et al., "Identification of WASP mutations in patients with Wiskott–Aldrich syndrome and isolated thrombocytopenia . . . " *Hum. Mol. Genet.,* 4:1119–1126 (1995).

Lamb et al., "Introduction and expression of the 400 kilobase *precursor amyloid protein* gene in transgenic mice" *Nature Genetics,* 5:22–29 (1993).

Lange et al., "Localization of an ataxia–telangiectasia gene to a 850 kb interval on chromosome . . . " *Am. J. Hum. Genet.,* s7:112–119 (1995).

Lichter et al., "High–resolution mapping of human chromosome 11 by in situ hybridization with cosmid clones" *Science,* 247:64–69 (1990).

Liu and Sommer, "Restriction endonuclease fingerprinting (REF) : a sensitive method for screening mutations . . . " *BioTechniques,* 18:470–477 (1995).

Lovett et al., "Direct selection: a method for the isolation of CDNAs encoded by large genomic regions" *Proc.Natl.Acad.Sci.USA,* 88:9628 (1991).

Maserati et al., "Ataxia–without–telangiectasia in two sisters with rearrangements of chromosomes 7 and 14" *Clin. Genet.,* 34:283–287 (1988).

McConville et al., "Genetic and physical mapping of the ataxia–telangiectasia locus on chromosome 11q22–23" *Int. J. Radiat. Biol.* vol. 66, No. 6, S45–S56 (1994).

Nehls et al. "Exon amplification from complete libraries of genomic DNA using a novel phage vector . . . " *Oncogene,* 9:2169–2175 (1994).

Nehls et al., "The sequence complexity of exons trapped from the mouse genome" *Current Biology,* 4:983–989 (1994).

Orita et al., "Detection of polymorphisms of human DNA by gel electrophoresis as single–strand conformation polymorphisms" *Proc.Natl.Acad.Sci.USA,* 86:2766–2770 (1989).

Pease et al., "Light–generated oligonucleotide arrays for rapid DNA sequence analysis" *Proc.Natl.Acad.Sci.USA,* 91(11):5022–5026 (1994).

Richard et al., "A radiation hybrid map of human chromosome 11q22–q23 containing the ataxia telangiectasia disease locus" *Genomics,* 17:1 (1993).

Roberts et al., "Exon structure of the human dystrophin gene" *Genomics,* 16:536–538 (1993).

Rothstein, "Targeting, disruption, replacement, and allele rescue . . . " in *Methods in Enzymology,* vol. 194, eds. C. Guthrie and G. Fink, Academic Press, Inc., Chap. 19, pp. 281–301 (1991).

Rotman et al., "Three dinucleotide repeat polymorphisms at the ataxia–telangiectasia locus" *Hum. Mol. Genet.,* vol. 3, No. 11, 2079 (1994).

Rotman et al., "A YAC contig spanning the ataxia–telangiectasia locus (groups A and C) on chromosome 11q22–23" *Genomics*, 24:234–242 (1994).

Rotman et al., "Physical and genetic mapping of the ATA/ATC locus in chromosome 11q22–23" *Int. J. Radiat. Biol.*, (1994). 66:5812–5821.

Rotman et al., "Rapid Identification of polymorphic CA–repeats in YAC clones" *Molecular Biotechnology*, (1995), 2:156–159.

Savitsky et al., "A single gene with homologies to phosphatidylinositol 3–kinases and rad3+ . . . " *Science*, 268:1749–1753 (Jun. 23, 1995).

Savitsky et al., "The complete sequence of the coding region of the ATM gene reveals similarity to cell cycle . . . " *Hum. Mol. Genet.*, 4:2025–2032 (1995).

Schedl et al., "A yeast artificial chromosome covering the tyrosinase gene confers copy number–dependent. . . " *Nature*, 362:258–261 (1993).

Sommer, "Recent human germ–line mutation: inferences from patients with hemophilia B" *Trends Gene*, 11:141–147 (1995).

Steingrimsdottir et al., "Mutations which alter splicing in the human hypoxanthine–guanine phosphoribosyl–transferase . . . " *Nucleic Acids Res.*, 6:1201–1208 (1992).

Strauss et al., "Germ line transmission of a yeast artificial chromosome spanning the murine . . . " *Science*, 259:1904–1907 (1993).

Taylor et al., "Genetic and cellular features of ataxia telangiectasia" *Int. J. Radiat. Biol.*, 65:65–70 (1994).

Taylor et al., "Variant forms of ataxia telangiectasia" *J. Med. Genet.*, 24:669–677 (1987).

Weemaes et al., "Nijegen breakage syndrome: a progress report" *Int. J. Radiat. Biol.*, 66:S185–S188 (1994).

Ying and Decoteau, "Cytogenetic anomalies in a patient with ataxia, immune deficiency, and high alpha–fetoprotein . . . " *Cancer Genet. Cytogenet.*, 4:311–317 (1983).

Zakian, "ATM–related genes: what do they tell us about functions of the human gene?" *Cell*, 82:685–687 (1995).

Ziv et al., "Ataxia–telangiectasia: a variant with altered in vitro phenotype of fibroblast cells" *Mutation Res.*, 210:211–219 (1989).

Rasio, et al., Genomic Organization of the ATM Locus Involved in Ataxia–Telangiectasia, Cancer Res. 55:6053–6057, Dec. 1995.

McConville et al. Am. J. Hum. Genet. (1996) 59:320–330.

Lakin et al. (1996) Oncogene 13:2707–2716.

Telatar et al. (1996) Am. J. Hum. Genet. 59:40–44.

Vorechovsky et al. Can Res. 56:2726–2732 (1996).

*Primary Examiner*—Lisa B. Arthur
*Attorney, Agent, or Firm*—Kohn & Associates

[57] ABSTRACT

A purified and isolated gene, designated ATM, mutations of which cause ataxia-telangiectasia and its genomic organization is disclosed. Methods and a kit for the detection of carriers of mutations of the ATM gene are provided by analysis of nucleic acids isolated from patients including in situ hybridization, Northern blotting and reverse transcriptase—polymerase chain reaction, Southern blotting, single strand conformational polymorphism, restriction endonuclease fingerprinting (REF), PCR amplification and DNA-chip analysis.

9 Claims, 2 Drawing Sheets

10kb

ATAXIA-TELANGIECTASIA GENE AND ITS GENOMIC ORGANIZATION

This application is a Continuation-In-Part of U.S. Ser. No. 08/441,822, filed May 16, 1995 now U.S. Pat. No. 5,756,288. +gi

GRANT SUPPORT

This work was supported in part by grants from the National Institutes of Health Institute of Neurological Disorders and Stroke (NS31763), United States-Israel Binational Science Foundation, A-T Medical Research Foundation, A-T Medical Trust, and the A-T Children's Project.

TECHNICAL FIELD

The present invention relates to the determination of the gene sequence, mutations of which cause ataxia-telangiectasia (A-T), designated ATM, and the use of the gene and gene products in detection of carriers of the A-T gene, and preparing native and transgenic organisms in which the gene products encoded by the ATM gene or its homolog in other species are artificially produced, or the expression of the native ATM gene is modified.

BACKGROUND OF THE INVENTION

Ataxia-telangiectasia (A-T) is a progressive genetic disorder affecting the central nervous and immune systems, and involving chromosomal instability, cancer predisposition, radiation sensitivity, and cell cycle abnormalities. Studies of the cellular phenotype of A-T have pointed to a defect in a putative system that processes a specific type of DNA damage and initiates a signal transduction pathway controlling cell cycle progression and repair. For a general review of Ataxia-telangiectasia, reference is hereby made to the review *Ataxia-Telangiectasis: Closer to Unraveling the Mystery*, Eur. J. Hum. Genet. (Shiloh, 1995) which, along with its cited references, is hereby incorporated by reference as well as to the reviews by Harnden (1994) and Taylor et al (1994).

Despite extensive investigation over the last two decades, A-T has remained a clinical and molecular enigma. A-T is a multi-system disease inherited in an autosomal recessive manner, with an average worldwide frequency of 1:40,000–1:100,000 live births and an estimated carrier frequency of 1% in the American population. Notable concentrations of A-T patients outside the United States are in Turkey, Italy and Israel. Israeli A-T patients are Moroccan Jews, Palestinian Arabs, Bedouins and Druzes.

Cerebellar ataxia that gradually develops into general motor dysfunction is the first clinical hallmark and results from progressive loss of Purkinje cells in the cerebellum. Oculocutaneous telangiectasia (dilation of blood vessels) develops in the bulbar conjunctiva and facial skin, and is later accompanied by graying of the hair and atrophic changes in the skin. The co-occurrence of cerebellar ataxia and telangiectases in the conjunctivae and occasionally on the facial skin—the second early hallmark of the disease—usually establishes the differential diagnosis of A-T from other cerebellar ataxias. Somatic growth is retarded in most patients, and ovarian dysgenesis is typical for female patients. Among occasional endocrine abnormalities, insulin-resistant diabetes is predominant, and serum levels of alpha-fetoprotein and carcinoembryonic antigen are elevated. The thymus is either absent or vestigial, and other immunological defects include reduced levels of serum IgA, IgE or IgG2, peripheral lymphopenia, and reduced responses to viral antigens and allogeneic cells, that cause many patients to suffer from recurrent sinopulmonary infections.

Cancer predisposition in A-T is striking: 38% of patients develop malignancies, mainly lymphoreticular neoplasms and leukemias. But, A-T patients manifest acute radiosensitivity and must be treated with reduced radiation doses, and not with radiomimetic chemotherapy. The most common cause of death in A-T, typically during the second or third decade of life, is sinopulmonary infections with or without malignancy.

The complexity of the disease is reflected also in the cellular phenotype. Chromosomal instability is expressed as increased chromosomal breakage and the appearance in lymphocytes of clonal translocations specifically involving the loci of the immune system genes. Such clones may later become predominant when a lymphoreticular malignancy appears. Primary fibroblast lines from A-T patients show accelerated senescence, increased demand for certain growth factors, and defective cytoskeletal structure. Most notable is the abnormal response of A-T cells to ionizing radiation and certain radiomimetic chemicals. While hypersensitive to the cytotoxic and clastogenic effects of these agents, DNA synthesis is inhibited by these agents to a lesser extent than in normal cells. The concomitant lack of radiation-induced cell cycle delay and reduction of radiation-induced elevation of p53 protein are evidence of defective checkpoints at the G1, S and G2 phases of the cell cycle. The G1 and G2 checkpoint defects are evident as reduced delay in cell cycle progression following treatment with ionizing radiation or radiomimetic chemicals, while the rise in the p53 protein level usually associated in normal cells with radiation-induced G1 arrest is delayed in A-T cells. The defective checkpoint at the S phase is readily observed as radioresistant DNA synthesis (RDS). Increased intrachromosomal recombination in A-T cells was also noted recently. Cellular sensitivity to DNA damaging agents and RDS are usually considered an integral part of the A-T phenotype.

Although these clinical and cellular features are considered common to all "classical" A-T patients, variations have been noted. Milder forms of the disease with later onset, slower clinical progression, reduced radiosensitivity and occasional absence of RDS have been described in several ethnic groups (Fiorilli, 1985; Taylor et al., 1987; Ziv et al., 1989; Chessa et al., 1992). Additional phenotypic variability possibly related to A-T is suggested by several disorders that show "partial A-T phenotype" with varying combinations of ataxia, immunodeficiency and chromosomal instability without telangiectases (12–16) (Ying & Decoteau, 1983; Byrne et al., 1984; Aicardi et al., 1988; Maserati et a;., 1988; Friedman & Weitberg, 1993). Still, other disorders display the A-T phenotype and additional features; most notable is the Nijmegen breakage syndrome that combines A-T features with microcephaly, sometimes with mental retardation, but without telangiectases (Weemaes et al., 1994).

Prenatal diagnoses of A-T using cytogenetic analysis or measurements of DNA synthesis have been reported, but these tests are laborious and subject to background fluctuations and, therefore, not widely used.

A-T homozygotes have two defective copies of the A-T gene and are affected with the disease. A-T heterozygotes (carriers) have one normal copy of the gene and one defective copy of the gene and are generally healthy. When two carriers have children, there is a 25% risk in every pregnancy of giving birth to an A-T affected child.

A-T heterozygotes show a significant excess of various malignancies, with a 3- to 4-fold increased risk for all cancers between the ages of 20 and 80, and a 5-fold increased risk of breast cancer in women. These observations turn A-T into a public health problem and add an important dimension to A-T research, particularly to heterozygote identification. Cultured cells from A-T heterozygotes indeed show an intermediate degree of X-ray sensitivity, but the difference from normal cells is not always large enough to warrant using this criterion as a laboratory assay for carrier detection. The main reason for the unreliability of this assay is the various degrees of overlap between A-T heterozygotes and non-heterozygotes with respect to radiosensitivity. Cytogenetic assays for carriers have the same problems as for prenatal diagnosis, they are labor intensive and not always consistent.

The nature of the protein missing in A-T is unknown. Cell fusion studies have established four complementation groups in A-T, designated A, C, D and E, suggesting the probable involvement of at least four genes or four types of mutations in one gene, with inter-allelic complementation. These four groups are clinically indistinguishable and were found to account for 55%, 28%, 14% and 3% of some 80 patients typed to date. In Israel, several Moroccan Jewish patients were assigned to group C, while Palestinian Arab patients were assigned to group A.

The general chromosomal localization of the putative A-T gene(s) has been determined, but not the sequence. An A-T locus containing the A-T(A) mutations was localized by Gatti et al. (1988) to chromosome 11, region q22-23, using linkage analysis. The A-T(C) locus was localized by applicant to the same region of chromosome 11, region q22-23, by linkage analysis of an extended Jewish Moroccan A-T family (Ziv et al., 1991). Further studies, conducted by an international consortium in which applicant participated (McConville et al., 1990; Foroud et al., 1991; Ziv et al., 1992), reconfirmed this localization in a series of studies and gradually narrowed the A-T locus to an interval estimated at 4 centimorgan, which probably contains also the A-T(E) mutations.

A proposed gene for complementation group D is disclosed in U.S. Pat. No. 5,395,767 to Murnane et al., issued Mar. 7, 1995. This sequence was found not to be mutated in any complementation group of A-T. Further, the gene sequence was mapped physically distant from the presumptive A-T locus.

Therefore, in order to better understand the nature and effects of A-T, as well as to more accurately and consistently determine those individuals who may carry the defective gene for A-T, it would be advantageous to isolate and determine the gene sequence, mutations of which are responsible for causing A-T, and utilize this sequence as a basis for detecting carriers of A-T and thereby be able to more beneficially manage the underlying conditions and predispositions of those carriers of the defective gene.

SUMMARY OF THE INVENTION AND ADVANTAGES

According to the present invention, a gene sequence and mutations of this sequence which cause ataxia-telangiectasia (A-T), designated ATM, has been purified, isolated and determined as well as mutations of the gene and the genomic organization of the gene.

The present invention further includes the method for identifying carriers of the defective A-T gene and defective A-T gene products.

The role of the ATM gene in cancer predisposition makes this gene an important target for screening. The detection of A-T mutation carriers is particularly significant in light of their radiation-sensitivity so that carrier exposure to radiation can be properly monitored and avoided.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 1A–E illustrate the positional cloning steps to identify the A-T gene(s) wherein FIG. 1A is a high-density marker map of the A-T region on chromosome 11q22-23 (Vanagaite et al., 1995), constructed by generating microsatellite markers within genomic contigs spanning the region and by physical mapping of available markers using the same contigs, the prefix "D11" has been omitted from the marker designations, FDX: the adrenal ferredoxin gene, ACAT: the acetoacetyl-coenzyme A thiolase gene, the stippled box denotes the A-T interval, defined recently by individual recombinants between the markers S1818 and S1819 in a consortium linkage study (Lange et al., 1995), the solid box indicates the two-lod confidence interval for A-T obtained in that study, between S1294 and S384;

FIG. 1B illustrates a part of a YAC contig constructed across this region (Rotman et al., 1994c);

FIG. 1C illustrates part of a cosmid contig spanning the S384–S1818 interval, generated by screening a chromosome-11 specific cosmid library with YAC clones Y16 and Y67, and subsequent contig assembly of the cosmid clones by physical mapping (Shiloh, 1995);

FIG. 1D illustrates products of gene hunting experiments wherein solid boxes denote cDNA fragments obtained by using cosmid and YAC clones for hybrid selection of cDNAs (Lovett et al. 1991; Tagle et al., 1993) from a variety of tissues, open boxes denote putative exons isolated from these cosmids by exon trapping (Church et al., 1993), these sequences hybridized back to specific cosmids (broken lines), which allowed their physical localization to specific subregions of the contig (dotted frames); and FIG. 1E illustrates a 5.9 kb cDNA clone, designated 7–9 (SEQ ID No:1), identified in a fibroblast cDNA library using the cDNA fragments and exons in 1D as a probe wherein the open box denotes an open reading frame of 5124 nucleotides, solid lines denote untranslated regions, striped arrowheads denote two Alu elements at the 3' end, and wherein dotted lines drawn between cDNA fragments and exons the cDNA indicate colinearity of sequences.

DETAILED DESCRIPTION OF THE PREFERRED EMBODIMENT

The present invention consists of a purified, isolated and cloned nucleic acid sequence encoding a gene, designated ATM, mutations in which cause ataxia-telangiectasia and genetic polymorphisms thereof. The nucleic acid can be genomic DNA, cDNA or mRNA.

The complete coding sequence of the ATM gene is set forth in SEQ ID No:2 and was submitted to the GenBank database under accession number U33841. There is extensive alternate splicing at the 5' untranslated region (5'UTR) of the ATM transcript giving rise to twelve different 5' UTRs. The sequence of the longest 5'UTR is set forth in SEQ ID No:9. The first exon in this sequence is designated 1b. There is an alternative leader exon, designated 1a (SEQ ID No:10). The sequence of the complete 3'UTR is set forth in SEQ ID No:8. Together these sequences contain the complete sequence of the ATM transcript.

As shown in Example 4, using long-distance PCR, the genomic organization, i.e. structure, of this gene was determined and the exon-intron boundaries identified. The ATM gene spans approximately 150 kb of genomic DNA and consists of 65 exons. The initiation codon falls within the fourth exon. The last exon is 3.6 kb long and contains the stop codon and a 3' untranslated region of about 3400 nucleotides.

Figure 2:
FIG. 2 is a schematic representation of the exon-intron organization of the ATM gene with vertical lines denoting the position of the ATM exons, the 3' exon and all introns are drawn to scale.

The ATM gene is composed of 65 exons (FIG. 2 and Table 1). The first two exons are alternatively spliced, and are designated 1a (SEQ ID No:10) and 1b (SEQ ID No:9). With the exception of the 3' exon, ATM exons range in size from 64 to 372 bp, with an average of 149 bp. The introns vary considerably in size, from 100 bp to about 11 kb, with the majority in the range of 1–3 kb. The consensus dinucleotides GT and AG were found at the donor and acceptor splice sites of all introns, except for a variant donor site with a GC dinucleotide (reviewed in Jackson, 1991) present in the intron 3' to exon 51. The first methionine of the open reading frame is located in exon 3, whereas the stop codon is located in the 3' and largest exon of 3.6 kb. This exon includes a 3' untranslated region (UTR) (SEQ ID No:8) of about 3400 nucleotides.

Polymorphisms are variants in the sequence generally found between different ethnic and geographic locations which, while having a different sequence, produce functionally equivalent gene products.

Current mutation data (as shown in Tables 1 and 2) indicate that A-T is a disease characterized by considerable allelic heterogeneity. Mutations imparting defects into the A-T gene can be point mutations, deletions, insertions or rearrangements. The mutations can be present within the nucleotide sequence of either/or both alleles of the ATM gene such that the resulting amino acid sequence of the ATM protein product is altered in one or both copies of the gene product; when present in both copies imparting ataxia-telangiectasia. Alternatively, a mutation event selected from the group consisting of point mutations, deletions, insertions and rearrangements could have occurred within the flanking sequences and/or regulatory sequences of ATM such that regulation of ATM is altered imparting ataxia-telangiectasia.

Table 2 illustrates several mutations in the ATM gene found in A-T patients. Mutations in the ATM gene were found in all of the complementation groups suggesting that ATM is the sole gene responsible for all A-T cases.

Table 3 illustrates the 44 mutations identified to date in applicant's patient cohort and include 34 new ones and 10 previously listed in Table 2. These mutations were found amongst 55 A-T families: many are unique to a single family, while others are shared by several families, most notably the 4 nt deletion, 7517del4, which is common to 6 A-T families from South-Central Italy. The nature and location of A-T mutations, as set forth in Table 3, provide insight into the function of the ATM protein and the molecular basis of this pleiotropic disease.

This series of 44 A-T mutations is dominated by deletions and insertions. The smaller ones, of less than 12 nt, reflect identical sequence alterations in genomic DNA. Deletions spanning larger segments of the ATM transcript were found to reflect exon skipping, not corresponding genomic deletions. Of the 44 A-T mutations identified, 39 (89%) are expected to inactivate the ATM protein by truncating it, by abolishing correct initiation or termination of translation, or by deleting large segments. Additional mutations are four smaller in-frame deletions and insertions, and one substitution of a highly conserved amino acid at the PI 3-kinase domain. The emerging profile of mutations causing A-T is thus dominated by those expected to completely inactivate the ATM protein. ATM mutations with milder effects appear to result in phenotypes related, but not identical, to A-T. In view of the pleiotropic nature of the ATM gene, the range of phenotypes associated with various ATM genotypes may be even broader, and include mild progressive conditions not always defined as clear clinical entities as discussed herein below in Example 3. Screening for mutations in this gene in such cases will reveal wider boundaries for the molecular pathology associated with the ATM gene. The present invention therefore allows the identification of these mutations in subjects with related phenotypes to A-T.

The ATM gene leaves a great deal of room for mutations: it encodes a large transcript. The variety of mutations identified in this study indeed indicates a rich mutation repertoire. Despite this wealth of mutations, their structural characteristics point to a definite bias towards those that inactivate or eliminate the ATM protein. The nature or distribution of the genomic deletions among these mutations do not suggest a special preponderance of the ATM gene for such mutations, such as that of the dystrophin (Anderson and Kunkel, 1992) or steroid sulfatase (Ballabio et al., 1989) genes which are particularly prone to such deletions. Thus, one would have expected also a strong representation of missense mutations, which usually constitute a significant portion of the molecular lesions in many disease genes (Cooper and Krawczak, 1993; Sommer, 1995). However, only one such mutation was identified in the present study. Other point mutations reflected in this series are those that probably underlie the exon skipping deletions observed in many patients, again, exerting a severe structural effect on the ATM protein.

In cloning the gene for A-T, the strategy used was a standard strategy in identifying a disease gene with an unknown protein product known as positional cloning, as is well known in the art. In positional cloning, the target gene is localized to a specific chromosomal region by establishing linkage between the disease and random genetic markers defined by DNA polymorphisms. Definition of the smallest search interval for the gene by genetic analysis is followed by long-range genomic cloning and identification of transcribed sequences within the interval. The disease gene is then identified among these sequences, mainly by searching for mutations in patients.

Several important and long sought disease genes were isolated recently in this way (Collins, 1992; Attree et al., 1992; Berger et al., 1992; Chelly et al., 1993; Vetrie et al., 1993; Trofatter et al., 1993; The Huntington's Disease Collaborative Research Group, 1993; The European Polycystic Kidney Disease Consortium, 1994; Miki et al., 1994).

Two complementary methods were used for the identification of transcribed sequences (gene hunting): hybrid selection based on direct hybridization of genomic DNA with cDNAs from various sources (Parimoo et al., 1991; Lovett et al., 1991); and exon trapping (also called exon amplification), which identifies putative exons in genomic DNA by virtue of their splicing capacity (Church et al., 1993). In hybrid selection experiments, cosmid and YAC clones served to capture cross-hybridizing sequences in cDNA collections from placenta, thymus and fetal brain, using the magnetic bead capture protocol (Morgan et al., 1992; Tagle et al., 1993). In parallel experiments, YAC clones were bound to a solid matrix and used to select cDNA fragments from a heterogeneous cDNA collection representing several human tissues (Parimoo et al., 1993). The cosmids were also used for exon trapping with the pSPL3 vector (Church et al., 1994). The captured cDNA fragments and trapped exons were mapped back to the A-T region by hybridization to several radiation hybrids containing various portions of the 11q22-23 region (Richard et al., 1993; James et al., 1994), and to high-density grids containing all the YACs and cosmids spanning this interval. An extensive transcriptional map of the A-T region was thus constructed (Shiloh et al., 1994a).

Pools of adjacent cDNA fragments and exons, expected to converge into the same transcriptional units, were used to screen cDNA libraries. A cluster of 5 cDNA fragments and 3 exons mapped in close proximity to the marker D11S535, where the location score for A-T had peaked (Lange et al., 1995). All these sequences hybridized to the same 5.9 kb of the cDNA clone, 7–9, (SEQ ID No:1) obtained from a fibroblast cDNA library.

Hybridization of the 7–9 cDNA clone to the radiation hybrid panel indicated that the entire transcript was derived from the chromosome 11 locus. The full sequence of this clone (SEQ ID No:1) was obtained using a shotgun strategy, and found to contain 5921 bp which includes an open reading frame (ORF) of 5124 nucleotides, a 538 bp 3' untranslated region (3' UTR), and a 259 bp 5' non-coding sequence containing stop codons in all reading frames. (Genbank Accession No. U26455). Two Alu repetitive elements were observed at the 3' end of this clone and in nine smaller clones representing this gene from the same cDNA library. Since no polyadenylation signal was identified in these cDNA clones, their poly(A) tracts were assumed to be associated with the Alu element rather than being authentic poly(A) tails of these transcripts. This assumption was later supported when applicants identified a cDNA clone derived from the same gene in a leukocyte cDNA library, with an alternative 3' UTR containing a typical polyadenylation signal. Alignment of the cDNA with the genomic physical map showed that the corresponding gene is transcribed from centromere to telomere.

Hybridization of a probe containing the entire ORF of clone 7–9 to northern blots from various tissues and cell lines revealed a major transcript of 12 kb, later shown to be 13 kb, in all tissues and cell types examined, and minor species of various sizes in several tissues, possibly representing alternatively spliced transcripts of the corresponding gene or other homologous sequences. Genomic sequencing later identified the 5' non-coding region of clone 7–9 as sequences of the unspliced adjacent intron. Two other cDNA clones from a leukocyte cDNA library were found to contain this intronic sequence in their 5' ends. These clones may represent splicing intermediates.

The 7–9 cDNA clone represents only part of the ATM gene transcript. Successive screening of randomly-primed cDNA libraries identified a series of partly overlapping cDNA clones and enabled the construction of a cDNA contig of about 10 Kb (Savitsky et al., 1995b). The gene coding for this transcript spans about 150 Kb of genomic DNA.

The composite cDNA of 9860 bp (GenBank Accession No. U33841; SEQ ID No:2) includes an open reading frame of 9168 nucleotides, a 538 bp 3' untranslated region (UTR), and a 164 bp 5' UTR containing stop codons in all reading frames. The sequence surrounding the first in-frame initiation codon (ACCATGA) resembles the consensus sequence proposed by Kozak for optimal initiation of translation, (A/G)CCATGG (ref. 20 in Savitsky et al, 1995b). No polyadenylation signal was found at the 3' UTR. The same poly(A) tail was found in all cDNA clones and 3' RACE products isolated to date in applicant's laboratory, however, this poly(A) tail most likely belongs to the Alu element contained in the 3' UTR.

Sequencing and PCR analysis of 32 partial ATM cDNA clones, obtained from 11 cDNA libraries representing 8 different tissues, have been colinear over the coding region, except when they contained unspliced intronic sequences. Thus, alternative splicing within the ATM coding region may not occur, or may take place at a very low frequency, or be restricted to a cell type not yet explored.

The invention further provides a purified protein (SEQ ID No:3) as encoded by the ATM gene and analogs and mutations thereof (SEQ ID No:2). The present invention further provides for mutations in SEQ ID No:3 which cause ataxia-telangiectasia, for example, as set forth in Tables 2 and 3.

This product of the ATM Open Reading Frame (SEQ ID No:2) is a large protein of 3056 amino acids, with an expected molecular weight of 350.6 kDa. The ATM gene product (SEQ ID No:3) contains a PI-3 kinase signature at codons 2855–2875, and a potential leucine zipper at codons 1217–1238. The presence of this leucine zipper may suggest possible dimerization of the ATM protein or interaction with additional proteins. No nuclear localization signal, transmembrane domains or other motifs were observed in this protein sequence.

The ATM gene product is a member of a family of large proteins that share a highly conserved carboxy-terminal region of about 300 amino acids showing high sequence homology to the catalytic domain of PI-3 kinases. Among these proteins are Tel1p and Mec1p in budding yeast, rad3p in fission yeast, the TOR proteins in yeast and their mammalian counterpart, FRAP (RAFT1), MEI-41 in *Drosophila melanogaster*, and the catalytic subunit of DNA-dependent protein kinase (DNA-PKcs) in mammals. All of these proteins are implicated in cell cycle control and some of them, like Mec1p, rad3p and DNA-PKcs are involved in response to DNA damage. (Table 1 in Savitsky et al 1995b). The central core of the PI-3 kinase-like domain contains two subdomains with highly conserved residues present in nearly all kinases, including protein and PI-3 kinases. The residues Asp and Asn (at positions 2870 and 2875 in ATM), and the triplet Asp-Phe-Gly (at positions 2889–2891), which represents the most highly conserved short stretch in the protein kinase catalytic domain, have been implicated in the binding of ATP and phosphotransferase activity. Mutations in the genes encoding these proteins result in a variety of phenotypes that share features with A-T, such as radiosensitivity, chromosomal instability, telomere shortening, and defective cell cycle checkpoints (reviewed by Savitsky et al., 1995a and b; Zakian, 1995).

A possible working model for the ATM protein's function is DNA-PK, a serine/threonine protein kinase that is activated in vitro by DNA double-strand breaks and responds by phosphorylating several regulatory proteins (Gottlieb and Jackson, 1994). The ATM protein may be responsible for conveying a signal evoked by a specific DNA damage to various checkpoint systems, possibly via lipid or protein phosphorylation.

The present invention further includes a recombinant protein encoded by SEQ ID No:2 or SEQ ID No:3. This recombinant protein is isolated and purified by techniques known to those skilled in the art.

An analog will be generally at least 70% homologous over any portion that is functionally relevant. In more preferred embodiments, the homology will be at least 80% and can approach 95% homology to the ATM protein. The amino acid sequence of an analog may differ from that of the ATM protein when at least one residue is deleted, inserted or substituted but the protein remains functional and does not cause A-T. Differences in glycosylation can provide analogs.

The present invention provides an antibody, either polyclonal or monoclonal, which specifically binds to epitopes on the polypeptide/protein encoded by the ATM gene or mutant epitopes. In preparing the antibody, the protein (with and without mutations) encoded by the ATM gene and polymorphisms thereof is used as a source of the immunogen. Peptide amino acid sequences isolated from the amino acid sequence as set forth in SEQ ID No:3 or mutant peptide sequences can also be used as an immunogen.

The present invention also provides antibodies against the following peptides:
HEPANSSASQSTDLC (SEQ ID No:4),
CKRNLSDIDQSFDKV (SEQ ID No:5),
PEDETELHPTLNADDQEC (SEQ ID No:6), and
CKSLASFIKKPFDRGEVESMEDDTNG (SEQ ID No:7).

The antibodies may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual*, Cold Spring Harbor Laboratory Press, Cold Spring Harbor, N.Y., 1988.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies, the technique involves hyperimmunization of an appropriate donor, generally a mouse, with the protein or peptide fragment and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone and Thorpe, *Immunochemistry* in Practice, Blackwell Scientific Publications, Oxford, 1982.) The binding of antibodies to a solid support substrate is also well known in the art. (see for a general discussion Harlow and Lane *Antibodies: A Laboratory Manual*, Cold Spring Harbor Laboratory Publications, New York, 1988) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

The present invention provides vectors comprising an expression control sequence operatively linked to the nucleic acid sequence of the ATM gene, SEQ ID No:2 and portions thereof as well as mutant sequences which lead to the expression of A-T. The present invention further provides host cells, selected from suitable eucaryotic and procaryotic cells, which are transformed with these vectors.

Using the present invention, it is possible to transform host cells, including *E. coli*, using the appropriate vectors so that they carry recombinant DNA sequences derived from the ATM transcript or containing the entire ATM transcript in its normal form or a mutated sequence containing point mutations, deletions, insertions, or rearrangements of DNA. Such transformed cells allow the study of the function and the regulation of the A-T gene. Use of recombinantly transformed host cells allows for the study of the mechanisms of A-T and, in particular it will allow for the study of gene function interrupted by the mutations in the A-T gene region.

Vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995) and Gilboa et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. See also U.S. Pat. Nos. 5,487,992 and 5,464,764. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Recombinant methods known in the art can also be used to achieve the sense, antisense or triplex inhibition of a target nucleic acid. For example, vectors containing antisense nucleic acids can be employed to express protein or antisense message to reduce the expression of the target nucleic acid and therefore its activity.

A specific example of DNA viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted. For example, if breast cancer is to be treated, then a vector specific for such epithelial cells should be used. Likewise, if diseases or pathological conditions of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The present invention includes the construction of transgenic and knockout organisms that exhibit the phenotypic manifestations of A-T. The present invention provides for transgenic ATM gene and mutant ATM gene animal and cellular (cell lines) models as well as for knockout ATM models. The transgenic models include those carrying the sequence set forth SEQ ID Nos:2,8,9 (or 10). These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, (1991), Capecchi, (1989), Davies et al., (1992), Dickinson et al., (1993), Huxley et al., (1991), Jakobovits et al., (1993), Lamb et al., (1993), Rothstein, (1991), Schedl et al., (1993), Strauss et al., (1993). Further, patent applications WO 94/23049, WO 93/14200, WO 94/06908, WO 94/28123 also provide information. See also in general Hogan et al "Manipulating the Mouse Embryo" Cold Spring Harbor Laboratory Press, 2nd Edition (1994).

According to the present invention, there is provided a method for diagnosing and detecting carriers of the defective gene responsible for causing A-T. The present invention further provides methods for detecting normal copies of the ATM gene and its gene product. Carrier detection is especially important since A-T mutations underlie certain cases of cancer predisposition in the general population. Identifying the carriers either by their defective gene or by their missing or defective protein(s) encoded thereby, leads to earlier and more consistent diagnosis of A-T gene carriers. Thus, since carriers of the disease are more likely to be cancer-prone and/or sensitive to therapeutic applications of radiation, better surveillance and treatment protocols can be initiated for them. Conversely, exclusion of A-T heterozygotes from patients undergoing radiotherapy can allow for establishing routinely higher dose schedules for other cancer patients thereby improving the efficacy of their treatment.

Briefly, the methods comprise the steps of obtaining a sample from a test subject, isolating the appropriate test material from the sample and assaying for the target nucleic acid sequence or gene product. The sample can be tissue or bodily fluids from which genetic material and/or proteins are isolated using methods standard in the art. For example, DNA can be isolated from lymphocytes, cells in amniotic fluid and chorionic villi (Llerena et al., 1989).

More specifically, the method of carrier detection is carried out by first obtaining a sample of either cells or bodily fluid from a subject. Convenient methods for obtaining a cellular sample can include collection of either mouth wash fluids or hair roots. A cell sample could be amniotic or placental cells or tissue in the case of a prenatal diagnosis. A crude DNA could be made from the cells (or alternatively proteins isolated) by techniques well known in the art. This isolated target DNA is then used for PCR analysis (or alternatively, Western blot analysis for proteins) with appropriate primers derived from the gene sequence by techniques well known in the art. The PCR product would then be tested for the presence of appropriate sequence variations in order to assess genotypic A-T status of the subject.

The specimen can be assayed for polypeptides/proteins by immunohistochemical and immunocytochemical staining (see generally Stites and Terr, *Basic and Clinical Immunology*, Appleton and Lange, 1994), ELISA, RIA, immunoblots, Western blotting, immunoprecipitation, functional assays and protein truncation test. In preferred embodiments, Western blotting, functional assays and protein truncation test (Hogervorst et al., 1995) will be used. mRNA complementary to the target nucleic acid sequence can be assayed by in situ hybridization, Northern blotting and reverse transcriptase—polymerase chain reaction. Nucleic acid sequences can be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994)

ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Current mutation data (as shown in Tables 2 and 3) indicate that A-T is a disease characterized by considerable allelic heterogenicity. It is not surprising that there are hundreds (or even thousands) of ATM mutations (as is the case for cystic fibrosis and BRACAI) as shown in Table 3. Thus, it will be important for a successful mutation screen to be able to detect all possible nucleotide alterations in the ATM gene, rather than being focused on a limited subset. Methods including direct sequencing of PCR amplified DNA or RNA or DNA chip hybridization (Fodor et al., 1993; Pease et al., 1994) can be applied along with other suitable methods known to those skilled in the art.

In order to use the method of the present invention for diagnostic applications, it is advantageous to include a mechanism for identifying the presence or absence of target polynucleotide sequence (or alternatively proteins). In many hybridization based diagnostic or experimental procedures, a label or tag is used to detect or visualize for the presence or absence of a particular polynucleotide sequence. Typically, oligomer probes are labelled with radioisotopes such as $^{32}P$ or $^{35}S$ (Sambrook, 1992) which can be detected by methods well known in the art such as autoradiography. Oligomer probes can also be labelled by non-radioactive methods such as chemiluminescent materials which can be detected by autoradiography (Sambrook, 1992). Also, enzyme-substrate based labelling and detection methods can be used. Labelling can be accomplished by mechanisms well known in the art such as end labelling (Sambrook, 1992), chemical labelling, or by hybridization with another labelled oligonucleotide. These methods of labelling and detection are provided merely as examples and are not meant to provide a complete and exhaustive list of all the methods known in the art.

The introduction of a label for detection purposes can be accomplished by attaching the label to the probe prior to hybridization.

An alternative method for practicing the method of the present invention includes the step of binding the target DNA to a solid support prior to the application of the probe. The solid support can be any material capable of binding the target DNA, such as beads or a membranous material such as nitrocellulose or nylon. After the target DNA is bound to the solid support, the probe oligomers is applied.

Functional assays can be used for detection of A-T carriers or affected individuals. For example, if the ATM protein product is shown to have PI 3-kinase biochemical activity which can be assayed in an accessible biological material, such as serum, peripheral leukocytes, etc., then homozygous normal individuals would have approximately normal biological activity and serve as the positive control. A-T carriers would have substantially less than normal biological activity, and affected (i.e. homozygous) individuals would have even less biological activity and serve as a negative control. Such a biochemical assay currently serves as the basis for Tay-Sachs carrier detection.

The present invention also provides a kit for diagnosis and detection of the defective A-T gene. The kit includes a molecular probe complementary to genetic sequences of the defective gene which causes ataxia-telangiectasia (A-T) and suitable labels for detecting hybridization of the molecular probe and the defective gene thereby indicating the presence of the defective gene. The molecular probe has a DNA sequence complementary to mutant sequences. Alternatively, the kit can contain reagents and antibodies for detection of mutant proteins.

The above discussion provides a factual basis for the use and identification of the ataxia-telangiectasia gene and gene products and identification of carriers as well as construction of transgenic organisms. The methods used in the present invention can be shown by the following non-limiting example and accompanying figures.

EXAMPLES

Materials and Methods

General methods in molecular biology: Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989).

Patient and family resources: A cell line repository was established containing 230 patient cell lines and 143 cell lines from healthy members of Moroccan Jewish, Palestinian Arab and Druze families. Some of these pedigrees are highly inbred and unusually large (Ziv et al., 1991; Ziv, 1992). In view of the large number of meiotic events required for high-resolution linkage analysis, applicants collaborated with Dr. Carmel McConville (University of Birmingham, UK) and Dr. Richard Gatti (UCLA, Los Angeles, Calif.), who have also established extensive repositories of A-T families. Linkage analysis was conducted on a pool of 176 families.

Example 1

Definition of the A-T interval by genetic analysis

Studies based only on analysis of Israeli A-T families enabled localization of the A-T(C) gene at 11q22-23 (Ziv, 1991), and confirmed the localization of A-T(A) mutation in Palestinians to the same region (Ziv et al., 1992). Studies with the Birmingham group further narrowed the major A-T interval to 4 centimorgans, between D11S611 and D11S1897 (McConville et al., 1993), and subsequently to 3 centimorgans, between GRIA4 and D11S1897 (Ambrose et al., 1994a; McConville et al., 1994) (see also Shiloh, 1995, and FIG. 1).

All these studies were conducted with biallelic markers, whose power is limited by their low polymorphic information content (PIC). The recently discovered microsatellite markers based on variable numbers of tandem simple repeats (Litt and Luty, 1989; Weber and May, 1989) are much more powerful due to their high degree of polymorphism. Microsatellite markers were used to saturate the A-T region using two approaches. The first, was based on physical mapping of microsatellite markers generated by others which were loosely linked to chromosome 11q.

Mapping experiments were conducted using YAC and cosmid contigs which allowed precise, high-resolution localization of DNA sequences in this region of chromosome 11. These experiments led to the localization of 12 microsatellites at the A-T region (Vanagaite et al., 1994a; Vanagaite et al., 1995).

The second approach was based on generating new microsatellites within the YAC contig. A rapid method for the identification of polymorphic CA-repeats in YAC clones was set up (Rotman, 1995) resulting in the generation of twelve new markers within the A-T locus (Vanagaite et al., 1995; Rotman et al., 1995; Rotman et al., 1994b). Hence, the high-density microsatellite map constructed in this manner contained a total of 24 new microsatellite markers and spans the A-T locus and flanking sequences, over a total of six megabases (Vanagaite et al., 1995).

Figure 1:
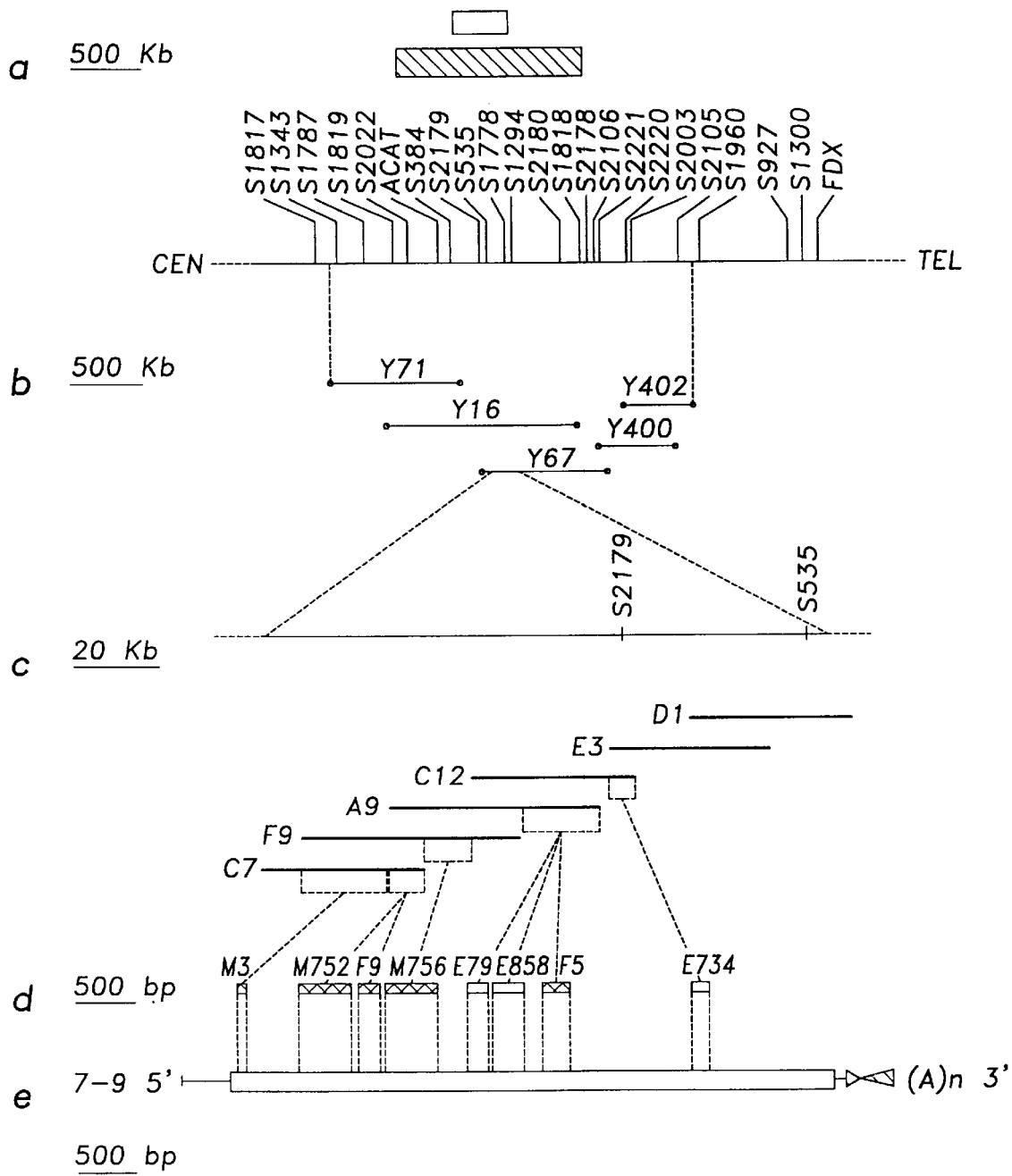

Repeated linkage analysis on the entire cohort of A-T families indicated that the A-T(A) locus was definitely located within a 1.5 megabase region between D11S1819 and D11S1818 (Gatti et al., 1994) as shown in FIG. 1 and in Shiloh (1995), with a clear peak of the cumulative lod score under D11S535 (Lange et al., 1994).

Concomitant with these studies, linkage disequilibrium (LD) analysis of Moroccan-Jewish A-T patients was conducted. LD refers to the non-random association between alleles at two or more polymorphic loci (Chakravarti et al., 1984). LD between disease loci and linked markers is a useful tool for the fine localization of disease genes (Chakravarti et al., 1984; Kerem et al. 1989; Ozelius et al., 1992; Sirugo et al., 1992; Hastbacka et al., 1992; Mitchison et al., 1993). LD is particularly powerful in isolated ethnic groups, where the number of different mutations at a disease locus is likely to be low (Hastbacka et al., 1992; Lehesjoki et al., 1993; Aksentijevitch et al., 1993). Early on, applicants observed very significant LD (p<0.02–p<0.001) between A-T and markers along the D11S1817-D11S927 region in the patients of the sixteen Moroccan-Jewish A-T families identified in Israel (Oskato et al., 1993). Further analysis with the new markers narrowed the peak of linkage disequilibrium to the D11S384-D11S1818 region as shown in FIG. 1.

Haplotype analysis indicated that all of the mutant chromosomes carry the same D11S384-D11S1818 haplotype, suggesting a founder effect for A-T in this community, with one mutation predominating.

Example 2

Sequencing the ATM Gene

Cloning the disease locus in a contig (set of overlapping clones) was essential in isolating the A-T disease gene. The entire A-T locus and flanking region in a contig of yeast artificial chromosomes (YACs) was cloned by methods well known in the art (Rotman et al. 1994c; Rotman et al., 1994d). This contig was instrumental in the construction of the microsatellite map of the region (Vanagaite et al., 1995) and subsequently enabled construction of cosmid contigs extending over most of the interval D11S384-D11S1818. Cosmids corresponding to the YAC clones were identified in a chromosome 11-specific cosmid library supplied by Dr. L. Deaven (Los Alamos National Laboratory) and were ordered into contigs by identifying overlaps as shown in FIG. 1.

Isolation of the A-T gene: Transcribed sequences were systematically identified based on two complementary methods:

1. Use of an improved direct selection method based on magnetic bead capture (MBC) of cDNAs corresponding to genomic clones (Morgan et al., 1992; Tagle et al., 1993). In several, large-scale experiments YAC or cosmid DNA was biotinylated and hybridized to PCR-amplified cDNA from thymus, brain and placenta. Genomic DNA-cDNA complexes were captured using streptavidin-coated magnetic beads which was followed with subsequent elution, amplification, and cloning of captured cDNAs. The cDNA inserts were excised from a gel, self-ligated to form concatamers and sonicated to obtain random fragments. These fragments were size fractionated by gel electrophoresis, and the 1.0–1.5 Kb fraction was extracted from the gel and subcloned in a plasmid vector. The end portions of individual clones were sequenced using vector-specific primers, in an automated sequencer (Model 373A, Applied Biosystems), and the sequences were aligned using the AutoAssembler program (Applied Biosystems Division, Perkin-Elmer Corporation). In the final sequence each nucleotide position represents at least 3 independent overlapping readings.

YACs were also used and were no less efficient than cosmids as starting material for MBC, with more than 50% of the products mapping back to the genomic clones. However, when a small panel of radiation hybrids spanning the A-T region was used to test the cDNA fragments, it was found that some clones that hybridized back to the YACs and cosmids were not derived from this region. This pitfall probably stems from limited homology between certain portions of different genes, and points up the necessity to use radiation hybrid mapping when testing the authenticity of the captured sequences, and not to rely solely on cloned DNA for this purpose.

Homology searches in sequence databases showed that only one of the first 105 cDNA fragments mapped to the A-T region was homologous to a sequence previously deposited in one of the databases, as an expressed sequence tag (EST).

2. Exon amplification, also termed "exon trapping" (Duyk et al., 1990; Buckler et al., 1991), is based on cloning genomic fragments into a vector in which exon splice sites are flagged by splicing to their counterpart sites in the vector. This method of gene identification was expected to complement the MBC strategy, since it does not depend on the constitution of cDNA libraries or on the relative abundance of transcripts, and is not affected by the presence of repetitive sequences in the genomic clones. An improved version of this system (Church et al., 1993) that eliminated problems identified in an earlier version, including a high percentage of false positives and the effect of cryptic splice sites was utilized. Each experiment ran a pool of three to five cosmids with an average of two to five exons identified per cosmid. A total of forty five exons were identified.

Sequence analysis and physical mapping indicated that MBC and exon amplification were complementary in identifying transcribed sequences.

The availability of a deep cosmid contig enabled rapid and precise physical localization of the cDNA fragments and captured exons, leading to a detailed transcriptional map of the A-T region.

Both MBC and exon amplification yielded short (100–1000 bp) transcribed sequences. Those sequences were used as anchor points in isolating full-length clones from twenty eight cDNA libraries currently at applicants disposal and which represented a variety of tissues and cell lines.

Initial screening of the cDNA libraries by polymerase chain reaction (PCR) using primer sets derived from individual cDNA fragments or exons aided in the identification of the libraries most likely to yield corresponding cDNA clones.

Large scale screening experiments were carried out in which most of the cDNA fragments and exons were used in large pools. In addition to the mass screening by hybridization, PCR-based screening methods and RACE (rapid amplification of cDNA ends) (Frohman et al., 1988; Frohman et al., 1994) was employed to identify full-length cDNAs.

The above experiments resulted in the initial identification and isolation of a cDNA clone designated 7-9 (Savitsky et al, 1995a), the complete sequence of which is set forth in SEQ ID No:1 and which is derived from a gene located under the peak of cumulative location score obtained by linkage analysis as shown in FIG. 1. The gene extends over some 300 kilobases (kb) of genomic DNA and codes for two major mRNA species of 12 kb and 10.5 kb in length. The 7-9 clone is 5.9 kb in length and, therefore, is not a full length clone.

An open reading frame of 5124 bp within this cDNA encodes a protein with signature motifs typical of a group of signal transduction proteins known as phosphatidylinositol 3-kinases (PI 3-kinases). PI 3-kinases take part in the complex system responsible for transmitting signals from the outer environment of a cell into the cell. It is not clear yet whether the protein product of the corresponding ATM gene encodes a lipid kinase or a protein kinase.

The gene encoding the 7-9 cDNA clone was considered a strong A-T candidate and mutations were sought in patients. Southern blotting analysis revealed a homozygous deletion in this gene in affected members of Family N., an extended Palestinian Arab A-T family which has not been assigned to a specific complementation group. All the patients in this family are expected to be homozygous by descent for a single A-T mutation. The deletion includes almost the entire genomic region spanned by transcript 7-9, and was found to segregate in the family together with the disease. This finding led to a systematic search for mutations in the 7-9 transcript in additional patients, especially those previously assigned to specific complementation groups.

The restriction endonuclease fingerprinting (REF) method (Liu and Sommer 1995) was applied to reverse-transcribed and PCR-amplified RNA (RT-PCR) from A-T cell lines. Observation of abnormal REF patterns was followed by direct sequencing of the relevant portion of the transcript and repeated analysis of another independent RT product. In compound heterozygotes, the two alleles were separated by subcloning of RT-PCR products and individually sequenced. Genomic sequencing was conducted in some cases to confirm the sequence alteration at the genomic level. Additional family members were studied when available.

Ten sequence alterations (Table 2) were identified in the 7–9 transcript in 13 A-T patients including two sibling pairs. Most of these sequence changes are expected to lead to premature truncation of the protein product, while the rest are expected to create in-frame deletions of 1–3 amino acid residues in this protein. While the consequences of the in-frame deletions remain to be investigated, it is reasonable to assume that they result in impairment of protein function. In one patient, AT3NG, the loss of a serine residue at position 1512 occurs within the PI3-kinase signature sequence. This well conserved domain is distantly related to the catalytic site of protein kinases, hence this mutation is likely to functionally affect the 7–9 protein.

In view of the strong evidence that mutations in this gene are responsible for A-T, it was designated ATM (A-T, Mutated). Since these patients represent all complementation groups of the disease and considerable ethnic variability, these results indicate that the ATM gene alone is responsible for all A-T cases.

In order to complete the cloning of the entire ATM open reading frame, fetal brain and colon random-primed libraries obtained from Stratagene (San Diego, Calif.) and an endothelial cell random-primed library (a gift of Dr. David Ginsburg, University of Michigan) were screened. A total of $1\times10^6$ pfu were screened at a density of 40,000 pfu per 140 mm plate, and replicas were made on Qiabrane filters (Qiagen), as recommended by the manufacturer. Filters were prehybridized in a solution containing 6×SSC, 5×Denhardt's, 1% N-laurylsarcosyl, 10% dextran sulfate and 100 $\mu$g/ml salmon sperm DNA for 2 hours at 65° C. Hybridization was performed for 16 hrs under the same conditions with $1\times10^6$ cpm/ml of $^{32}$P-labelled probe, followed by final washes of 30 minutes in 0.25×SSC, 0.1% SDS at 60° C. Positive clones were plaque-purified using standard techniques and sequenced. DNA sequencing was performed using an automated DNA sequencer (Applied Biosystems, model 373A), and the sequence was assembled using the AutoAssembler program (Applied Biosystems Division, Perkin-Elmer Corporation). In the final sequence, each nucleotide represents at least four independent readings in both directions.

Database searches for sequence similarities were performed using the BLAST network service. Alignment of protein sequences and pairwise comparisons were done using the MACAW program, and the PILEUP and BESTFIT programs in the sequence analysis software package developed by the Genetics Computer Group at the University of Wisconsin.

Example 3

Detection of Mutations

Determination of mutations: The recently discovered ATM gene is probably involved in a novel signal transduction system that links DNA damage surveillance to cell cycle control. A-T mutations affect a variety of tissues and lead to cancer predisposition. This striking phenotype together with the existence of "partial A-T phenotypes" endow the study of ATM mutations with special significance.

MATERIALS AND METHODS

RT-PCR: Total RNA was extracted from cultured fibroblast or lymphoblast cells using the Tri-Reagent system (Molecular research Center, Cincinnati, Ohio). Reverse transcription was performed on 2.5 ug of total RNA in a final volume of 10 ul, using the Superscript II Reverse Transcriptase (Gibco BRL, Gaithersburg, Md.) in the buffer recommended by the supplier, and in the presence of 125 U/ml of RNAsin (Promega) and 1 mM dNTPs (Pharmacia). Primers were either oligo(dT) (Pharmacia) or a specifically designed primer. The reaction products were used as templates for PCR performed with specific primers. These reactions were carried out in 50 μl containing 2 units of Taq DNA Polymerase (Boehringer Mannheim, Mannheim, Germany), 200 μM dNTPs, 0.5 μM of each primer, and one tenth of the RT-PCR products. The products were purified using the QIA-quick spin system (Qiagen, Hilden, Germany).

Restriction endonuclease fingerprinting: The protocol of Liu and Sommer (1995) was followed with slight modifications. RT-PCR was performed as described above, using primers defining PCR products of 1.0–1.6 kb. One hundred ng of amplified DNA was digested separately with 5 or 6 restriction endonucleases in the presence of 0.2 units of shrimp alkaline phosphatase (United States Biochemicals, Cleveland, Ohio). Following heat inactivation at 65° C. for 10 minutes, the digestion products corresponding to the same PCR product were pooled, denatured at 96° C. for 5 minutes and immediately chilled on ice. Ten ng of this fragment mixture was labeled in the presence of 6 μCi of [γ-$^{33}$P]ATP and 1 unit of T4 polynucleotide kinase (New England Biolabs, Beverly, Mass.) at 37° C. for 45 minutes. Twenty μl of stop solution containing 95% formamide, 20 mM EDTA, 0.05% bromophenol blue, 0.05% xylene cyanol, and 10 mM NaOH were added, and the samples were boiled for 3 minutes and quick-chilled on ice. Electrophoresis was performed in 5.6% polyacrylamide gels in 50 mM Tris-borate, pH 8.3, 1 mM EDTA at constant power of 12 W for 3 hours at room temperature, with a fan directed to the glass plates, keeping them at 22°–24° C. The gels were dried and subjected to autoradiography.

Direct sequencing of PCR products: Five hundred ng of PCR products was dried under vacuum, resuspended in reaction buffer containing the sequencing primer, and the mixture was boiled and snap-frozen in liquid nitrogen. The Sequenase II system (Unites States Biochemicals) was used to carry out the sequencing reaction in the presence of 0.5 μg of single-strand binding protein (T4 gene 32 protein, United States Biochemicals). The reaction products were treated with 0.1 μg of proteinase K at 65° C. for 15 minutes, separated on a 6% polyacrylamide gel, and visualized by autoradiography.

Using the methods described herein above the ATM transcript was scanned for mutations in fibroblast and lymphoblast cell lines derived from an extended series of A-T patients from 13 countries, all of whom were characterized by the classical A-T phenotype. The analysis was based on RT-PCR followed by restriction endonuclease fingerprinting (REF). REF is a modification of the single-strand conformation polymorphism (SSCP) method, and enables efficient detection of sequence alterations in DNA fragments up to 2 kb in length (Liu and Sommer, 1995).

Briefly, after PCR amplification of the target region, multiple restriction endonuclease digestions are performed prior to SSCP analysis, in order to increase the sensitivity of the method and enable precise localization of a sequence alteration within the analyzed fragment. The coding sequence of the ATM transcript, which spans 9168 nucleotides (SEQ ID No:2) (Savitsky et al., 1995b), was thus divided into 8 partly overlapping portions of 1.0–1.6 Kb, and each one was analyzed separately. Sequence alterations causing abnormal REF patterns were located and disclosed by direct sequencing. Mutations identified in this way were reconfirmed by repeating the RT-PCR and sequencing, or by testing the presence of the same mutations in genomic DNA.

In compound heterozygotes, the two alleles were separated by subcloning and individually sequenced. In some cases, agarose gel electrophoresis showed large deletions in the ATM transcript manifested as RT-PCR products of reduced sizes. The breakpoints of such deletions were delineated by direct sequencing of these products.

The 44 mutations identified to date in our patient cohort (Table 3) include 34 new ones and 10 previously identified ones (Table 2). (Mutations in Table 3 are presented according to the nomenclature proposed by Beaudet & Tsui (1993); nucleotide numbers refer to their positions in the sequence of the ATM transcript (accession number U33841); the first nucleotide of the open reading frame was designated +1.) These mutations were found amongst 55 A-T families: many are unique to a single family, while others are shared by several families, most notably the 4 nt deletion, 7517del4, which is common to 6 A-T families from South-Central Italy (Table 3). According to this sample, there is a considerable heterogeneity of mutations in A-T, and most of them are "private". The proportion of homozygotes in this sample is relatively high due to a high degree of consanguinity the populations studied. It should be noted, however, that apparently homozygous patients from non-consanguineous families may in fact be compound heterozygotes with one allele not expressed.

This series of 44 A-T mutations is dominated by deletions and insertions. The smaller ones, of less than 12 nt, reflect identical sequence alterations in genomic DNA. Deletions spanning larger segments of the ATM transcript were found to reflect exon skipping, not corresponding genomic deletions. This phenomenon usually results from sequence alterations at splice junctions or within introns, or mutations within the skipped exons, mainly of the nonsense type (Cooper and Krawczak, 1993; Sommer, 1995; Steingrimsdottir et al., 1992; Gibson et al., 1993; Dietz and Kendzior, 1994). One large deletion spans about 7.5 Kb of the transcript and represents a genomic deletion of about 85 Kb within the ATM gene. Of these deletions and insertions, 25 are expected to result in frameshifts. Together with the 4 nonsense mutations, truncation mutations account for 66% of the total number of mutations in this sample. Seven in-frame deletions span long segments (30–124 aa) of the protein, and similarly to the truncation mutations, are expected to have a severe effect on the protein's structure. It should be noted that two base substitutions abolish the translation initiation and termination codons. The latter is expected to result in an extension of the ATM protein by an additional 29 amino acids. This mutation may affect the conformation of the nearby PI 3-kinase-like domain.

While the effect of the 4 small (1–3 aa) in-frame deletions and insertions on the ATM protein remains to be studied, it should be noted that one such deletion (8578del3) leads to a loss of a serine residue at position 2860. This amino acid is part of a conserved motif within the PI 3-kinase-like domain typical of the protein family to which ATM is related, and is present in 7 of 9 members of this family. The single missense mutation identified in this study, which leads to a Glu2904Gly substitution, results in a nonconservative alteration of another extremely conserved residue within this domain, which is shared by all of these proteins. The patient homozygous for this mutation, AT41RM, shows the typical clinical A-T phenotype. Measurement of radioresistant DNA synthesis in the patient's cell line revealed a typical A-T response, demonstrating that this patient has the classical A-T cellular phenotype.

As discussed herein above, the ATM gene of the present invention is probably involved in a novel signal transduction system that links DNA damage surveillance to cell cycle control. A-T mutations affect a variety of tissues and lead to cancer predisposition. This striking phenotype together with the existence of "partial A-T phenotypes" endow the study of ATM mutations with special significance.

The ATM gene leaves a great deal of room for mutations: it encodes a large transcript. The variety of mutations identified in this study indeed indicates a rich mutation repertoire. Despite this wealth of mutations, their structural characteristics point to a definite bias towards those that inactivate or eliminate the ATM protein. The nature or distribution of the genomic deletions among these mutations do not suggest a special preponderance of the ATM gene for such mutations, such as that of the dystrophin (Anderson and Kunkel, 1992) or steroid sulfatase (Ballabio et al., 1989) genes which are particularly prone to such deletions. Thus, one would have expected also a strong representation of missense mutations, which usually constitute a significant portion of the molecular lesions in many disease genes (Cooper and Krawczak, 1993; Sommer, 1995). However, only one such mutation was identified in the present study. Other point mutations reflected in this series are those that probably underlie the exon skipping deletions observed in many patients, again, exerting a severe structural effect on the ATM protein.

A technical explanation for this bias towards deletions and insertions could be a greater ability of the REF method to detect such lesions versus its ability to detect base substitution. Liu and Sommer (1995) have shown, however, that the detection rate of this method in a sample of 42 point mutations in the factor IX gene ranged between 88% and 100%, depending on the electrophoresis conditions. The 7 base substitutions detected directly by the REF method in the present study (Table 2), indicate that such sequence alterations are detected in our hands as well.

Since the expected result of most of these mutations is complete inactivation of the protein, this skewed mutation profile might represent a functional bias related to the studied phenotype, rather than a structural feature of the ATM gene that lends itself to a particular mutation mechanism. The classical A-T phenotype appears to be caused by homozygosity or compound heterozygosity for null alleles, and hence is probably the most severe expression of defects in the ATM gene. The plethora of missense mutations expected in the large coding region of this gene is probably rarely represented in patients with classical A-T, unless such a mutation results in complete functional inactivation of the protein. By inference, the only missense identified in this study, Glu2940Gly, which substitutes a conserved amino acid at the PI 3-kinase domain and clearly gives rise to a classical A-T phenotype, points to the importance of this domain for the biological activity of the ATM protein. Mutations in this domain abolish the telomere-preserving function of the TEL1 protein in S. cerevisiae (Greenwell et al., 1995), a protein which shows a particularly high sequence similarity to ATM (Savitsky et al., 1995b; Zakian, 1995). Another member of the family of PI 3-kinase-related proteins that includes ATM is the mammalian FRAP. Mutations in the PI 3-kinase domain abolish its autophosphorylation ability and biological activity (Brown et al., 1995). These observations, together with the mutation shown here, suggest that this domain in ATM is also likely to include the catalytic site, which may function as a protein kinase.

Genotype-phenotype relationships associated with the ATM gene appear therefore to extend beyond classical A-T.

There are several examples of genes in which different mutations lead to related but clinically different phenotypes. For example, different combinations of defective alleles of the ERCC2 gene may result in xeroderma pigmentosum (group D), Cockayne's syndrome or trichothiodystrophy— three diseases with different clinical features involving UV sensitivity (Broughton et al., 1994, 1995).

Different mutations in the CFTR gene may lead to fullfledged cystic fibrosis, or only to congenital bilateral absence of the vas deferens which is one feature of this disease (Chillon et al., 1995; Jarvi et al., 1995). A particularly interesting example is the X-linked WASP gene responsible for Wiskott Aldrich syndrome (WAS), characterized by immunodeficiency, eczema and thrombocytopenia. Most of the mutations responsible for this phenotype cause protein truncations; however, certain missense mutations may result in X-linked thrombocytopenia, which represents a partial WAS phenotype, while compound heterozygosity for a severe and mild mutation results in females in an intermediate phenotype (Kolluri et al., 1995; Derry et al., 1995).

In a similar manner, genotypic combinations of mutations with different severities create a continuous spectrum of phenotypic variation in many metabolic diseases.

Which phenotypes are most likely to be associated with milder ATM mutations? Since cerebellar damage is the early and severe manifestation of A-T, it is reasonable to assume that the cerebellum might also be affected to some extent in phenotypes associated with milder ATM mutations. Such phenotypes may include cerebellar ataxia, either isolated (Harding, 1993) or coupled with various degrees of immunodeficiency. The latter combination has indeed been described, sometimes with chromosomal instability, and is often designated "ataxia without telangiectasia" (Ying and Decoteau, 1983; Byrne et al., 1984; Aicardi et al., 1988; Maserati, 1988; Friedman and Weitberg, 1993). Friedman and Weitberg (1993) recently suggested a new clinical category of "ataxia with immune deficiency" that would include A-T as well as other cases of cerebellar degeneration with immune deficits. Evaluation of patients with cerebellar disorders with the present invention may reveal a higher frequency of such cases than previously estimated. However, in view of the pleiotropic nature of the ATM gene, the range of phenotypes associated with various ATM genotypes may be even broader, and include mild progressive conditions not always defined as clear clinical entities. Screening for mutations in this gene in such cases may reveal wider boundaries for the molecular pathology associated with the ATM gene.

Example 4

Determination of Genomic Organization

The exon/intron boundaries and the intron sizes were determined using long-distance PCR (Barnes, 1994; Cheng et al., 1994; Foord and Rose, 1994). Primers were designed based on the ATM cDNA sequence (Savitsky et al., 1995a,b) at 200–300 bp intervals. Templates for these reactions were cosmid and YAC clones, and human genomic DNA. PCR products were obtained in all cases, including those that span the largest intron, of 11 kb. In the large majority of cases, PCR products of the same size were obtained with all templates, and those obtained from genomic DNA were used for sequencing of the exon-intron junctions. Following initial reactions, new primers were designed as needed, based on the evolving knowledge of the gene structure. Exon-intron boundaries were determined at the sites where genomic and cDNA sequences diverged. Typical splice acceptor and donor sequences were found around these sites in all cases. During the search for the A-T gene, six exons were isolated by exon trapping (Shiloh et al., 1994b) using the vectors pSPL3 (Church et al., 1994) and éGET (Nehls et al., 1994a,b). Their boundaries coincided with those obtained by long-distance PCR.

Parallel with these experiments, an effort was initiated to sequence the entire ATM gene. The sequence of one cosmid, B10, has been completed to date. This cosmid spans a portion of the gene containing the first 10 exons and upstream sequences. Comparison of this genomic sequence to the cDNA sequence yielded exon boundaries which coincided with those obtained by long-distance genomic PCR.

The ATM gene is composed of 65 exons (FIG. 2 and Table 1). The first two exons are alternatively spliced, and are designated 1a (SEQ ID No:10) and 1b (SEQ ID No:9). With the exception of the 3' exon, ATM exons range in size from 64 to 372 bp, with an average of 149 bp. The introns vary considerably in size, from 100 bp to about 11 kb, with the majority in the range of 1–3 kb. The consensus dinucleotides GT and AG were found at the donor and acceptor splice sites of all introns, except for a variant donor site with a GC dinucleotide (reviewed in Jackson, 1991) present in the intron 3' to exon 51. The first methionine of the open reading frame is located in exon 3, whereas the stop codon is located in the 3' and largest exon of 3.6 kb. This exon includes a 3' untranslated region (UTR) (SEQ ID No:8) of about 3400 nucleotides.

The ATM gene contains one of the largest number of exons reported to date for a human gene. However, these exons are spread over a relatively compact genomic region of about 150 kb. The dystrophin gene, for example, consists of 79 exons spanning 2.4 Mb of genomic DNA (Roberts et al., 1993), while the Huntington's disease gene consists of 67 exons spread over 180 Kb (Ambrose et al., 1994b).

Throughout this application various publications and patents are referenced by citation or number. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

EXON-INTRON ORGANIZATION OF THE ATM GENE

| Exon No. | 5' intronic sequence | | Exon First Base* | Exon length (bp) | Exon Last Base* | 3' intronic sequence | | Size of 3' intron (kb) |
|---|---|---|---|---|---|---|---|---|---|---|
| 1a§ | | | -915 | AGGTAG | 120 | GCAGTG | -796 | gtaggggcgcggaggcaacgcagcagcggcttc | SEQ ID No. 11 | 0.18 |
| 1b§ | | | -795 | TCCTCC | 634 | TACCAG | -162 | gtatgagcgaagaagagatcaggagac | SEQ ID No. 12 | 0.09 |
| 2 | tgatcattgctaacattgctgtgtttxag | SEQ ID No. 13 | -161 | GCACTG | 43 | ATAGAG | -119 | gtaggtactagtatgtttccttatc | SEQ ID No. 14 | 0.65 |
| 3 | tttcttattactgtgtttgttcctcag | SEQ ID No. 15 | -118 | AGGCAT | 88 | ATGAGG | -31 | gtaggattgtatcgttagtcatat | SEQ ID No. 16 | 2.75 |
| 4 | tatatataccatatgtatttttacag | SEQ ID No. 17 | -30 | ACAGTG | 102 | CGAAAG | 72 | gtagtaaattacttaaatcaattttct | SEQ ID No. 18 | 0.08 |
| 5 | aaccatatattccttatttcag | SEQ ID No. 19 | 73 | AAAGAA | 113 | TTTTAG | 185 | gtatctatcaaattattactgtct | SEQ ID No. 20 | 1.30 |
| 6 | ttctgaaattgcatttgttcttattcag | SEQ ID No. 21 | 186 | ATTTT | 146 | ACAGAA | 331 | gtaaggatgtataaattataaataaatggc | SEQ ID No. 22 | 6.35 |
| 7 | gttttcttattgttattgaaatag | SEQ ID No. 23 | 332 | GAGCAC | 165 | GGTTAG | 496 | gtatgtttgaaggtgttgttggaattttt | SEQ ID No. 24 | 8.10 |
| 8 | catgactaataatttttttag | SEQ ID No. 25 | 497 | AATTGT | 166 | TGCGAG | 662 | gtaatctaatcttttctttttgtttgtatg | SEQ ID No. 26 | 0.67 |
| 9 | cccagttgagctgttgttcttcacag | SEQ ID No. 27 | 663 | ACAAGA | 239 | AAAAAG | 901 | gtataaaggaaatgttactgtttgaattt | SEQ ID No. 28 | 1.94 |
| 10 | aaaaatacatttaaattttggattcag | SEQ ID No. 29 | 902 | GTGCTT | 164 | CACCAG | 1065 | gtacagtaaggtaggcatgtcacatttaga | SEQ ID No. 30 | 1.80 |
| 11 | gaaaaagtggattatttatttaatcag | SEQ ID No. 31 | 1066 | GTTTTT | 170 | GCCTTG | 1235 | gtaagttgtaccatttctcattcagtgt | SEQ ID No. 32 | 1.60 |
| 12 | ttccaaataaccctttttttttag | SEQ ID No. 33 | 1236 | GCTACA | 372 | TTCATG | 1607 | gtaagtcagcatgcattagcatgctgtt | SEQ ID No. 34 | 0.80 |
| 13 | tttttcacaattgtcctttgtttgttatag | SEQ ID No. 35 | 1608 | TCCTGC | 195 | TCACAG | 1802 | gtaattttaagttcattagcatgctctttatcat | SEQ ID No. 36 | 0.90 |
| 14 | ctaagtgaagctttgtgtttgttcttgtag | SEQ ID No. 37 | 1803 | TAATTT | 96 | AGAATG | 1898 | gtatgttatctaataatgctctttatcat | SEQ ID No. 38 | 0.90 |
| 15 | ttatatattaaagatcttttctctgaaag | SEQ ID No. 39 | 1899 | TGAACA | 226 | TCTGAG | 2124 | gtgagatttttaaaaaagaactaagctt | SEQ ID No. 40 | 2.20 |
| 16 | tatatattttaattggttactttag | SEQ ID No. 41 | 2125 | ATTACA | 126 | GCCAAC | 2250 | gtaggagaatttatacatcaagtaaagtctcgg | SEQ ID No. 42 | 1.15 |
| 17 | aatttgcatttttcctcattcacaatag | SEQ ID No. 43 | 2251 | TCTCTA | 126 | ACCAAG | 2376 | gtaagatttctctcgtttgttt | SEQ ID No. 44 | 1.40 |
| 18 | tgcttggttcttttgtctaattgcag | SEQ ID No. 45 | 2377 | AAGAGT | 90 | AGTTTA | 2466 | gtaagtactatattactggatttgctatcatat | SEQ ID No. 46 | 8.10 |
| 19 | cttgaacatctttgttcttcctcgaag | SEQ ID No. 47 | 2467 | GCATCC | 172 | CCATAG | 2638 | gtaaatacatatttacactggatttct | SEQ ID No. 48 | 1.10 |
| 20 | ttagttgtaatgtgctttattttag | SEQ ID No. 49 | 2639 | GTGCCA | 200 | CATATC | 2838 | gtggagttacgtaaatgaagaagctcttg | SEQ ID No. 50 | 2.50 |
| 21 | cctgatttttcccttccctccaccattag | SEQ ID No. 51 | 2839 | TATCTA | 83 | ACTATC | 2921 | gtaagaaatttaaaacctatgttatgttca | SEQ ID No. 52 | 0.10 |
| 22 | aagttgaactttttttttttttttaccacag | SEQ ID No. 53 | 2922 | CAATGT | 156 | AITTTG | 3077 | gtaggtacagtcattttgtgctccat | SEQ ID No. 54 | 1.20 |
| 23 | tttaacttgaaaacttactgatttcag | SEQ ID No. 55 | 3078 | GCATCT | 76 | CTTGAG | 3153 | gtgagtttgcatttttgtaagatct | SEQ ID No. 56 | 0.10 |
| 24 | tcatattcaaccacagtctcttcccgtag | SEQ ID No. 57 | 3154 | GCTGAT | 131 | CAATAG | 3284 | gtaatggtcaaatatcatgaagatatgg | SEQ ID No. 58 | 7.00 |
| 25 | tttcatgtttcttcctccgtctaag | SEQ ID No. 59 | 3285 | ATTGTT | 118 | GAAATG | 3402 | gtaattttaagtaacatgtatttgctgtta | SEQ ID No. 60 | 1.30 |
| 26 | ttacaattttttaattcttttag | SEQ ID No. 61 | 3403 | TCCCAT | 174 | AAAAAG | 3576 | gtatatatggatgagtatttattagaagc | SEQ ID No. 62 | 1.50 |
| 27 | cttaacacattgactttgtcgtcag | SEQ ID No. 63 | 3577 | GTTTTA | 170 | CTATAG | 3746 | gtgtttatacatgacatatgtgaaatt | SEQ ID No. 64 | 1.35 |
| 28 | aacctgtatttaaattttcatttttag | SEQ ID No. 65 | 3747 | ATCTTG | 247 | AAACAG | 3993 | gtalggctcaattttatgtacttttcat | SEQ ID No. 66 | 3.01 |
| 29 | taaatatatttaaatttgccctgtcag | SEQ ID No. 67 | 3994 | ATTGAT | 116 | TTCAGG | 4109 | gtagtacatttaaactagaagaactagc | SEQ ID No. 68 | 1.30 |
| 30 | tgactgtatttttccctaactgtag | SEQ ID No. 69 | 4110 | GGATTT | 127 | AGCCCT | 4236 | gtaagtaccatgatgagtttaatgc | SEQ ID No. 70 | 0.50 |
| 31 | aagtttactaaalcgttatttttcag | SEQ ID No. 71 | 4237 | GATTTC | 200 | CCAAAG | 4436 | gtaaactacagtatttagaccaatatataag | SEQ ID No. 72 | 2.80 |
| 32 | ttgtgtgttttttttctccctattag | SEQ ID No. 73 | 4437 | GCCTTC | 175 | AAACAG | 4611 | gtaatttctgactcatctcaaaatgta | SEQ ID No. 74 | 0.52 |
| 33 | tataattttcttttaaattatatag | SEQ ID No. 75 | 4612 | GTATTG | 165 | TTGGAG | 4776 | gtaataaaatttcatcatcatactattt | SEQ ID No. 76 | 1.45 |
| 34 | gttaaaagcaagttacatttctcttag | SEQ ID No. 77 | 4777 | GAAATT | 133 | CTCAGG | 4909 | gtgctaatttaaatgacatgggctatt | SEQ ID No. 78 | 2.25 |
| 35 | ttaaactaatttaaattaattctcag | SEQ ID No. 79 | 4910 | ATAATC | 96 | TTCTAG | 5005 | gtaaactacagtcatgctcgctgacatt | SEQ ID No. 80 | 2.35 |
| 36 | ctgaaatagaattttcatatgtag | SEQ ID No. 81 | 5006 | AGGGCTG | 172 | AGATTG | 5177 | gtgagatttagtaccttatatgtaat | SEQ ID No. 82 | 1.76 |
| 37 | ctgataggcattgaattgttttttcag | SEQ ID No. 83 | 5178 | TGTCAA | 142 | AAAAAG | 5319 | gtctctaagtaataaaatgttaatgaata | SEQ ID No. 84 | 1.05 |
| 38 | attacattttctaatcccttttcctag | SEQ ID No. 85 | 5320 | TTTTTA | 177 | TGTGAA | 5496 | gtaagaagattaattagtctgatataattc | SEQ ID No. 86 | 1.65 |
| 39 | tatgggtgattgttgtatattcag | SEQ ID No. 87 | 5497 | GTGAAA | 178 | ATTCAG | 5674 | gtatctataattttaacattaatact | SEQ ID No. 88 | 3.05 |
| 40 | ggactgagggagagatattttgttttgttcag | SEQ ID No. 89 | 5675 | AGTCAG | 88 | AAAGAG | 5762 | gtatctaagtaagtgtgctcttacgttt | SEQ ID No. 90 | 2.15 |
| 41 | tgaatgacattatctcatttcttag | SEQ ID No. 91 | 5763 | ACCTTC | 156 | GAAAAG | 5918 | gtaatggaattagaattttgttttaa | SEQ ID No. 92 | 2.10 |
| 42 | cattaaaagaggtgttcttgtgacaaacag | SEQ ID No. 93 | 5919 | AAGTCT | 88 | TTACAG | 6006 | gtaatattagaggctcattattatgac | SEQ ID No. 94 | 3.30 |
| 43 | ctcaattttgtgttcgtttcag | SEQ ID No. 95 | 6007 | GATCTT | 89 | TACTAG | 6095 | gtaaattgcattttcaaacaacgtatag | SEQ ID No. 96 | 0.10 |
| 44 | cccaagctattttcacatcttttcttatag | SEQ ID No. 97 | 6096 | ACTACG | 103 | ATTCAG | 6198 | gtacttttttcccagattggtaaagcca | SEQ ID No. 98 | 1.26 |

TABLE 1-continued

EXON-INTRON ORGANIZATION OF THE ATM GENE

| Exon No. | 5' intronic sequence | | Exon First Base* | Exon length (bp) | Exon Last Base* | 3' intronic sequence | | Size of 3' intron (kb) |
|---|---|---|---|---|---|---|---|---|
| 45 | aacttaaaacaacaataactcctgtttag | SEQ ID No. 99 | GCCTTG | 6199 | 149 | CGTCAG | 6347 | gtaagaaatttgactgatttttttt | SEQ ID No. 100 | 2.50 |
| 46 | gtatattttcttgactatctcacag | SEQ ID No. 101 | CAAAGA | 6348 | 105 | TGCCAG | 6452 | gtatatgaaaagacaaagttacgtatttt | SEQ ID No. 102 | 1.25 |
| 47 | ttcagagtgtctttttttgctactag | SEQ ID No. 103 | AGTAAA | 6453 | 120 | CTCAAG | 6572 | gtagtaattcgtatgactggttatccta | SEQ ID No. 104 | 4.00 |
| 48 | cttacatgaactctatgtcgtggcattcag | SEQ ID No. 105 | ATCAGT | 6573 | 235 | ACTCAG | 6807 | gtaaatacaatttaaaactatgtcatctta | SEQ ID No. 106 | 0.51 |
| 49 | attattcccatagtcatttcatttcag | SEQ ID No. 107 | CTCCCT | 6808 | 168 | GCAGCG | 6975 | gttgtttttttattggctgattagtgt | SEQ ID No. 108 | 1.40 |
| 50 | tatatttaagatttgcctttctatacag | SEQ ID No. 109 | AACAAT | 6976 | 114 | GAAAAG | 7089 | gtaagatttttggagcaaccctaagatag | SEQ ID No. 110 | 1.30 |
| 51 | tataatttaaatggtgtgttttctgaag | SEQ ID No. 111 | GCAGTA | 7090 | 218 | AAACAG | 7307 | gtaactaggttctacaagtgacaattta | SEQ ID No. 112 | 1.00 |
| 52 | ttgtgtttacctaattattctatgcaag | SEQ ID No. 113 | ATACAC | 7308 | 208 | ATGAAG | 7515 | gcaagtgttactcagcccaatatctacc | SEQ ID No. 114 | 1.00 |
| 53 | cttaatttgtctttttttaatggtag | SEQ ID No. 115 | AGAGAC | 7516 | 114 | AATAAT | 7629 | gtaagtaaacctgaaaatcaaacacaata | SEQ ID No. 116 | 0.32 |
| 54 | tgcataaatctaatagtctttttctacag | SEQ ID No. 117 | CTAATC | 7630 | 159 | GATGAG | 7788 | gtattggatttaaacatacgtacctttag | SEQ ID No. 118 | 0.70 |
| 55 | tatgtaatgttttttgtttttattaatag | SEQ ID No. 119 | GATCGA | 7789 | 139 | AGAGAA | 7927 | gtagtttttttaaagaagaaacgttact | SEQ ID No. 120 | 1.00 |
| 56 | tcactaaaatctctcatttttaaatacag | SEQ ID No. 121 | AAGGCA | 7928 | 83 | ATTAAG | 8010 | gtaatttgcaattaactcttgatttttt | SEQ ID No. 122 | 1.00 |
| 57 | ctattatcaatcatgtttatacttttattag | SEQ ID No. 123 | GTGGAC | 8011 | 141 | GTTAAG | 8151 | gtgagccttccctcctctggcttagcct | SEQ ID No. 124 | 0.80 |
| 58 | actgttattcatgcttaatatttctgaag | SEQ ID No. 125 | GGCCGT | 8152 | 117 | TATAAG | 8268 | gtaactattgtactctgttagttcacca | SEQ ID No. 126 | 7.50 |
| 59 | aattaaaaggtatttaatcgtaactccag | SEQ ID No. 127 | GTGGTT | 8269 | 150 | ATGATG | 8418 | gtgagtgacaccccaaaattaaaggttattg | SEQ ID No. 128 | 2.40 |
| 60 | aaaataatatatatctcatttaaag | SEQ ID No. 129 | GAGGTG | 8419 | 166 | CTATTG | 8584 | gtaatctcttgtacatatagtagatgag | SEQ ID No. 130 | 1.40 |
| 61 | ttcagatgttgttctttttctcccag | SEQ ID No. 131 | TTGGTT | 8585 | 87 | ATCTAG | 8671 | gtaagtaataaaatctatgtatctattct | SEQ ID No. 132 | 6.00 |
| 62 | cctctaacttcactgtattctttacttag | SEQ ID No. 133 | GTGTTG | 8672 | 115 | CAGAAG | 8786 | gtaagtgatatgaagtaaggaggaaat | SEQ ID No. 134 | 1.00 |
| 63 | atccgtatttataatgtgttttgactctag | SEQ ID No. 135 | ATGCTG | 8787 | 64 | GTAGAG | 8850 | gtaaagtatttataaggaggactttattt | SEQ ID No. 136 | 11.0 |
| 64 | aagaacagatgtctctgtttag | SEQ ID No. 137 | GTCCTT | 8851 | 137 | TCTCAG | 8987 | gggagcagtatttaagaaggtccgtgt | SEQ ID No. 138 | 0.10 |
| 65 | actggaaccttgtgttttgtccttag | SEQ ID No. 139 | TGATAT | 8988 | ~3600 | | | | | |

*The first nucleotide of the open reading frame was designated +1.
§1a and 1b are alternatively spliced 5' non-coding exons.

TABLE 2 illustrates several mutations found in A-T patients

| Patient[1] | Ethnic/ geographic origin | Complementation group[4] | Mutation mPNA sequence change | Protein alteration | Codon[9] | Patient's genotype[10] |
|---|---|---|---|---|---|---|
| AT2RO | Arab | A | Deletion of 11 nt[5] | Frameshift, truncation | 499 | Homozygote |
| AT3NG | Dutch | A | Deletion of 3 nt | Deletion, 1 residue[8] | 1512 | Compound heterozygote |
| AT15LA | Philippine | A | Insertion, +A | Frameshift, truncation | 557 | Compound heterozygote |
| AT3LA[2] AT4LA[2] | African-American | C | Deletion of 139 nt[6]/ Deletion of 298 nt[6] | Frameshift, trunction | 1196 | Compound heterozygotes |
| AT2BR | Celtic/Irish | C | Deletion, 9 nt | Deletion, 3 residues | 1198–1200 | Homozygote |
| AT1ABR AT2ABR | Australian (Irish/British) | E | Deletion, 9 nt | Deletion, 3 residues | 1198–1200 | Homozygote |
| AT5BI[2] AT6BI[2] | Indian/English | D | Deletion, 6 nt | Deletion, 2 resdiues | 1079–1080 | Compound heterozygotes |
| F-2079[3] | Turkish | ND | Insertion, +C[5] | Frameshift, trunation | 504 | Homozygote |
| AT29RM | Italian | ND | Deletion of 175 nt | Frameshift, truncation | 132 | Homozygote |
| AT103LO | Canadian | ND | Insertion, +A | Frameshift, truncation | 1635 | Homozygote |
| F-596[3] | Palestinian Arab | ND | Deletion[7] | Truncation | Host of ORF | Homoxygote |

[1]Cell line designation.
[2]Sibling patients in both of whom the same mutation was identified.
[3]Patient expected to be homozygous by descent for an A-T mutation.
[4]According to the methods of Jaspers et al. (1988) ND: not determined.
[5]An identical sequence change was observed in genomic DNA
[6]No evidence for deletion was observed in genomic DNA. In both siblings, a normal mRNA was observed in addition to the two deleted species. The two deleted mRNAs may represent abnormal splicing events caused by a splice site mutation.
[7]Reflects a genomic deletion segregating with the disease in Family N.
[8]The deleted serine residue is located within the PI3-kinase signtaure sequence (1507–1527 of SEQ ID No:2).
[9]Numbers refer to residue positions in SEQ ID No:2.
[10]In all the compound heterozygotes, the second mutation is still unidentified.

TABLE 3

Mutations in the ATM gene in patients with classical A–T.

| mRNA sequence change[1] | Predicted protein alteration | Codon[8] | Patient | Ethnic/ geographical origin | Genotype[11] |
|---|---|---|---|---|---|
| Truncations and exon skipping deletions: | | | | | |
| 9001delAG | Truncation | 3001 | 91RD90[9] | Turkish | Hmz |
| 8946insA | Truncation | 2983 | AT103LO | American | Hmz |
| 8307G->A | Trp->ter; truncation | 2769 | AT2SF | American | Compd Htz |
| 8283delTC | Truncation | 2762 | AT28RM | Italian | Compd Htz |
| 8269del1403[2] | Truncation | 2758 | AT17RM | Italian | Hmz |
| 8269del1503 | Del, 50 aa | 2758 | F-2086 | Turkish | Compd Htz |
|  |  |  | GM9587 | American | Compd Htz |
| 8140C->T | Gln->ter; truncation | 2714 | IARC12/AT3 | French | Hmz |
| 7883del5 | Truncation | 2620 | ATF104 | Japanese | Hmz |
|  |  |  | JCRB316 | Japanese |  |
| 7789del139/7630del278[4,5] | Truncation | 2544 | AT4LA | Carribean Black | Comp Htz |
| 7630del159[3] | Del, 53 aa | 2544 | F-2086 | Turkish | Compd Htz |
|  |  |  | AT13BER |  | Compd Htz |
| 7517del4 | Truncation | 2506 | AT43RM[10] | Italian | Hmz |
|  |  |  | At 59RM[10] | Italian | Hmz |
|  |  |  | AT102RM[10] | Italian | Hmz |
|  |  |  | At57RM[10] | Italian | Compd Htz |
|  |  |  | ATRM49B[10] | Italian | Compd Htz |
|  |  |  | ATRM22B[10] | Italian | Compd Htz |
| 6573del5 | Truncation | 2192 | AT12ABR | Australian | Compd Htz |
| 6348del105[3] | Del, 35 aa | 2116 | IARC15/AT4 | French | Hmz |
| 6199del149[3] | Truncation | 2067 | WG1101 | Canadian | Hmz |
| 5979del5 | Truncation | 1994 | AT104RM | Italian | Compd Htz |
| 5712insA | Truncation | 1905 | AT15LA | Philippino | Compd Htz |
| 5554insC | Truncation | 1852 | F-2079[9] | Turkish | Hmz |
| 5539del1 | Truncation | 1847 | AT2RO[9] | Arab | Hmz |
| 5320del1355[6] | Truncation | 1774 | ATRM49B | Italian | Compd Htz |
| 5320del7 | Truncation | 1774 | AT2SF | American | Compd Htz |
| 5178del142[3] | Truncation | 1727 | AT50RM | Italian | Compd Htz |
| 4612del165[3] | Del, 55 aa | 1538 | ATL105 | Japanese | Hmz |
| 44437del175[3] | Truncation | 1480 | AT29RM | Italian | Hmz |
| 4110del127[3] | Truncation | 1371 | AT2TAN[9] | Turkish | Hmz |
| 3403del174[3] | Del, 58 aa | 1135 | F-2095 | Turkish | Compd Htz |
| 2839del83[3] | Truncation | 947 | F-2080[9] | Turkish | Hmz |
|  |  |  | AT10TAN[9] | Turkish | Hmz |
| 2467del1372[3,5] | Del, 124 aa | 823 | AT6LA | English/Irish | Hmz |
| 2377del90[3] | Del, 30 aa | 793 | AT99RM[9] | Italian | Hmz |
| 22284delCT | Truncation | 762 | F-169[9] | Palestinian Arab | Hmz |
| 2125del125[3] | Truncation | 709 | F-2078[9] | Turkish | Hmz |
| 2113delT | Truncation | 705 | AT104RM | Italian | Compd Htz |
| 1563delAG[5] | Truncation | 522 | AT8LA[9] | Swiss/German | Hmz |
| 1339C->T | Arg->ter; truncation | 447 | F-2005[9] | Druze | Hmz |
| 1240C->T | Gln->ter; truncation | 414 | AT26RM | Italian | HMz |
| 755delGT | Truncation | 252 | AT24RM | Italian | Hmz |
| 497del7514[7] | Truncation | 166 | F-596[9] | Palestinian-Arab | Hmz |
| −30del215 | Incorrect initiation | 5′ UTR | F-303 | Bedouine | Hmz |
| In-frame genomic deletions and insertions: | | | | | |
| 8578del3 | Del, 1 aa | 2860 | AT3NG | Dutch | Compd Htz |
| 7636del9 | Del, 3 aa | 2547 | AT2BR | Caletic/Irish | Hmz |
|  |  |  | AT1ABR | Australian (Irish) | Hmz |
|  |  |  | AT1SF | American | Compd Htz |
| 7278del6[5] | Del, 2 aa | 2427 | AT5BI | Indian/English | Compd Htz |
|  |  |  | GM5823 | English | Compd Htz |
| 5319ins9 | Ind, 3 aa | 1774 | 251075-008T | Finnish | Compd Htz |
| Other base substitutions: | | | | | |
| 9170G->C | ter->Ser Extension of protein by 29 amino acids | ter | F-2089[9] | Turkish | Hmz |
| 8711A->G | Glu2904Gly | 2904 | AT41RM | Italian | Hmz |
| 27->C | Met->Thr Initiation codon abolished | 1 | AT8BI | British | Compd Htz |

[1]Presented according to the nomenclature proposed by Beaudet & Tsui (1993). Nucleotide numbers refer to their positions in the sequence of the ATM transcript (accession number U33841). The first nucleotide of the open reading frame was designated +1.
[2]Three adjacent exons skipped.
[3]One exon skipped.

TABLE 3-continued

Mutations in the ATM gene in patients with classical A–T.

| mRNA sequence change[1] | Predicted protein alteration | Codon[8] | Patient | Ethnic/ geographical origin | Genotype[11] |
| --- | --- | --- | --- | --- | --- |

[4]This allele produces two transcripts, woth one or two exons skipped.
[5]The same mutation was found in two affected siblings,
[6]Two exons skipped.
[7]This transcript is produced by an allele containing a large genomic deletion spanning approximately 85 Kb within the ATM gene in Family ISAT 9 (Savitsky, et. al., 1995a).
[8]For deletions, the number of the first codon on the amino terminus side is indicated. Codon numbers are according to the ATM protein sequence published by Savitsky at al. (1995b). In each section of the table, the mutations are ordered according to the codon numbers in this column, beginning with the one closest to the carboxyl terminus.
[9]Consanguineous family.
[10]All patients are from the same region.
[11]Genotypic combinations in which the mutation was found. Hmz: homozygote; Compd Htz: compound heteroxygote. Each patient represents one family.

REFERENCES

Aicardi et al., "Ataxia-ocularmotor apraxia: A syndrome mimicking ataxia-telangiectasia" Ann. Neurol. 24:497–502 (51988).

Aksentijevitch et al., "Familial mediterranean fever in Moroccan Jews: Demonstration of a founder effect by extended haplotype analysis" Am. J. Hum. Genet., 53:644–651 (1993).

Ambrose et al., "A physical map across chromosome 11q22–23 containing the major locus for ataxia-telangiectasia. Genomics, 21:612–619 (1994a).

Ambrose et al., 1994b. Structure and expression of the Huntington's disease gene: evidence against simple inactivation due to an expanded CAG repeat. Som. Cell Mol. Genet. 20:27–38.

Anderson and Kunkel, "The molecular and biochemical basis of Duchenne muscular dystrophy" Trends Biochem. Sci. 17:289–292 (1992).

Attree et al., "The Lowe's oculocerebrorenal syndrome gene encodes protein highly homologous to inositol polyphosphate-5-phosphatase" Nature, 358:239–242 (1992).

Ballabio et al., "Molecular heterogeneity of steroid sulfatase deficiency: a multicenter study on 57 unrelated patients, at DNA and protein levels" Genomics 4:36–40 (1989).

Barker, "A more robust, rapid alkaline denaturation sequencing method", BioTechniques, Vol. 14, No. 2, pp. 168–169 (1993).

Barnes, 1994. PCR amplification of up to 35-kb DNA with high fidelity and high yield from lambda bacteriophage templates. Proc. Natl. Acad. Sci. 91:2216–2220.

Berger et al., "Isolation of a candidate gene for Norrie disease by positional cloning" Nature Genet. 1:199–203, (1992)

Beaudet and Tsui, "A suggested nomenclature for designating mutations" Hum. Mutat. 2:245–248 (1993).

Broughton et al., "Mutations in the xeroderma pigmentosum group D DNA repair/transcription gene in patients with trichothiodystrophy" Nature Genet. 7:189–194 (1994).

Broughton et al., "Molecular and cellular analysis of the DNA repair defect in a patient in xeroderma pigmentosum group D who has the clinical features of xeroderma pigmentosum and Cockayne's syndrome" Am. J. Hum. Genet. 56:167–174 (1995).

Brown et al., "Control of p70 S6 kinase by kinase activity of FRAP in vivo" Nature 377:441–446 (1995).

Buckler et al., "Exon amplification: a strategy to isolate mammalian genes based on RNA splicing" Proc. Natl. Acad. Sci. USA, 88:4005–4009 (1991).

Burke and Olson, "Preparation of Clone Libraries in Yeast Artificial-Chromosome Vectors" in Methods in Enzymology, Vol. 194, "Guide to Yeast Genetics and Molecular Biology", eds. C. Guthrie and G. Fink, Academic Press, Inc., Chap. 17, pp. 251–270 (1991).

Byrne et al., "Ataxia-without-telangiectasia" J Neurol. Sci. 66:307–317 (1984).

Capecchi, "Altering the genome by homologous recombination" Science 244:1288–1292 (1989).

Chakravarti et al., "Nonuniform recombination within the human beta-globin gene cluster" Am. J. Hum. Genet., 36:1239–1258 (1984).

Chelly et al., "Isolation of a candidate gene for Menkes disease that encodes a potential heavy metal binding protein" Nature Genet. 3:14–19 (1993).

Cheng et al., 1994. Effective amplification of long targets from cloned inserts and human genomic DNA. Proc. Natl. Acad. Sci. 91:5695–5699.

Chessa et al., "Heterogeneity in ataxia telangiectasia: classical phenotype associated with intermediate cellular radiosensitivity" Am. J. Med. Genet. 42:741–746 (1992).

Chillon et al., "Mutations in the cystic fibrosis gene in patients with congenital absence of the vas deferens" New Engl. J. Med. 332:1475–1480 (1995).

Church et al., "Isolation of genes from complex sources of mammalian genomic DNA using exon amplification" Nature Genet. 6:98–104 (1993).

Church et al., 1994. Isolation of genes from complex sources of mammalian genomic DNA using exon amplification. Nature Genet. 6:98–94.

Collins, F. S. "Positional cloning: let's not call it reverse anymore" Nature Genet., 1:3–6 (1992).

Cooper and Krawczak, Human gene mutation. BIOS Scientific Publishers, London (1993).

Davies et al., "Targeted alterations in yeast artificial chromosomes for inter-species gene transfer", Nucleic Acids Research, Vol. 20, No. 11, pp. 2693–2698 (1992).

Derry et al., "WSP gene mutations in Wiskott-Aldrich syndrome and X-linked thrombocytopenia" Hum. Mol. Genet. 4:1127–1135 (1995).

Dickinson et al., "High frequency gene targeting using insertional vectors", Human Molecular Genetics, Vol. 2, No. 8, pp. 1299–1302 (1993).

Dietz and Kendzior, "Maintenance of an open reading frame as an additional level of scrutiny during splice site selection" Nature Genet. 8:183–188 (1994).

Duyk et al., "Exon trapping: A genetic screen to identify candidate transcribed sequences in cloned mammalian genomic DNA" Proc. Natl. Acad. Sci. USA, 87:8995–8999 (1990).

Fiorilli et al., "Variant of ataxia-telangiectasia with low-level radiosensitivity" *Hum. Genet.* 70:274–277 (1985).

Fodor et al, "Multiplexed biochemical assays with biological chips", *Nature* 364:555–556 (1993)

Foord and Rose, 1994. Long-distance PCR. PCR Methods Appl. 3:S149–S161.

Foroud et al. "Localization of the AT locus to an 8 cM interval defined by STMY and S132" *Am. J. Hum. Genet.*, 49:1263–1279 (1991).

Friedman and Weitberg, "Ataxia without telangiectasia" *Movement Disorders* 8:223–226 (1993).

Frohman, M. A. "On beyond classic RACE (rapid amplification of cDNA ends)" *PCR Methods and Applications*, 4:S40–S58 (1994).

Frohman et al., "Rapid production of full-length cDNAs from rare transcripts: Amplification using a single gene-specific oligonucleotide primer" *Proc. Natl. Acad. Sci. USA*, 85:8998–9002 (1988).

Gatti et al., "Genetic haplotyping of ataxia-telangiectasia families localizes the major gene to an 850 kb region on chromosome 11q23.1" *Int. J. Radiat. Biol.* (1994).

Gatti et al. "Localization of an ataxia-telangiectasia gene to chromosome 11q22–23" *Nature*, 336:577–580 (1988).

Gibson et al., "A nonsense mutation and exon skipping in the Fanconi anaemia group C gene" *Hum. Mol. Genet.* 2:797–799 (1993).

Gilboa et al. "Transfer and expression of cloned genes using retroviral vectors" *BioTechniques* 4(6):504–512 (1986).

Gottlieb and Jackson, "Protein kinases and DNA damage" *Trends Biochem. Sci.* 19:500–503 (1994).

Greenwell et al., "TEL1, a gene involved in controlling telomere length in *Saccharomyces cerevisiae*, is homologous to the human ataxia telangiectasia (ATM) gene" *Cell* 82:823–829 (1995).

Hastbacka et al., "Linkage disequilibrium mapping in isolated founder populations: diastrophic dysplasia in Finland" *Nature Genet.*, 2:204–211 (1992).

Harding, "Clinical features and classification of inherited ataxias" *Adv. Neurol.* 61:1–14 (1993).

Harnden, "The nature of ataxia-telangiectasia: problems and perspectives" *Int. J. Radiat. Biol.* 66:S13–S19 (1994).

Hogervorst et al., "Rapid detection of BRCA1 mutations by the protein truncation test" *Nature Genetics* 10:208–212 (1995).

Huxley et al., "The human HPRT gene on a yeast artificial chromosome is functional when transferred to mouse cells by cell fusion", *Genomics*, 9:742–750 (1991).

Jackson, 1991. A reappraisal of non-consensus mRNA splice sites. Nucleic Acids Res. 19:3795–3798.

Jakobovits et al., "Germ-line transmission and expression of a human-derived yeast artificial chromosome", *Nature*, Vol. 362, pp. 255–261 (1993).

James et al., *Nature Genet.* 8:70 (1994).

Jarvi et al., Cystic fibrosis transmembrane conductance regulator and obstructive azoospermia" *The Lancet* 345:1578 (1995).

Jaspers et al., *Cytogenet. Cell Genet.*, 49:259 (1988).

Kawasaki E. S. Amplification of RNA. In: PCR protocols: A Guide to Methods and Applications, Innis M. A., Gelfand D. H., Sninsky J. J., White T. J., eds. Academic Press, 1990, pp21–27.

Kerem et al., "Identification of the cystic fibrosis gene: genetic analysis" *Science*, 245:1073–1080 (1989).

Kolluri et al., "Identification of WASP mutations in patients with Wiskott-Aldrich syndrome and isolated thrombocytopenia reveals allelic heterogeneity at the WAS locus" *Hum. Mol. Genet.* 4:1119–1126 (1995).

Lamb et al., "Introduction and expression of the 400 kilobase precursor amyloid protein gene in transgenic mice", *Nature Genetics*, Vol. 5, pp. 22–29 (1993).

Lange et al., "Localization of an ataxia-telangiectasia gene to a 850 kb interval on chromosome 11q23.1 by linkage analysis of 176 families in an international consortium" *Am. J. Hum. Genet.* (1995).

Lehesjoki et al., "Localization of the EPM1 gene for progressive myoclonus epilepsy on chromosome 21: linkage disequilibrium allows high resolution mapping" *Hum. Mol. Genet.*, 2:1229–1234 (1993).

Lichter et al., "High-resolution mapping of human chromosome 11 by in situ hybridization with cosmid clones" *Science* 247:64–69 (1990).

Litt and Luty, "A hypervariable microsatellite revealed by in vitro amplification of a dinucleotide repeat within the cardiac muscle actin gene" *Am. J. Hum. Genet.*, 44:397–401 (1989).

Liu and Sommer, "Restriction endonuclease fingerprinting (REF): a sensitive method for screening mutations in long, contiguous segments of DNA" *BioTechniques* 18:470–477 (1995).

Llerena et al., "Spontaneous and induced chromosome breakage in chorionic villus samples: a cytogenetic approach to first trimester prenatal diagnosis of ataxia-telangiectasia syndrome" *J. Med. Genet.*, 26:174–178 (1989).

Lovett et al., *Proc. Natl. Acad. Sci. USA* 88, 9628 (1991)

Maserati et al., "Ataxia-without-telangiectasia in two sisters with rearrangements of chromosomes 7 and 14" *Clin. Genet.* 34:283–287 (1988).

McConville et al., "Genetic and physical mapping of the ataxia-telangiectasia locus on chromosome 11q22–23" *Int. J. Radiat. Biol.* (1994).

McConville et al., "Paired STSs amplified from radiation hybrids, and from associated YACs, identify highly polymorphic loci flanking the ataxia-telangiectasia locus on chromosome 11q22–23" *Hum. Mol. Genet.*, 2:969–974 (1993).

McConville et al., "Fine mapping of the chromosome 11q22–23 region using PFGE, linkage and haplotype analysis; localization of the gene for ataxia telangiectasia to a 5cM region flanked by NCAM/DRD2 and STMY/CJ52.75, phi2.22" *Nucleic Acids Res.*, 18:4335–4343 (1990).

Miki et al. "A strong candidate for the breast and ovarian cancer susceptibility gene BRCA1" *Science*, 266:66–71 (1994).

Mitchison et al., "Fine genetic mapping of the Batten Disease locus (CLN3) by haplotype analysis and demonstration of allelic association with chromosome 16p microsatellite loci" *Genomics*, 16:455–460 (1993).

Morgan et al., "The selective isolation of novel cDNAs encoded by the regions surrounding the human interleukin 4 and 5 genes" *Nucleic Acids Res.*, 20:5173–5179 (1992).

Nehls et al., 1994a. Exon amplification from complete libraries of genomic DNA using a novel phage vector with automatic plasmid excision facility: application to the mouse neurofibromatosis-1 locus. Oncogene 9:2169–2175.

Nehls et al., 1994b. The sequence complexity of exons trapped from the mouse genome. Current Biology 4:983–989.

Orita et al. Detection of polymorphisms of human DNA by gel electrophoresis as single-strand conformation polymorphisms. Proc Natl Acad Sci USA 1989; 86:2766–2770

Oskato et al., "Ataxia-telangiectasia: allelic association with 11q22–23 markers in Moroccan-Jewish patients. 43rd

*Annual Meeting of the American Society of Human Genetics*, New Orleans, La. (1993).

Ozelius et al., "Strong alleleic association between the torsion dystonia gene (DYT1) and loci on chromosome 9q34 in Ashkenazi Jews" *Am. J. Hum. Genet.* 50:619–628 (1992).

Parimoo et al., "cDNA selection: Efficient PCR approach for the selection of cDNAs encoded in large chromosomal DNA fragments" *Proc. Natl. Acad. Sci. USA,* 88:9623–9627 (1991).

Pease et al., "Light-generated oligonucleotide arrays for rapid DNA sequence analysis", *Proc. Natl. Acad. Sci. USA* 91(11):5022–5026 (1994)

Richard et al., *Genomics* 17, 1 (1993).

Roberts et al., 1993. Exon structure of the human dystrophin gene. Genomics 16:536–538.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Rotman et al., "Three dinucleotide repeat polymorphisms at the ataxia-telangiectasia locus" *Human Molecular Genetics* (1994b).

Rotman et al., "A YAC contig spanning the ataxia-telangiectasia locus (groups A and C) on chromosome 11q22-23. *Genomics* (1994c).

Rotman et al., "Physical and genetic mapping of the ATA/ ATC locus in chromosome 11q22-23" *Int. J. Radiat. Biol.* (1994d).

Rotman et al., "Rapid identification of polymorphic CA-repeats in YAC clones" *Molecular Biotechnology* (1995).

Savitsky et al., "A single gene with homologies to phosphatidylinositol 3-kinases and rad3+ is Mutated in all complementation groups of ataxia-telangiectasia" *Science,* 268:1749–1753 (Jun. 23, 1995a)

Savitsky et al., "The complete sequence of the coding region of the ATM gene reveals similarity to cell cycle regulators in different species" *Hum. Mol. Genet.* 4:2025–2032 (1995b).

Schedl et al., "A yeast artificial chromosome covering the tyrosinase gene confers copy number-dependent expression in transgenic mice", *Nature*, Vol. 362, pp. 258–261 (1993).

Sirugo et al., "Friedreich ataxia in Louisiana Acadians: Demonstration of a founder effect by analysis of microsatellite-generated extended haplotypes" *Am. J.Hum. Genet.,* 50:559–566 (1992).

Shiloh, "Ataxia-telangiectasia: closer to unraveling the mystery" *European Journal of Human Genetics* (1995) Shiloh et al., *Am. J. Hum. Genet.* 55 (suppl.), A49 (1994a)

Shiloh, et al., 1994b. Genetic, physical and functional analysis of the ataxia-telangiectasia locus on chromosome 11q22–23. 44th Annual Meeting of the American Society of Human Genetics, Montreal. Am. J. Hum. Genet. 55:A49.

Sommer, "Recent human germ-line mutation: Inferences from patients with hemophilia B" *Trends Gene.* 11:141–147 (1995).

Steingrimsdottir et al., "Mutations which alter splicing in the human hypoxanthine-guanine phosphoribosyl-transferase gene" *Nucleic Acids Res.* 6:1201–1208 (1992).

Strauss et al., "Germ line transmission of a yeast artificial chromosome spanning the murine $\alpha_1$ (I) collagen locus", *Science*, Vol. 259, pp. 1904–1907 (1993).

Tagle et al., "Magnetic capture of expressed sequences encoded within large genomic segments" *Nature,* 361:751–753 (1993).

Taylor et al., "Genetic and cellular features of ataxia telangiectasia" *Int. J. Radiat. Biol.* 65:65–70 (1994).

Taylor et al., Variant forms of ataxia telangiectasia. J. Med. Genet. 24, 669–677 (1987).

The European Polycystic Kidney Disease Consortium, "The polycystic kidney disease 1 gene encodes a 14 kb transcript and lies within a duplicated region on chromosome 16" *Cell,* 77:881–894 (1994).

The Huntington's Disease Collaborative Research Group, "A novel gene containing a trinucleotide repeat that is expanded and unstable on Huntington's disease chromosomes" *Cell,* 72:971–983 (1993).

Trofatter et al., "A novel moesin-, ezrin-, radixin-like gene is a candidate for the neurofibromatosis 2 tumor suppressor" *Cell,* 72:791–800 (1993).

Vanagaite et al., "Physical localization of microsatellite markers at the ataxia-telangiectasia locus at 11q22–23. *Genomics,* 22:231–233 (1994a).

Vanagaite et al., "High-density microsatellite map of ataxia-telangiectasia locus" *Human Genetics* 95:451–453 (1995).

Vetrie et al., "The gene involved in X-linked agammaglobulinemia is a member of the src family of protein-tyrosine kinases" *Nature,* 361:226–233 (1993).

Weber and May, "Abundant class of human DNA polymorphisms which can be typed using the polymerase chain reaction" *Am. J. Hum. Genet.,* 44:388–396 (1989).

Weemaes et al., "Nijmegen breakage syndrome: A progress report" *Int. J. Radiat. Biol.* 66:S185–S188 (1994).

Ying and Decoteau, "Cytogenetic anomalies in a patient with ataxia, immune deficiency, and high alpha-fetoprotein in the absence of telangiectasia" *Cancer Genet. Cytogenet.* 4:311–317 (1983).

Zakian, "ATM-related genes: What do they tell us about functions of the human gene?" *Cell* 82:685–687 (1995).

Ziv et al., "Ataxia-telangiectasia: linkage analysis in highly inbred Arab and Druze families and differentiation from an ataxia-microcephaly-cataract syndrome" *Hum. Genet.,* 88:619–626 (1992).

Ziv et al., "The ATC (ataxia-telangiectasia complementation group C) locus localizes to 11q22–q23. *Genomics,* 9:373–375 (1991).

Ziv et al., "Ataxia telangiectasia: a variant with altered in vitro phenotype of fibroblast cells" *Mutation Res.* 210:211–219 (1989).

I claim:

1. A purified, isolated and cloned nucleic acid sequence encoding a gene, designated ATM, which has a genomic organization as set forth in Table 1 (SEQ ID Nos:11–139) containing a mutation which results in protein truncation or no initiation and thereby Ataxia Telangiectasia.

2. A nucleic acid sequence as set forth in claim 1 having a cDNA sequence set forth in SEQ ID No:2 wherein an alternative spliced leader exon as set forth in SEQ ID No:10 is alternatively spliced.

3. A purified, isolated and cloned nucleic acid sequence according to claim 1 wherein the nucleic acid is mRNA.

4. The nucleic acid sequence of claim 1 wherein said mutation is selected from the group consisting of point mutations, deletions, insertions and rearrangements as set forth in Tables 2 and 3 such that the resulting sequence is altered imparting ataxia-telangiectasia.

5. The nucleic acid sequence of claim 4 wherein the mutation events are those set forth in Table 3.

6. A method of detecting a mRNA complementary to the nucleic acid sequence as set forth in claim 1 including the steps of:

isolating a specimen containing nucleic acid; and analyzing the specimen for partially complementary mRNA with an assay selected from the group consisting of in situ hybridization, Northern blotting and reverse transcriptase—polymerase chain reaction.

7. A method of detecting a nucleic acid sequence as set forth in claim 1 including the steps of:

isolating a specimen containing nucleic acid; and analyzing the specimen with an assay selected from the group consisting of in situ hybridization, Southern blotting, single strand conformational polymorphism, restriction endonuclease fingerprinting (REF), PCR amplification and DNA-chip analysis using nucleic acid sequence of claim 1.

8. A method of screening subjects with partial A-T phenotypes for ATM mutant genes including the steps of:

(a) isolating a specimen from a subject with a partial A-T phenotype; and (b) assaying the specimen for mutations of the ATM gene wherein a nucleic acid sequence of claim 1 is identified by restriction endonuclease fingerprinting (REF).

9. The nucleic acid sequence of claim 1 wherein a mutation event selected from the group consisting of point mutations, deletions and insertions has occurred such that the resulting amino acid sequence is truncated or no initiation occurs.

* * * * *

SEQUENCE LISTING ( 1 ) GENERAL INFORMATION:

( i i i ) NUMBER OF SEQUENCES: 139

( 2 ) INFORMATION FOR SEQ ID NO:1:

( i ) SEQUENCE CHARACTERISTICS:
        ( A ) LENGTH: 5912 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: 7-9

( x i ) SEQUENCE DESCRIPTION: SEQ ID NO:1:

```
CATACTTTTT  CCTCTTAGTC  TACAGGTTGG  CTGCATAGAA  GAAAAAGGTA  GAGTTATTTA      60
TAATCTTGTA  AATCTTGGAC  TTTGAGTCAT  CTATTTTCTT  TTACAGTCAT  CGAATACTTT     120
TGGAAATAAG  GTAATATATG  CCTTTTGAGC  TGTCTTGACG  TTCACAGATA  TAAAATATTA     180
AATATATTTT  AATTTTGTGC  CCTTGCAGAT  TGATCACTTA  TTCATTAGTA  ATTTACCAGA     240
GATTGTGGTG  GAGTTATTGA  TGACGTTACA  TGAGCCAGCA  AATTCTAGTG  CCAGTCAGAG     300
CACTGACCTC  TGTGACTTTT  CAGGGGATTT  GGATCCTGCT  CCTAATCCAC  CTCATTTTCC     360
ATCGCATGTG  ATTAAAGCAA  CATTTGCCTA  TATCAGCAAT  TGTCATAAAA  CCAAGTTAAA     420
AAGCATTTTA  GAAATTCTTT  CCAAAAGCCC  TGATTCCTAT  CAGAAAATTC  TTCTTGCCAT     480
ATGTGAGCAA  GCAGCTGAAA  CAAATAATGT  TTATAAGAAG  CACAGAATTC  TTAAAATATA     540
TCACCTGTTT  GTTAGTTTAT  TACTGAAAGA  TATAAAAAGT  GGCTTAGGAG  GAGCTTGGGC     600
CTTTGTTCTT  CGAGACGTTA  TTTATACTTT  GATTCACTAT  ATCAACCAAA  GGCCTTCTTG     660
TATCATGGAT  GTGTCATTAC  GTAGCTTCTC  CCTTTGTTGT  GACTTATTAA  GTCAGGTTTG     720
CCAGACAGCC  GTGACTTACT  GTAAGGATGC  TCTAGAAAAC  CATCTTCATG  TTATTGTTGG     780
TACACTTATA  CCCCTTGTGT  ATGAGCAGGT  GGAGGTTCAG  AAACAGGTAT  GGACTTGTT      840
GAAATACTTA  GTGATAGATA  ACAAGGATAA  TGAAAACCTC  TATATCACGA  TTAAGCTTTT     900
AGATCCTTTT  CCTGACCATG  TTGTTTTTAA  GGATTTGCGT  ATTACTCAGC  AAAAAAATCAA    960
ATACAGTAGA  GGACCCTTTT  CACTCTTGGA  GGAAATTAAC  CATTTCTCT   CAGTAAGTGT    1020
TTATGATGCA  CTTCCATTGA  CAAGACTTGA  AGGACTAAAG  GATCTTCGAA  GACAACTGGA   1080
ACTACATAAA  GATCAGATGG  TGGACATTAT  GAGAGCTTCT  CAGGATAATC  CGCAAGATGG   1140
GATTATGGTG  AAACTAGTTG  TCAATTTGTT  GCAGTTATCC  AAGATGGCAA  TAAACCACAC   1200
TGGTGAAAAA  GAAGTTCTAG  AGGCTGTTGG  AAGCTGCTTG  GGAGAAGTGG  GTCCTATAGA   1260
TTTCTCTACC  ATAGCTATAC  AACATAGTAA  AGATGCATCT  TATACCAAGG  CCCTTAAGTT   1320
ATTTGAAGAT  AAAGAACTTC  AGTGGACCTT  CATAATGCTG  ACCTACCTGA  ATAACACACT   1380
GGTAGAAGAT  TGTGTCAAAG  TTCGATCAGC  AGCTGTTACC  TGTTTGAAAA  ACATTTTAGC   1440
CACAAAGACT  GGACATAGTT  TCTGGGAGAT  TTATAAGATG  ACAACAGATC  CAATGCTGGC   1500
CTATCTACAG  CCTTTTAGAA  CATCAAGAAA  AAAGTTTTTA  GAAGTACCCA  GATTTGACAA   1560
AGAAAACCCT  TTTGAAGGCC  TGGATGATAT  AAATCTGTGG  ATTCCTCTAA  GTGAAAATCA   1620
TGACATTTGG  ATAAAGACAC  TGACTTGTGC  TTTTTTGGAC  AGTGGAGGCA  CAAAATGTGA   1680
AATTCTTCAA  TTATTAAAGC  CAATGTGTGA  AGTGAAAACT  GACTTTTGTC  AGACTGTACT   1740
TCCATACTTG  ATTCATGATA  TTTTACTCCA  AGATACAAAT  GAATCATGGA  GAAATCTGCT   1800
TTCTACACAT  GTTCAGGGAT  TTTTCACCAG  CTGTCTTCGA  CACTTCTCGC  AAACGAGCCG   1860
ATCCACAACC  CCTGCAAACT  GGATTCAGA   GTCAGAGCAC  TTTTTCCGAT  GCTGTTTGGA   1920
TAAAAAAATCA  CAAAGAACAA  TGCTTGCTGT  TGTGGACTAC  ATGAGAAGAC  AAAAGAGACC   1980
```

```
TTCTTCAGGA ACAATTTTTA ATGATGCTTT CTGGCTGGAT TTAAATTATC TAGAAGTTGC    2040
CAAGGTAGCT CAGTCTTGTG CTGCTCACTT TACAGCTTTA CTCTATGCAG AAATCTATGC    2100
AGATAAGAAA AGTATGGATG ATCAAGAGAA AAGAAGTCTT GCATTTGAAG AAGGAAGCCA    2160
GAGTACAACT ATTTCTAGCT TGAGTGAAAA AGTAAAGAA GAAACTGGAA TAAGTTTACA    2220
GGATCTTCTC TTAGAAATCT ACAGAAGTAT AGGGGAGCCA GATAGTTTGT ATGGCTGTGG    2280
TGGAGGGAAG ATGTTACAAC CCATTACTAG ACTACGAACA TATGAACACG AAGCAATGTG    2340
GGGCAAAGCC CTAGTAACAT ATGACCTCGA AACAGCAATC CCTCATCAA CACGCCAGGC    2400
AGGAATCATT CAGGCCTTGC AGAATTTGGG ACTCTGCCAT ATTCTTTCCG TCTATTTAAA    2460
AGGATTGGAT TATGAAAATA AAGACTGGTG TCCTGAACTA GAAGAACTTC ATTACCAAGC    2520
AGCATGGAGG AATATGCAGT GGGACCATTG CACTTCCGTC AGCAAGAAG TAGAAGGAAC    2580
CAGTTACCAT GAATCATTGT ACAATGCTCT ACAATCTCTA AGAGACAGAG AATTCTCTAC    2640
ATTTTATGAA AGTCTCAAAT ATGCCAGAGT AAAAGAAGTG GAAGAGATGT GTAAGCGCAG    2700
CCTTGAGTCT GTGTATTCGC TCTATCCAC ACTTAGCAGG TTGCAGGCCA TTGGAGAGCT    2760
GGAAAGCATT GGGGAGCTTT TCTCAAGATC AGTCACACAT AGACAACTCT CTGAAGTATA    2820
TATTAAGTGG CAGAAACACT CCCAGCTTCT CAAGGACAGT GATTTTAGTT TTCAGGAGCC    2880
TATCATGGCT CTACGCACAG TCATTTTGGA GATCCTGATG GAAAAGGAAA TGGACAACTC    2940
ACAAAGAGAA TGTATTAAGG ACATTCTCAC CAAACACCTT GTAGAACTCT CTATACTGGC    3000
CAGAACTTTC AAGAACACTC AGCTCCCTGA AAGGGCAATA TTTCAAATTA AACAGTACAA    3060
TTCAGTTAGC TGTGGAGTCT CTGAGTGGCA GCTGGAAGAA GCACAAGTAT CTGGGCAAA    3120
AAAGGAGCAG AGTCTTGCCC TGAGTATTCT CAAGCAAATG ATCAAGAAGT GGATGCCAG    3180
CTGTGCAGCG AACAATCCCA GCCTAAAACT TACATACACA GAATGTCTGA GGGTTTGTGG    3240
CAACTGGTTA GCAGAAACGT GCTTAGAAAA TCCTGCGGTC ATCATGCAGA CCTATCTAGA    3300
AAAGGCAGTA GAAGTTGCTG GAAATTATGA TGGAGAAAGT AGTGATGAGC TAAGAAATGG    3360
AAAAATGAAG GCATTTCTCT CATTAGCCCG GTTTTCAGAT ACTCAATACC AAAGAATTGA    3420
AAACTACATG AAATCATCGG AATTTGAAAA CAAGCAAGCT CTCCTGAAAA GAGCCAAAGA    3480
GGAAGTAGGT CTCCTTAGGG AACATAAAAT TCAGACAAAC AGATACACAG TAAAGGTTCA    3540
GCGAGAGCTG GAGTTGGATG AATTAGCCCT GCGTGCACTG AAAGAGGATC GTAAACGCTT    3600
CTTATGTAAA GCAGTTGAAA ATTATATCAA CTGCTTATTA AGTGGAGAAG AACATGATAT    3660
GTGGGTATTC CGACTTTGTT CCCTCTGGCT TGAAAATTCT GGAGTTTCTG AAGTCAATGG    3720
CATGATGAAG AGAGACGGAA TGAAGATTCC AACATATAAA TTTTTGCCTC TTATGTACCA    3780
ATTGGCTGCT AGAATGGGGA CCAAGATGAT GGGAGGCCTA GGATTTCATG AAGTCCTCAA    3840
TAATCTAATC TCTAGAATTT CAATGGATCA CCCCCATCAC ACTTTGTTTA TTATACTGGC    3900
CTTAGCAAAT GCAAACAGAG ATGAATTTCT GACTAAACCA GAGGTAGCCA GAAGAAGCAG    3960
AATAACTAAA AATGTGCCTA ACAAAGCTC TCAGCTTGAT GAGGATCGAA CAGAGGCTGC    4020
AAATAGAATA ATATGTACTA TCAGAAGTAG GAGACCTCAG ATGGTCAGAA GTGTTGAGGC    4080
ACTTTGTGAT GCTTATATTA TATTAGCAAA CTTAGATGCC ACTCAGTGGA AGACTCAGAG    4140
AAAAGGCATA AATATTCCAG CAGACCAGCC AATTACTAAA CTTAAGAATT TAGAAGATGT    4200
TGTTGTCCCT ACTATGGAAA TTAAGGTGGA CCACACAGGA GAATATGGAA ATCTGGTGAC    4260
TATACAGTCA TTTAAAGCAG AATTTCGCTT AGCAGGAGGT GTAAATTTAC CAAAAATAAT    4320
AGATTGTGTA GGTTCCGATG GCAAGGAGAG GAGACAGCTT GTTAAGGGCC GTGATGACCT    4380
```

| | | | | | | |
|---|---|---|---|---|---|---|
| GAGACAAGAT | GCTGTCATGC | AACAGGTCTT | CCAGATGTGT | AATACATTAC | TGCAGAGAAA | 4440 |
| CACGGAAACT | AGGAAGAGGA | AATTAACTAT | CTGTACTTAT | AAGGTGGTTC | CCCTCTCTCA | 4500 |
| GCGAAGTGGT | GTTCTTGAAT | GGTGCACAGG | AACTGTCCCC | ATTGGTGAAT | TTCTTGTTAA | 4560 |
| CAATGAAGAT | GGTGCTCATA | AAGATACAG | GCCAAATGAT | TTCAGTGCCT | TTCAGTGCCA | 4620 |
| AAAGAAAATG | ATGGAGGTGC | AAAAAAAGTC | TTTTGAAGAG | AAATATGAAG | TCTTCATGGA | 4680 |
| TGTTTGCCAA | AATTTTCAAC | CAGTTTTCCG | TTACTTCTGC | ATGGAAAAAT | TCTTGGATCC | 4740 |
| AGCTATTTGG | TTTGAGAAGC | GATTGGCTTA | TACGCGCAGT | GTAGCTACTT | CTTCTATTGT | 4800 |
| TGGTTACATA | CTTGGACTTG | GTGATAGACA | TGTACAGAAT | ATCTTGATAA | ATGAGCAGTC | 4860 |
| AGCAGAACTT | GTACATATAG | ATCTAGGTGT | TGCTTTTGAA | CAGGGCAAAA | TCCTTCCTAC | 4920 |
| TCCTGAGACA | GTTCCTTTTA | GACTCACCAG | AGATATTGTG | GATGGCATGG | GCATTACGGG | 4980 |
| TGTTGAAGGT | GTCTTCAGAA | GATGCTGTGA | GAAAACCATG | GAAGTGATGA | GAAACTCTCA | 5040 |
| GGAAACTCTG | TTAACCATTG | TAGAGGTCCT | TCTATATGAT | CCACTCTTTG | ACTGGACCAT | 5100 |
| GAATCCTTTG | AAAGCTTTGT | ATTTACAGCA | GAGGCCGGAA | GATGAAACTG | AGCTTCACCC | 5160 |
| TACTCTGAAT | GCAGATGACC | AAGAATGCAA | ACGAAATCTC | AGTGATATTG | ACCAGAGTTT | 5220 |
| CGACAAAGTA | GCTGAACGTG | TCTTAATGAG | ACTACAAGAG | AAACTGAAAG | GAGTGGAAGA | 5280 |
| AGGCACTGTG | CTCAGTGTTG | GTGGACAGGT | GAATTTGCTC | ATACAGCAGG | CCATAGACCC | 5340 |
| CAAAAATCTC | AGCCGACTTT | TCCCAGGATG | GAAAGCTTGG | GTGTGATCTT | CAGTATATGA | 5400 |
| ATTACCCTTT | CATTCAGCCT | TTAGAAATTA | TATTTTAGCC | TTTATTTTA | ACCTGCCAAC | 5460 |
| ATACTTTAAG | TAGGGATTAA | TATTTAAGTG | AACTATTGTG | GGTTTTTTG | AATGTTGGTT | 5520 |
| TTAATACTTG | ATTTAATCAC | CACTCAAAAA | TGTTTTGATG | GTCTTAAGGA | ACATCTCTGC | 5580 |
| TTTCACTCTT | TAGAAATAAT | GGTCATTCGG | GCTGGGCGCA | GCGGCTCACG | CCTGTAATCC | 5640 |
| CAGCACTTTG | GGAGGCCGAG | GTGAGCGGAT | CACAAGGTCA | GGAGTTCGAG | ACCAGCCTGG | 5700 |
| CCAAGAGACC | AGCCTGGCCA | GTATGGTGAA | ACCCTGTCTC | TACTAAAAAT | ACAAAAATTA | 5760 |
| GCCGAGCATG | GTGGCGGGCA | CCTGTAGTCC | CAGCTACTCG | AGAGGCTGAG | GCAGGAGAAT | 5820 |
| CTCTTGAACC | TGGGAGGTGA | AGGTTGCTGT | GGGCCAAAAT | CATGCCATTG | CACTCCAGCC | 5880 |
| TGGGTGACAA | GAGCGAAACT | CCATCTCAAA | AA | | | 5912 |

(2) INFORMATION FOR SEQ ID NO:2:

(i) SEQUENCE CHARACTERISTICS:
        (A) LENGTH: 9171 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (viii) POSITION IN GENOME:
        (A) CHROMOSOME/SEGMENT: 11q22-23

(xi) SEQUENCE DESCRIPTION: SEQ ID NO:2:

| | | | | | | |
|---|---|---|---|---|---|---|
| ATGAGTCTAG | TACTTAATGA | TCTGCTTATC | TGCTGCCGTC | AACTAGAACA | TGATAGAGCT | 60 |
| ACAGAACGAA | AGAAAGAAGT | TGAGAAATTT | AAGCGCCTGA | TTCGAGATCC | TGAAACAATT | 120 |
| AAACATCTAG | ATCGGCATTC | AGATTCCAAA | CAAGGAAAAT | ATTTGAATTG | GGATGCTGTT | 180 |
| TTTAGATTTT | TACAGAAATA | TATTCAGAAA | GAAACAGAAT | GTCTGAGAAT | AGCAAAACCA | 240 |

-continued

```
AATGTATCAG CCTCAACACA AGCCTCCAGG CAGAAAAAGA TGCAGGAAAT CAGTAGTTTG    300
GTCAAATACT TCATCAAATG TGCAAACAGA AGAGCACCTA GGCTAAAATG TCAAGAACTC    360
TTAAATTATA TCATGGATAC AGTGAAAGAT TCATCTAATG GTGCTATTTA CGGAGCTGAT    420
TGTAGCAACA TACTACTCAA AGACATTCTT TCTGTGAGAA AATACTGGTG TGAAATATCT    480
CAGCAACAGT GGTTAGAATT GTTCTCTGTG TACTTCAGGC TCTATCTGAA ACCTTCACAA    540
GATGTTCATA GAGTTTTAGT GGCTAGAATA ATTCATGCTG TTACCAAAGG ATGCTGTTCT    600
CAGACTGACG GATTAAATTC CAAATTTTTG GACTTTTTTT CCAAGGCTAT TCAGTGTGCG    660
AGACAAGAAA AGAGCTCTTC AGGTCTAAAT CATATCTTAG CAGCTCTTAC TATCTTCCTC    720
AAGACTTTGG CTGTCAACTT TCGAATTCGA GTGTGTGAAT TAGGAGATGA AATTCTTCCC    780
ACTTTGCTTT ATATTTGGAC TCAACATAGG CTTAATGATT CTTTAAAAGA AGTCATTATT    840
GAATTATTTC AACTGCAAAT TTATATCCAT CATCCGAAAG GAGCCAAAAC CCAAGAAAAA    900
GGTGCTTATG AATCAACAAA ATGGAGAAGT ATTTTATACA ACTTATATGA TCTGCTAGTG    960
AATGAGATAA GTCATATAGG AAGTAGAGGA AAGTATTCTT CAGGATTTCG TAATATTGCC   1020
GTCAAAGAAA ATTTGATTGA ATTGATGGCA GATATCTGTC ACCAGGTTTT TAATGAAGAT   1080
ACCAGATCCT TGGAGATTTC TCAATCTTAC ACTACTACAC AAAGAGAATC TAGTGATTAC   1140
AGTGTCCCTT GCAAAAGGAA GAAAATAGAA CTAGGCTGGG AAGTAATAAA AGATCACCTT   1200
CAGAAGTCAC AGAATGATTT TGATCTTGTG CCTTGGCTAC AGATTGCAAC CCAATTAATA   1260
TCAAAGTATC CTGCAAGTTT ACCTAACTGT GAGCTGTCTC CATTACTGAT GATACTATCT   1320
CAGCTTCTAC CCCAACAGCG ACATGGGGAA CGTACACCAT ATGTGTTACG ATGCCTTACG   1380
GAAGTTGCAT TGTGTCAAGA CAAGAGGTCA AACCTAGAAA GCTCACAAAA GTCAGATTTA   1440
TTAAAACTCT GGAATAAAAT TTGGTGTATT ACCTTTCGTG GTATAAGTTC TGAGCAAATA   1500
CAAGCTGAAA ACTTTGGCTT ACTTGGAGCC ATAATTCAGG GTAGTTTAGT TGAGGTTGAC   1560
AGAGAATTCT GGAAGTTATT TACTGGGTCA GCCTGCAGAC CTTCATGTCC TGCAGTATGC   1620
TGTTTGACTT TGGCACTGAC CACCAGTATA GTTCCAGGAA CGGTAAAAAT GGGAATAGAG   1680
CAAAATATGT GTGAAGTAAA TAGAAGCTTT TCTTTAAAGG AATCAATAAT GAAATGGCTC   1740
TTATTCTATC AGTTAGAGGG TGACTTAGAA AATAGCACAG AAGTGCCTCC AATTCTTCAC   1800
AGTAATTTTC CTCATCTTGT ACTGGAGAAA ATTCTTGTGA GTCTCACTAT GAAAAACTGT   1860
AAAGCTGCAA TGAATTTTTT CCAAAGCGTG CCAGAATGTG AACACCACCA AAAAGATAAA   1920
GAAGAACTTT CATTCTCAGA AGTAGAAGAA CTATTTCTTC AGACAACTTT TGACAAGATG   1980
GACTTTTTAA CCATTGTGAG AGAATGTGGT ATAGAAAAGC ACCAGTCCAG TATTGGCTTC   2040
TCTGTCCACC AGAATCTCAA GGAATCACTG GATCGCTGTC TTCTGGGATT ATCAGAACAG   2100
CTTCTGAATA ATTACTCATC TGAGATTACA AATTCAGAAA CTCTTGTCCG GTGTTCACGT   2160
CTTTTGGTGG GTGTCCTTGG CTGCTACTGT TACATGGGTG TAATAGCTGA AGAGGAAGCA   2220
TATAAGTCAG AATTATTCCA GAAAGCCAAG TCTCTAATGC AATGTGCAGG AGAAAGTATC   2280
ACTCTGTTTA AAAATAAGAC AAATGAGGAA TTCAGAATTG GTTCCTTGAG AAATATGATG   2340
CAGCTATGTA CACGTTGCTT GAGCAACTGT ACCAAGAAGA GTCCAAATAA GATTGCATCT   2400
GGCTTTTTCC TGCGATTGTT AACATCAAAG CTAATGAATG ACATTGCAGA TATTTGTAAA   2460
AGTTTAGCAT CCTTCATCAA AAAGCCATTT GACCGTGGAG AAGTAGAATC AATGGAAGAT   2520
GATACTAATG GAAATCTAAT GGAGGTGGAG GATCAGTCAT CCATGAATCT ATTTAACGAT   2580
TACCCTGATA GTAGTGTTAG TGATGCAAAC GAACCTGGAG AGAGCCAAAG TACCATAGGT   2640
```

```
GCCATTAATC  CTTTAGCTGA  AGAATATCTG  TCAAAGCAAG  ATCTACTTTT  CTTAGACATG  2700

CTCAAGTTCT  TGTGTTTGTG  TGTAACTACT  GCTCAGACCA  ATACTGTGTC  CTTTAGGGCA  2760

GCTGATATTC  GGAGGAAATT  GTTAATGTTA  ATTGATTCTA  GCACGCTAGA  ACCTACCAAA  2820

TCCCTCCACC  TGCATATGTA  TCTAATGCTT  TTAAAGGAGC  TTCCTGGAGA  AGAGTACCCC  2880

TTGCCAATGG  AAGATGTTCT  TGAACTTCTG  AAACCACTAT  CCAATGTGTG  TTCTTTGTAT  2940

CGTCGTGACC  AAGATGTTTG  TAAAACTATT  TTAAACCATG  TCCTTCATGT  AGTGAAAAAC  3000

CTAGGTCAAA  GCAATATGGA  CTCTGAGAAC  ACAAGGGATG  CTCAAGGACA  GTTTCTTACA  3060

GTAATTGGAG  CATTTTGGCA  TCTAACAAAG  GAGAGGAAAT  ATATATTCTC  TGTAAGAATG  3120

GCCCTAGTAA  ATTGCCTTAA  AACTTTGCTT  GAGGCTGATC  CTTATTCAAA  ATGGGCCATT  3180

CTTAATGTAA  TGGGAAAAGA  CTTTCCTGTA  AATGAAGTAT  TTACACAATT  TCTTGCTGAC  3240

AATCATCACC  AAGTTCGCAT  GTTGGCTGCA  GAGTCAATCA  ATAGATTGTT  CCAGGACACG  3300

AAGGGAGATT  CTTCCAGGTT  ACTGAAAGCA  CTTCCTTTGA  AGCTTCAGCA  AACAGCTTTT  3360

GAAAATGCAT  ACTTGAAAGC  TCAGGAAGGA  ATGAGAGAAA  TGTCCCATAG  TGCTGAGAAC  3420

CCTGAAACTT  TGGATGAAAT  TTATAATAGA  AAATCTGTTT  TACTGACGTT  GATAGCTGTG  3480

GTTTTATCCT  GTAGCCCTAT  CTGCGAAAAA  CAGGCTTTGT  TGCCCTGTG   TAAATCTGTG  3540

AAAGAGAATG  GATTAGAACC  TCACCTTGTG  AAAAAGGTTT  TAGAGAAAGT  TTCTGAAACT  3600

TTTGGATATA  GACGTTTAGA  AGACTTTATG  GCATCTCATT  TAGATTATCT  GGTTTTGGAA  3660

TGGCTAAATC  TTCAAGATAC  TGAATACAAC  TTATCTTCTT  TTCCTTTTAT  TTTATTAAAC  3720

TACACAAATA  TTGAGGATTT  CTATAGATCT  TGTTATAAGG  TTTTGATTCC  ACATCTGGTG  3780

ATTAGAAGTC  ATTTTGATGA  GGTGAAGTCC  ATTGCTAATC  AGATTCAAGA  GGACTGGAAA  3840

AGTCTTCTAA  CAGACTGCTT  TCCAAAGATT  CTTGTAAATA  TTCTTCCTTA  TTTTGCCTAT  3900

GAGGGTACCA  GAGACAGTGG  GATGGCACAG  CAAAGAGAGA  CTGCTACCAA  GGTCTATGAT  3960

ATGCTTAAAA  GTGAAAACTT  ATTGGGAAAA  CAGATTGATC  ACTTATTCAT  TAGTAATTTA  4020

CCAGAGATTG  TGGTGGAGTT  ATTGATGACG  TTACATGAGC  CAGCAAATTC  TAGTGCCAGT  4080

CAGAGCACTG  ACCTCTGTGA  CTTTTCAGGG  GATTTGGATC  CTGCTCCTAA  TCCACCTCAT  4140

TTTCCATCGC  ATGTGATTAA  AGCAACATTT  GCCTATATCA  GCAATTGTCA  TAAAACCAAG  4200

TTAAAAAGCA  TTTTAGAAAT  TCTTTCCAAA  AGCCCTGATT  CCTATCAGAA  AATTCTTCTT  4260

GCCATATGTG  AGCAAGCAGC  TGAAACAAAT  AATGTTTATA  AGAAGCACAG  AATTCTTAAA  4320

ATATATCACC  TGTTTGTTAG  TTTATTACTG  AAAGATATAA  AAAGTGGCTT  AGGAGGAGCT  4380

TGGGCCTTTG  TTCTTCGAGA  CGTTATTTAT  ACTTTGATTC  ACTATATCAA  CCAAGGCCT   4440

TCTTGTATCA  TGGATGTGTC  ATTACGTAGC  TTCTCCCTTT  GTTGTGACTT  ATTAAGTCAG  4500

GTTTGCCAGA  CAGCCGTGAC  TTACTGTAAG  GATGCTCTAG  AAAACCATCT  TCATGTTATT  4560

GTTGGTACAC  TTATACCCCT  TGTGTATGAG  CAGGTGGAGG  TTCAGAAACA  GGTATTGGAC  4620

TTGTTGAAAT  ACTTAGTGAT  AGATAACAAG  GATAATGAAA  ACCTCTATAT  CACGATTAAG  4680

CTTTTAGATC  CTTTTCCTGA  CCATGTTGTT  TTTAAGGATT  TGCGTATTAC  TCAGCAAAAA  4740

ATCAAATACA  GTAGAGGACC  CTTTTCACTC  TTGGAGGAAA  TTAACCATTT  TCTCTCAGTA  4800

AGTGTTTATG  ATGCACTTCC  ATTGACAAGA  CTTGAAGGAC  TAAAGGATCT  TCGAAGACAA  4860

CTGGAACTAC  ATAAAGATCA  GATGGTGGAC  ATTATGAGAG  CTTCTCAGGA  TAATCCGCAA  4920

GATGGGATTA  TGGTGAAACT  AGTTGTCAAT  TTGTTGCAGT  TATCCAAGAT  GGCAATAAAC  4980

CACACTGGTG  AAAAAGAAGT  TCTAGAGGCT  GTTGGAAGCT  GCTTGGGAGA  AGTGGGTCCT  5040
```

| | | | | | | |
|---|---|---|---|---|---|---|
| ATAGATTTCT | CTACCATAGC | TATACAACAT | AGTAAAGATG | CATCTTATAC | CAAGGCCCTT | 5100 |
| AAGTTATTTG | AAGATAAAGA | ACTTCAGTGG | ACCTTCATAA | TGCTGACCTA | CCTGAATAAC | 5160 |
| ACACTGGTAG | AAGATTGTGT | CAAAGTTCGA | TCAGCAGCTG | TTACCTGTTT | GAAAAACATT | 5220 |
| TTAGCCACAA | AGACTGGACA | TAGTTTCTGG | GAGATTTATA | AGATGACAAC | AGATCCAATG | 5280 |
| CTGGCCTATC | TACAGCCTTT | TAGAACATCA | AGAAAAAGT | TTTTAGAAGT | ACCCAGATTT | 5340 |
| GACAAAGAAA | ACCCTTTTGA | AGGCCTGGAT | GATATAAATC | TGTGGATTCC | TCTAAGTGAA | 5400 |
| AATCATGACA | TTTGGATAAA | GACACTGACT | TGTGCTTTTT | TGGACAGTGG | AGGCACAAAA | 5460 |
| TGTGAAATTC | TTCAATTATT | AAAGCCAATG | TGTGAAGTGA | AAACTGACTT | TTGTCAGACT | 5520 |
| GTACTTCCAT | ACTTGATTCA | TGATATTTTA | CTCCAAGATA | CAAATGAATC | ATGGAGAAAT | 5580 |
| CTGCTTTCTA | CACATGTTCA | GGGATTTTTC | ACCAGCTGTC | TTCGACACTT | CTCGCAAACG | 5640 |
| AGCCGATCCA | CAACCCCTGC | AAACTTGGAT | TCAGAGTCAG | AGCACTTTTT | CCGATGCTGT | 5700 |
| TTGGATAAAA | AATCACAAAG | AACAATGCTT | GCTGTTGTGG | ACTACATGAG | AAGACAAAAG | 5760 |
| AGACCTTCTT | CAGGAACAAT | TTTTAATGAT | GCTTTCTGGC | TGGATTTAAA | TTATCTAGAA | 5820 |
| GTTGCCAAGG | TAGCTCAGTC | TTGTGCTGCT | CACTTTACAG | CTTTACTCTA | TGCAGAAATC | 5880 |
| TATGCAGATA | AGAAAAGTAT | GGATGATCAA | GAGAAAAGAA | GTCTTGCATT | TGAAGAAGGA | 5940 |
| AGCCAGAGTA | CAACTATTTC | TAGCTTGAGT | GAAAAAGTA | AAGAAGAAAC | TGGAATAAGT | 6000 |
| TTACAGGATC | TTCTCTTAGA | AATCTACAGA | AGTATAGGGG | AGCCAGATAG | TTTGTATGGC | 6060 |
| TGTGGTGGAG | GGAAGATGTT | ACAACCCATT | ACTAGACTAC | GAACATATGA | ACACGAAGCA | 6120 |
| ATGTGGGGCA | AAGCCCTAGT | AACATATGAC | CTCGAAACAG | CAATCCCCTC | ATCAACACGC | 6180 |
| CAGGCAGGAA | TCATTCAGGC | CTTGCAGAAT | TTGGGACTCT | GCCATATTCT | TTCCGTCTAT | 6240 |
| TTAAAAGGAT | TGGATTATGA | AAATAAAGAC | TGGTGTCCTG | AACTAGAAGA | ACTTCATTAC | 6300 |
| CAAGCAGCAT | GGAGGAATAT | GCAGTGGGAC | CATTGCACTT | CCGTCAGCAA | AGAAGTAGAA | 6360 |
| GGAACCAGTT | ACCATGAATC | ATTGTACAAT | GCTCTACAAT | CTCTAAGAGA | CAGAGAATTC | 6420 |
| TCTACATTTT | ATGAAAGTCT | CAAATATGCC | AGAGTAAAAG | AAGTGGAAGA | GATGTGTAAG | 6480 |
| CGCAGCCTTG | AGTCTGTGTA | TTCGCTCTAT | CCCACACTTA | GCAGGTTGCA | GGCCATTGGA | 6540 |
| GAGCTGGAAA | GCATTGGGGA | GCTTTTCTCA | AGATCAGTCA | CACATAGACA | ACTCTCTGAA | 6600 |
| GTATATATTA | AGTGGCAGAA | ACACTCCCAG | CTTCTCAAGG | ACAGTGATTT | TAGTTTTCAG | 6660 |
| GAGCCTATCA | TGGCTCTACG | CACAGTCATT | TTGGAGATCC | TGATGGAAAA | GGAAATGGAC | 6720 |
| AACTCACAAA | GAGAATGTAT | TAAGGACATT | CTCACCAAAC | ACCTTGTAGA | ACTCTCTATA | 6780 |
| CTGGCCAGAA | CTTTCAAGAA | CACTCAGCTC | CCTGAAAGGG | CAATATTTCA | AATTAAACAG | 6840 |
| TACAATTCAG | TTAGCTGTGG | AGTCTCTGAG | TGGCAGCTGG | AAGAAGCACA | AGTATTCTGG | 6900 |
| GCAAAAAGG | AGCAGAGTCT | TGCCCTGAGT | ATTCTCAAGC | AAATGATCAA | GAAGTTGGAT | 6960 |
| GCCAGCTGTG | CAGCGAACAA | TCCCAGCCTA | AAACTTACAT | ACACAGAATG | TCTGAGGGTT | 7020 |
| TGTGGCAACT | GGTTAGCAGA | AACGTGCTTA | GAAATCCTG | CGGTCATCAT | GCAGACCTAT | 7080 |
| CTAGAAAAGG | CAGTAGAAGT | TGCTGGAAAT | TATGATGGAG | AAAGTAGTGA | TGAGCTAAGA | 7140 |
| AATGGAAAAA | TGAAGGCATT | TCTCTCATTA | GCCCGGTTTT | CAGATACTCA | ATACCAAAGA | 7200 |
| ATTGAAAACT | ACATGAAATC | ATCGGAATTT | GAAAACAAGC | AAGCTCTCCT | GAAAAGAGCC | 7260 |
| AAAGAGGAAG | TAGGTCTCCT | TAGGGAACAT | AAAATTCAGA | CAAACAGATA | CACAGTAAAG | 7320 |
| GTTCAGCGAG | AGCTGGAGTT | GGATGAATTA | GCCCTGCGTG | CACTGAAAGA | GGATCGTAAA | 7380 |
| CGCTTCTTAT | GTAAAGCAGT | TGAAAATTAT | ATCAACTGCT | TATTAAGTGG | AGAAGAACAT | 7440 |

```
GATATGTGGG  TATTCCGACT  TTGTTCCCTC  TGGCTTGAAA  ATTCTGGAGT  TTCTGAAGTC   7500
AATGGCATGA  TGAAGAGAGA  CGGAATGAAG  ATTCCAACAT  ATAAATTTTT  GCCTCTTATG   7560
TACCAATTGG  CTGCTAGAAT  GGGGACCAAG  ATGATGGGAG  GCCTAGGATT  TCATGAAGTC   7620
CTCAATAATC  TAATCTCTAG  AATTTCAATG  GATCACCCCC  ATCACACTTT  GTTTATTATA   7680
CTGGCCTTAG  CAAATGCAAA  CAGAGATGAA  TTTCTGACTA  AACCAGAGGT  AGCCAGAAGA   7740
AGCAGAATAA  CTAAAAATGT  GCCTAAACAA  AGCTCTCAGC  TTGATGAGGA  TCGAACAGAG   7800
GCTGCAAATA  GAATAATATG  TACTATCAGA  AGTAGGAGAC  CTCAGATGGT  CAGAAGTGTT   7860
GAGGCACTTT  GTGATGCTTA  TATTATATTA  GCAAACTTAG  ATGCCACTCA  GTGGAAGACT   7920
CAGAGAAAAG  GCATAAATAT  TCCAGCAGAC  CAGCCAATTA  CTAAACTTAA  GAATTTAGAA   7980
GATGTTGTTG  TCCCTACTAT  GGAAATTAAG  GTGGACCACA  CAGGAGAATA  TGGAAATCTG   8040
GTGACTATAC  AGTCATTTAA  AGCAGAATTT  CGCTTAGCAG  GAGGTGTAAA  TTTACCAAAA   8100
ATAATAGATT  GTGTAGGTTC  CGATGGCAAG  GAGAGGAGAC  AGCTTGTTAA  GGGCCGTGAT   8160
GACCTGAGAC  AAGATGCTGT  CATGCAACAG  GTCTTCCAGA  TGTGTAATAC  ATTACTGCAG   8220
AGAAACACGG  AAACTAGGAA  GAGGAAATTA  ACTATCTGTA  CTTATAAGGT  GGTTCCCCTC   8280
TCTCAGCGAA  GTGGTGTTCT  TGAATGGTGC  ACAGGAACTG  TCCCCATTGG  TGAATTTCTT   8340
GTTAACAATG  AAGATGGTGC  TCATAAAAGA  TACAGGCCAA  ATGATTTCAG  TGCCTTTCAG   8400
TGCCAAAAGA  AAATGATGGA  GGTGCAAAAA  AAGTCTTTTG  AAGAGAAATA  TGAAGTCTTC   8460
ATGGATGTTT  GCCAAAATTT  TCAACCAGTT  TTCCGTTACT  TCTGCATGGA  AAAATTCTTG   8520
GATCCAGCTA  TTTGGTTTGA  GAAGCGATTG  GCTTATACGC  GCAGTGTAGC  TACTTCTTCT   8580
ATTGTTGGTT  ACATACTTGG  ACTTGGTGAT  AGACATGTAC  AGAATATCTT  GATAAATGAG   8640
CAGTCAGCAG  AACTTGTACA  TATAGATCTA  GGTGTTGCTT  TTGAACAGGG  CAAAATCCTT   8700
CCTACTCCTG  AGACAGTTCC  TTTTAGACTC  ACCAGAGATA  TTGTGGATGG  CATGGGCATT   8760
ACGGGTGTTG  AAGGTGTCTT  CAGAAGATGC  TGTGAGAAAA  CCATGGAAGT  GATGAGAAAC   8820
TCTCAGGAAA  CTCTGTTAAC  CATTGTAGAG  GTCCTTCTAT  ATGATCCACT  CTTTGACTGG   8880
ACCATGAATC  CTTTGAAAGC  TTTGTATTTA  CAGCAGAGGC  CGGAAGATGA  AACTGAGCTT   8940
CACCCTACTC  TGAATGCAGA  TGACCAAGAA  TGCAAACGAA  ATCTCAGTGA  TATTGACCAG   9000
AGTTTCAACA  AAGTAGCTGA  ACGTGTCTTA  ATGAGACTAC  AAGAGAAACT  GAAAGGAGTG   9060
GAAGAAGGCA  CTGTGCTCAG  TGTTGGTGGA  CAAGTGAATT  TGCTCATACA  GCAGGCCATA   9120
GACCCCAAAA  ATCTCAGCCG  ACTTTTCCCA  GGATGGAAAG  CTTGGGTGTG  A            9171
```

( 2 ) INFORMATION FOR SEQ ID NO:3:

( i ) SEQUENCE CHARACTERISTICS:
        ( A ) LENGTH: 3056 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO:3:

```
Met  Ser  Leu  Val  Leu  Asn  Asp  Leu  Leu  Ile  Cys  Cys  Arg  Gln  Leu  Glu
 1              5                        10                        15

His  Asp  Arg  Ala  Thr  Glu  Arg  Lys  Lys  Glu  Val  Glu  Lys  Phe  Lys  Arg
         20                        25                        30
```

```
Leu Ile Arg Asp Pro Glu Thr Ile Lys His Leu Asp Arg His Ser Asp
         35                  40                  45
Ser Lys Gln Gly Lys Tyr Leu Asn Trp Asp Ala Val Phe Arg Phe Leu
     50                  55                  60
Gln Lys Tyr Ile Gln Lys Glu Thr Glu Cys Leu Arg Ile Ala Lys Pro
 65                  70                  75                  80
Asn Val Ser Ala Ser Thr Gln Ala Ser Arg Gln Lys Lys Met Gln Glu
                 85                  90                  95
Ile Ser Ser Leu Val Lys Tyr Phe Ile Lys Cys Ala Asn Arg Arg Ala
             100                 105                 110
Pro Arg Leu Lys Cys Gln Glu Leu Leu Asn Tyr Ile Met Asp Thr Val
         115                 120                 125
Lys Asp Ser Ser Asn Gly Ala Ile Tyr Gly Ala Asp Cys Ser Asn Ile
130                 135                 140
Leu Leu Lys Asp Ile Leu Ser Val Arg Lys Tyr Trp Cys Glu Ile Ser
145                 150                 155                 160
Gln Gln Gln Trp Leu Glu Leu Phe Ser Val Tyr Phe Arg Leu Tyr Leu
                 165                 170                 175
Lys Pro Ser Gln Asp Val His Arg Val Leu Ala Arg Ile Ile His
             180                 185                 190
Ala Val Thr Lys Gly Cys Cys Ser Gln Thr Asp Gly Leu Asn Ser Lys
         195                 200                 205
Phe Leu Asp Phe Phe Ser Lys Ala Ile Gln Cys Ala Arg Gln Glu Lys
         210                 215                 220
Ser Ser Ser Gly Leu Asn His Ile Leu Ala Ala Leu Thr Ile Phe Leu
225                 230                 235                 240
Lys Thr Leu Ala Val Asn Phe Arg Ile Arg Val Cys Glu Leu Gly Asp
                 245                 250                 255
Glu Ile Leu Pro Thr Leu Val Tyr Ile Trp Thr Gln His Arg Leu Asn
             260                 265                 270
Asp Ser Leu Lys Glu Val Ile Ile Glu Leu Phe Gln Leu Gln Ile Tyr
         275                 280                 285
Ile His His Pro Lys Gly Ala Lys Thr Gln Glu Lys Gly Ala Tyr Glu
         290                 295                 300
Ser Thr Lys Trp Arg Ser Ile Leu Tyr Asn Leu Tyr Asp Leu Leu Val
305                 310                 315                 320
Asn Glu Ile Ser His Ile Gly Ser Arg Gly Lys Tyr Ser Ser Gly Phe
                 325                 330                 335
Arg Asn Ile Ala Val Lys Glu Asn Leu Ile Glu Leu Met Ala Asp Ile
             340                 345                 350
Cys His Gln Val Phe Asn Glu Asp Thr Arg Ser Leu Glu Ile Ser Gln
         355                 360                 365
Ser Tyr Thr Thr Thr Gln Arg Glu Ser Ser Asp Tyr Ser Val Pro Cys
370                 375                 380
Lys Arg Lys Lys Ile Glu Leu Gly Trp Glu Val Ile Lys Asp His Leu
385                 390                 395                 400
Gln Lys Ser Gln Asn Asp Phe Asp Leu Val Pro Trp Leu Gln Ile Ala
                 405                 410                 415
Thr Gln Leu Ile Ser Lys Tyr Pro Ala Ser Leu Pro Asn Cys Glu Leu
             420                 425                 430
Ser Pro Leu Leu Met Ile Leu Ser Gln Leu Leu Pro Gln Gln Arg His
         435                 440                 445
Gly Glu Arg Thr Pro Tyr Val Leu Arg Cys Leu Thr Glu Val Ala Leu
450                 455                 460
```

-continued

| | | | | | | | | | | | | | | |
|---|---|---|---|---|---|---|---|---|---|---|---|---|---|---|
| Cys 465 | Gln | Asp | Lys | Arg | Ser 470 | Asn | Leu | Glu | Ser | Ser 475 | Gln | Lys | Ser | Asp Leu 480 |
| Leu | Lys | Leu | Trp | Asn 485 | Lys | Ile | Trp | Cys | Ile 490 | Thr | Phe | Arg | Gly | Ile Ser 495 |
| Ser | Glu | Gln | Lys | Gln 500 | Ala | Glu | Asn | Phe 505 | Gly | Leu | Leu | Gly | Ala 510 | Ile Ile |
| Gln | Gly | Ser | Leu 515 | Val | Glu | Val | Asp 520 | Arg | Glu | Phe | Trp | Lys 525 | Leu | Phe Thr |
| Gly | Ser | Ala 530 | Cys | Arg | Pro | Ser 535 | Cys | Pro | Ala | Val 540 | Cys | Cys | Leu | Thr Leu |
| Ala 545 | Leu | Thr | Thr | Ser | Ile 550 | Val | Pro | Gly | Ala | Val 555 | Lys | Met | Gly | Ile Glu 560 |
| Gln | Asn | Met | Cys | Glu 565 | Val | Asn | Arg | Ser | Phe 570 | Ser | Leu | Lys | Glu | Ser Ile 575 |
| Met | Lys | Trp | Leu 580 | Leu | Phe | Tyr | Gln | Leu 585 | Glu | Gly | Asp | Leu | Glu 590 | Asn Ser |
| Thr | Glu | Val 595 | Pro | Pro | Ile | Leu 600 | His | Ser | Asn | Phe | Pro 605 | His | Leu | Val Leu |
| Glu | Lys 610 | Ile | Leu | Val | Ser | Leu 615 | Thr | Met | Lys | Asn | Cys 620 | Lys | Ala | Ala Met |
| Asn 625 | Phe | Phe | Gln | Ser | Val 630 | Pro | Glu | Cys | Glu | His 635 | His | His | Lys | Asp Lys 640 |
| Glu | Glu | Leu | Ser | Phe 645 | Ser | Glu | Val | Glu | Leu 650 | Phe | Leu | Gln | Thr 655 | Thr |
| Phe | Asp | Lys | Met 660 | Asp | Phe | Leu | Thr | Ile 665 | Val | Arg | Glu | Cys | Gly 670 | Ile Glu |
| Lys | His | Gln 675 | Ser | Ser | Ile | Gly | Phe 680 | Ser | Val | His | Gln | Asn 685 | Leu | Lys Glu |
| Ser | Leu | Asp 690 | Arg | Cys | Leu | Leu 695 | Gly | Leu | Ser | Glu | Gln 700 | Leu | Leu | Asn Asn |
| Tyr 705 | Ser | Ser | Glu | Ile | Thr 710 | Asn | Ser | Glu | Thr | Leu 715 | Val | Arg | Cys | Ser Arg 720 |
| Leu | Leu | Val | Gly | Val 725 | Leu | Gly | Cys | Tyr | Cys 730 | Tyr | Met | Gly | Val | Ile Ala 735 |
| Glu | Glu | Glu | Ala 740 | Tyr | Lys | Ser | Glu | Leu 745 | Phe | Gln | Lys | Ala | Asn 750 | Ser Leu |
| Met | Gln | Cys 755 | Ala | Gly | Glu | Ser | Ile 760 | Thr | Leu | Phe | Lys | Asn 765 | Lys | Thr Asn |
| Glu | Glu | Phe 770 | Arg | Ile | Gly | Ser 775 | Leu | Arg | Asn | Met | Met 780 | Gln | Leu | Cys Thr |
| Arg 785 | Cys | Leu | Ser | Asn | Cys 790 | Thr | Lys | Lys | Ser | Pro 795 | Asn | Lys | Ile | Ala Ser 800 |
| Gly | Phe | Phe | Leu | Arg 805 | Leu | Leu | Thr | Ser | Lys 810 | Leu | Met | Asn | Asp | Ile Ala 815 |
| Asp | Ile | Cys | Lys 820 | Ser | Leu | Ala | Ser | Phe 825 | Ile | Lys | Lys | Pro | Phe 830 | Asp Arg |
| Gly | Glu | Val 835 | Glu | Ser | Met | Glu | Asp 840 | Asp | Thr | Asn | Gly | Asn 845 | Leu | Met Glu |
| Val | Glu | Asp 850 | Gln | Ser | Ser | Met 855 | Asn | Leu | Phe | Asn | Asp 860 | Tyr | Pro | Asp Ser |
| Ser 865 | Val | Ser | Asp | Ala | Asn 870 | Glu | Pro | Gly | Glu | Ser 875 | Gln | Ser | Thr | Ile Gly 880 |
| Ala | Ile | Asn | Pro | Leu | Ala | Glu | Glu | Tyr | Leu | Ser | Lys | Gln | Asp | Leu Leu |

```
                                        885                           890                           895
     Phe  Leu  Asp  Met  Leu  Lys  Phe  Leu  Leu  Cys  Val  Thr  Ala  Gln
               900                      905                      910

Thr  Asn  Thr  Val  Ser  Phe  Arg  Ala  Ala  Asp  Ile  Arg  Arg  Lys  Leu  Leu
               915                      920                      925

Met  Leu  Ile  Asp  Ser  Ser  Thr  Leu  Glu  Pro  Thr  Lys  Ser  Leu  His  Leu
          930                      935                      940

His  Met  Tyr  Leu  Met  Leu  Leu  Lys  Glu  Leu  Pro  Gly  Glu  Glu  Tyr  Pro
     945                      950                      955                      960

Leu  Pro  Met  Glu  Asp  Val  Leu  Glu  Leu  Leu  Lys  Pro  Leu  Ser  Asn  Val
                    965                      970                      975

Cys  Ser  Leu  Tyr  Arg  Arg  Asp  Gln  Asp  Val  Cys  Lys  Thr  Ile  Leu  Asn
                    980                      985                      990

His  Val  Leu  His  Val  Val  Lys  Asn  Leu  Gly  Gln  Ser  Asn  Met  Asp  Ser
               995                      1000                     1005

Glu  Asn  Thr  Arg  Asp  Ala  Gln  Gly  Gln  Phe  Leu  Thr  Val  Ile  Gly  Ala
          1010                     1015                     1020

Phe  Trp  His  Leu  Thr  Lys  Glu  Arg  Lys  Tyr  Ile  Phe  Ser  Val  Arg  Met
     1025                     1030                     1035                     1040

Ala  Leu  Val  Asn  Cys  Leu  Lys  Thr  Leu  Leu  Glu  Ala  Asp  Pro  Tyr  Ser
                    1045                     1050                     1055

Lys  Trp  Ala  Ile  Leu  Asn  Val  Met  Gly  Lys  Asp  Phe  Pro  Val  Asn  Glu
                    1060                     1065                     1070

Val  Phe  Thr  Gln  Phe  Leu  Ala  Asp  Asn  His  His  Gln  Val  Arg  Met  Leu
          1075                     1080                     1085

Ala  Ala  Glu  Ser  Ile  Asn  Arg  Leu  Phe  Gln  Asp  Thr  Lys  Gly  Asp  Ser
          1090                     1095                     1100

Ser  Arg  Leu  Leu  Lys  Ala  Leu  Pro  Leu  Lys  Leu  Gln  Gln  Thr  Ala  Phe
     1105                     1110                     1115                     1120

Glu  Asn  Ala  Tyr  Leu  Lys  Ala  Gln  Glu  Gly  Met  Arg  Glu  Met  Ser  His
                    1125                     1130                     1135

Ser  Ala  Glu  Asn  Pro  Glu  Thr  Leu  Asp  Glu  Ile  Tyr  Asn  Arg  Lys  Ser
                    1140                     1145                     1150

Val  Leu  Leu  Thr  Leu  Ile  Ala  Val  Val  Leu  Ser  Cys  Ser  Pro  Ile  Cys
                    1155                     1160                     1165

Glu  Lys  Gln  Ala  Leu  Phe  Ala  Leu  Cys  Lys  Ser  Val  Lys  Glu  Asn  Gly
          1170                     1175                     1180

Leu  Glu  Pro  His  Leu  Val  Lys  Lys  Val  Leu  Glu  Lys  Val  Ser  Glu  Thr
     1185                     1190                     1195                     1200

Phe  Gly  Tyr  Arg  Arg  Leu  Glu  Asp  Phe  Met  Ala  Ser  His  Leu  Asp  Tyr
                    1205                     1210                     1215

Leu  Val  Leu  Glu  Trp  Leu  Asn  Leu  Gln  Asp  Thr  Glu  Tyr  Asn  Leu  Ser
                    1220                     1225                     1230

Ser  Phe  Pro  Phe  Ile  Leu  Leu  Asn  Tyr  Thr  Asn  Ile  Glu  Asp  Phe  Tyr
                    1235                     1240                     1245

Arg  Ser  Cys  Tyr  Lys  Val  Leu  Ile  Pro  His  Leu  Val  Ile  Arg  Ser  His
                    1250                     1255                     1260

Phe  Asp  Glu  Val  Lys  Ser  Ile  Ala  Asn  Gln  Ile  Gln  Glu  Asp  Trp  Lys
     1265                     1270                     1275                     1280

Ser  Leu  Leu  Thr  Asp  Cys  Phe  Pro  Lys  Ile  Leu  Val  Asn  Ile  Leu  Pro
                    1285                     1290                     1295

Tyr  Phe  Ala  Tyr  Glu  Gly  Thr  Arg  Asp  Ser  Gly  Met  Ala  Gln  Gln  Arg
                    1300                     1305                     1310
```

```
Glu  Thr  Ala  Thr  Lys  Val  Tyr  Asp  Met  Leu  Lys  Ser  Glu  Asn  Leu  Leu
          1315                     1320                1325

Gly  Lys  Gln  Ile  Asp  His  Leu  Phe  Ile  Ser  Asn  Leu  Pro  Glu  Ile  Val
     1330                1335                1340

Val  Glu  Leu  Leu  Met  Thr  Leu  His  Glu  Pro  Asn  Ser  Ser  Ala  Ser
1345                1350                1355                     1360

Gln  Ser  Thr  Asp  Leu  Cys  Asp  Phe  Ser  Gly  Asp  Leu  Asp  Pro  Ala  Pro
               1365                     1370                1375

Asn  Pro  Pro  His  Phe  Pro  Ser  His  Val  Ile  Lys  Ala  Thr  Phe  Ala  Tyr
               1380                     1385                1390

Ile  Ser  Asn  Cys  His  Lys  Thr  Lys  Leu  Lys  Ser  Ile  Leu  Glu  Ile  Leu
          1395                     1400                1405

Ser  Lys  Ser  Pro  Asp  Ser  Tyr  Gln  Lys  Ile  Leu  Leu  Ala  Ile  Cys  Glu
     1410                1415                1420

Gln  Ala  Ala  Glu  Thr  Asn  Asn  Val  Tyr  Lys  Lys  His  Arg  Ile  Leu  Lys
1425                1430                1435                     1440

Ile  Tyr  His  Leu  Phe  Val  Ser  Leu  Leu  Leu  Lys  Asp  Ile  Lys  Ser  Gly
               1445                     1450                1455

Leu  Gly  Gly  Ala  Trp  Ala  Phe  Val  Leu  Arg  Asp  Val  Ile  Tyr  Thr  Leu
               1460                     1465                1470

Ile  His  Tyr  Ile  Asn  Gln  Arg  Pro  Ser  Cys  Ile  Met  Asp  Val  Ser  Leu
          1475                     1480                1485

Arg  Ser  Phe  Ser  Leu  Cys  Cys  Asp  Leu  Leu  Ser  Gln  Val  Cys  Gln  Thr
     1490                1495                1500

Ala  Val  Thr  Tyr  Cys  Lys  Asp  Ala  Leu  Glu  Asn  His  Leu  His  Val  Ile
1505                1510                1515                     1520

Val  Gly  Thr  Leu  Ile  Pro  Leu  Val  Tyr  Glu  Gln  Val  Glu  Val  Gln  Lys
               1525                     1530                1535

Gln  Val  Leu  Asp  Leu  Leu  Lys  Tyr  Leu  Val  Ile  Asp  Asn  Lys  Asp  Asn
               1540                     1545                1550

Glu  Asn  Leu  Tyr  Ile  Thr  Ile  Lys  Leu  Leu  Asp  Pro  Phe  Pro  Asp  His
          1555                     1560                1565

Val  Val  Phe  Lys  Asp  Leu  Arg  Ile  Thr  Gln  Gln  Lys  Ile  Lys  Tyr  Ser
     1570                1575                1580

Arg  Gly  Pro  Phe  Ser  Leu  Leu  Glu  Glu  Ile  Asn  His  Phe  Leu  Ser  Val
1585                1590                1595                     1600

Ser  Val  Tyr  Asp  Ala  Leu  Pro  Leu  Thr  Arg  Leu  Glu  Gly  Leu  Lys  Asp
               1605                     1610                1615

Leu  Arg  Arg  Gln  Leu  Glu  Leu  His  Lys  Asp  Gln  Met  Val  Asp  Ile  Met
               1620                     1625                1630

Arg  Ala  Ser  Gln  Asp  Asn  Pro  Gln  Asp  Gly  Ile  Met  Val  Lys  Leu  Val
          1635                     1640                1645

Val  Asn  Leu  Leu  Gln  Leu  Ser  Lys  Met  Ala  Ile  Asn  His  Thr  Gly  Glu
     1650                1655                1660

Lys  Glu  Val  Leu  Glu  Ala  Val  Gly  Ser  Cys  Leu  Gly  Glu  Val  Gly  Pro
1665                1670                1675                     1680

Ile  Asp  Phe  Ser  Thr  Ile  Ala  Ile  Gln  His  Ser  Lys  Asp  Ala  Ser  Tyr
               1685                     1690                1695

Thr  Lys  Ala  Leu  Lys  Leu  Phe  Glu  Asp  Lys  Glu  Leu  Gln  Trp  Thr  Phe
               1700                     1705                1710

Ile  Met  Leu  Thr  Tyr  Leu  Asn  Asn  Thr  Leu  Val  Glu  Asp  Cys  Val  Lys
          1715                     1720                1725

Val  Arg  Ser  Ala  Ala  Val  Thr  Cys  Leu  Lys  Asn  Ile  Leu  Ala  Thr  Lys
     1730                1735                1740
```

```
Thr Gly His Ser Phe Trp Glu Ile Tyr Lys Met Thr Thr Asp Pro Met
1745                1750                1755                1760

Leu Ala Tyr Leu Gln Pro Phe Arg Thr Ser Arg Lys Lys Phe Leu Glu
                1765                1770                1775

Val Pro Arg Phe Asp Lys Glu Asn Pro Phe Glu Gly Leu Asp Asp Ile
                1780                1785                1790

Asn Leu Trp Ile Pro Leu Ser Glu Asn His Asp Ile Trp Ile Lys Thr
                1795                1800                1805

Leu Thr Cys Ala Phe Leu Asp Ser Gly Gly Thr Lys Cys Glu Ile Leu
                1810                1815                1820

Gln Leu Leu Lys Pro Met Cys Glu Val Lys Thr Asp Phe Cys Gln Thr
1825                1830                1835                1840

Val Leu Pro Tyr Leu Ile His Asp Ile Leu Leu Gln Asp Thr Asn Glu
                1845                1850                1855

Ser Trp Arg Asn Leu Leu Ser Thr His Val Gln Gly Phe Phe Thr Ser
                1860                1865                1870

Cys Leu Arg His Phe Ser Gln Thr Ser Arg Ser Thr Thr Pro Ala Asn
                1875                1880                1885

Leu Asp Ser Glu Ser Glu His Phe Phe Arg Cys Cys Leu Asp Lys Lys
                1890                1895                1900

Ser Gln Arg Thr Met Leu Ala Val Val Asp Tyr Met Arg Arg Gln Lys
1905                1910                1915                1920

Arg Pro Ser Ser Gly Thr Ile Phe Asn Asp Ala Phe Trp Leu Asp Leu
                1925                1930                1935

Asn Tyr Leu Glu Val Ala Lys Val Ala Gln Ser Cys Ala Ala His Phe
                1940                1945                1950

Thr Ala Leu Leu Tyr Ala Glu Ile Tyr Ala Asp Lys Lys Ser Met Asp
                1955                1960                1965

Asp Gln Glu Lys Arg Ser Leu Ala Phe Glu Glu Gly Ser Gln Ser Thr
                1970                1975                1980

Thr Ile Ser Ser Leu Ser Glu Lys Ser Lys Glu Glu Thr Gly Ile Ser
1985                1990                1995                2000

Leu Gln Asp Leu Leu Leu Glu Ile Tyr Arg Ser Ile Gly Glu Pro Asp
                2005                2010                2015

Ser Leu Tyr Gly Cys Gly Gly Gly Lys Met Leu Gln Pro Ile Thr Arg
                2020                2025                2030

Leu Arg Thr Tyr Glu His Glu Ala Met Trp Gly Lys Ala Leu Val Thr
                2035                2040                2045

Tyr Asp Leu Glu Thr Ala Ile Pro Ser Ser Thr Arg Gln Ala Gly Ile
                2050                2055                2060

Ile Gln Ala Leu Gln Asn Leu Gly Leu Cys His Ile Leu Ser Val Tyr
2065                2070                2075                2080

Leu Lys Gly Leu Asp Tyr Glu Asn Lys Asp Trp Cys Pro Glu Leu Glu
                2085                2090                2095

Glu Leu His Tyr Gln Ala Ala Trp Arg Asn Met Gln Trp Asp His Cys
                2100                2105                2110

Thr Ser Val Ser Lys Glu Val Glu Gly Thr Ser Tyr His Glu Ser Leu
                2115                2120                2125

Tyr Asn Ala Leu Gln Ser Leu Arg Asp Arg Glu Phe Ser Thr Phe Tyr
                2130                2135                2140

Glu Ser Leu Lys Tyr Ala Arg Val Lys Glu Val Glu Glu Met Cys Lys
2145                2150                2155                2160

Arg Ser Leu Glu Ser Val Tyr Ser Leu Tyr Pro Thr Leu Ser Arg Leu
```

```
                              2165                         2170                         2175
          Gln   Ala   Ile   Gly   Glu   Leu   Glu   Ser   Ile   Gly   Glu   Leu   Phe   Ser   Arg   Ser
                              2180                         2185                         2190

Val   Thr   His   Arg   Gln   Leu   Ser   Glu   Val   Tyr   Ile   Lys   Trp   Gln   Lys   His
                              2195                         2200                         2205

Ser   Gln   Leu   Leu   Lys   Asp   Ser   Asp   Phe   Ser   Phe   Gln   Glu   Pro   Ile   Met
                              2210                         2215                         2220

Ala   Leu   Arg   Thr   Val   Ile   Leu   Glu   Ile   Leu   Met   Glu   Lys   Glu   Met   Asp
          2225                        2230                         2235                         2240

Asn   Ser   Gln   Arg   Glu   Cys   Ile   Lys   Asp   Ile   Leu   Thr   Lys   His   Leu   Val
                              2245                         2250                         2255

Glu   Leu   Ser   Ile   Leu   Ala   Arg   Thr   Phe   Lys   Asn   Thr   Gln   Leu   Pro   Glu
                              2260                         2265                         2270

Arg   Ala   Ile   Phe   Gln   Ile   Lys   Gln   Tyr   Asn   Ser   Val   Ser   Cys   Gly   Val
                              2275                         2280                         2285

Ser   Glu   Trp   Gln   Leu   Glu   Glu   Ala   Gln   Val   Phe   Trp   Ala   Lys   Lys   Glu
                              2290                         2295                         2300

Gln   Ser   Leu   Ala   Leu   Ser   Ile   Leu   Lys   Gln   Met   Ile   Lys   Lys   Leu   Asp
          2305                        2310                         2315                         2320

Ala   Ser   Cys   Ala   Ala   Asn   Asn   Pro   Ser   Leu   Lys   Leu   Thr   Tyr   Thr   Glu
                              2325                         2330                         2335

Cys   Leu   Arg   Val   Cys   Gly   Asn   Trp   Leu   Ala   Glu   Thr   Cys   Leu   Glu   Asn
                              2340                         2345                         2350

Pro   Ala   Val   Ile   Met   Gln   Thr   Tyr   Leu   Glu   Lys   Ala   Val   Glu   Val   Ala
                              2355                         2360                         2365

Gly   Asn   Tyr   Asp   Gly   Glu   Ser   Ser   Asp   Glu   Leu   Arg   Asn   Gly   Lys   Met
                              2370                         2375                         2380

Lys   Ala   Phe   Leu   Ser   Leu   Ala   Arg   Phe   Ser   Asp   Thr   Gln   Tyr   Gln   Arg
          2385                        2390                         2395                         2400

Ile   Glu   Asn   Tyr   Met   Lys   Ser   Ser   Glu   Phe   Glu   Asn   Lys   Gln   Ala   Leu
                              2405                         2410                         2415

Leu   Lys   Arg   Ala   Lys   Glu   Glu   Val   Gly   Leu   Leu   Arg   Glu   His   Lys   Ile
                              2420                         2425                         2430

Gln   Thr   Asn   Arg   Tyr   Thr   Val   Lys   Val   Gln   Arg   Glu   Leu   Glu   Leu   Asp
                              2435                         2440                         2445

Glu   Leu   Ala   Leu   Arg   Ala   Leu   Lys   Glu   Asp   Arg   Lys   Arg   Phe   Leu   Cys
                              2450                         2455                         2460

Lys   Ala   Val   Glu   Asn   Tyr   Ile   Asn   Cys   Leu   Leu   Ser   Gly   Glu   Glu   His
          2465                        2470                         2475                         2480

Asp   Met   Trp   Val   Phe   Arg   Leu   Cys   Ser   Leu   Trp   Leu   Glu   Asn   Ser   Gly
                              2485                         2490                         2495

Val   Ser   Glu   Val   Asn   Gly   Met   Met   Lys   Arg   Asp   Gly   Met   Lys   Ile   Pro
                              2500                         2505                         2510

Thr   Tyr   Lys   Phe   Leu   Pro   Leu   Met   Tyr   Gln   Leu   Ala   Ala   Arg   Met   Gly
                              2515                         2520                         2525

Thr   Lys   Met   Met   Gly   Gly   Leu   Gly   Phe   His   Glu   Val   Leu   Asn   Asn   Leu
                              2530                         2535                         2540

Ile   Ser   Arg   Ile   Ser   Met   Asp   His   Pro   His   His   Thr   Leu   Phe   Ile   Ile
          2545                        2550                         2555                         2560

Leu   Ala   Leu   Ala   Asn   Ala   Asn   Arg   Asp   Glu   Phe   Leu   Thr   Lys   Pro   Glu
                              2565                         2570                         2575

Val   Ala   Arg   Arg   Ser   Arg   Ile   Thr   Lys   Asn   Val   Pro   Lys   Gln   Ser   Ser
                              2580                         2585                         2590
```

```
Gln  Leu  Asp  Glu  Asp  Arg  Thr  Glu  Ala  Ala  Asn  Arg  Ile  Ile  Cys  Thr
          2595                    2600                    2605

Ile  Arg  Ser  Arg  Arg  Pro  Gln  Met  Val  Arg  Ser  Val  Glu  Ala  Leu  Cys
     2610                    2615                    2620

Asp  Ala  Tyr  Ile  Ile  Leu  Ala  Asn  Leu  Asp  Ala  Thr  Gln  Trp  Lys  Thr
2625                    2630                    2635                         2640

Gln  Arg  Lys  Gly  Ile  Asn  Ile  Pro  Ala  Asp  Gln  Pro  Ile  Thr  Lys  Leu
               2645                    2650                         2655

Lys  Asn  Leu  Glu  Asp  Val  Val  Pro  Thr  Met  Glu  Ile  Lys  Val  Asp
               2660                    2665                    2670

His  Thr  Gly  Glu  Tyr  Gly  Asn  Leu  Val  Thr  Ile  Gln  Ser  Phe  Lys  Ala
               2675                    2680                    2685

Glu  Phe  Arg  Leu  Ala  Gly  Gly  Val  Asn  Leu  Pro  Lys  Ile  Ile  Asp  Cys
               2690                    2695                    2700

Val  Gly  Ser  Asp  Gly  Lys  Glu  Arg  Arg  Gln  Leu  Val  Lys  Gly  Arg  Asp
2705                    2710                    2715                         2720

Asp  Leu  Arg  Gln  Asp  Ala  Val  Met  Gln  Gln  Val  Phe  Gln  Met  Cys  Asn
                    2725                    2730                    2735

Thr  Leu  Leu  Gln  Arg  Asn  Thr  Glu  Thr  Arg  Lys  Arg  Lys  Leu  Thr  Ile
               2740                    2745                    2750

Cys  Thr  Tyr  Lys  Val  Val  Pro  Leu  Ser  Gln  Arg  Ser  Gly  Val  Leu  Glu
               2755                    2760                    2765

Trp  Cys  Thr  Gly  Thr  Val  Pro  Ile  Gly  Glu  Phe  Leu  Val  Asn  Asn  Glu
     2770                    2775                    2780

Asp  Gly  Ala  His  Lys  Arg  Tyr  Arg  Pro  Asn  Asp  Phe  Ser  Ala  Phe  Gln
2785                    2790                    2795                         2800

Cys  Gln  Lys  Lys  Met  Met  Glu  Val  Gln  Lys  Lys  Ser  Phe  Glu  Glu  Lys
               2805                    2810                         2815

Tyr  Glu  Val  Phe  Met  Asp  Val  Cys  Gln  Asn  Phe  Gln  Pro  Val  Phe  Arg
               2820                    2825                    2830

Tyr  Phe  Cys  Met  Glu  Lys  Phe  Leu  Asp  Pro  Ala  Ile  Trp  Phe  Glu  Lys
               2835                    2840                    2845

Arg  Leu  Ala  Tyr  Thr  Arg  Ser  Val  Ala  Thr  Ser  Ser  Ile  Val  Gly  Tyr
     2850                    2855                    2860

Ile  Leu  Gly  Leu  Gly  Asp  Arg  His  Val  Gln  Asn  Ile  Leu  Ile  Asn  Glu
2865                    2870                    2875                         2880

Gln  Ser  Ala  Glu  Leu  Val  His  Ile  Asp  Leu  Gly  Val  Ala  Phe  Glu  Gln
                    2885                    2890                         2895

Gly  Lys  Ile  Leu  Pro  Thr  Pro  Glu  Thr  Val  Pro  Phe  Arg  Leu  Thr  Arg
               2900                    2905                    2910

Asp  Ile  Val  Asp  Gly  Met  Gly  Ile  Thr  Gly  Val  Glu  Gly  Val  Phe  Arg
          2915                    2920                    2925

Arg  Cys  Cys  Glu  Lys  Thr  Met  Glu  Val  Met  Arg  Asn  Ser  Gln  Glu  Thr
               2930                    2935                    2940

Leu  Leu  Thr  Ile  Val  Glu  Val  Leu  Leu  Tyr  Asp  Pro  Leu  Phe  Asp  Trp
2945                    2950                    2955                         2960

Thr  Met  Asn  Pro  Leu  Lys  Ala  Leu  Tyr  Leu  Gln  Gln  Arg  Pro  Glu  Asp
               2965                    2970                         2975

Glu  Thr  Glu  Leu  His  Pro  Thr  Leu  Asn  Ala  Asp  Asp  Gln  Glu  Cys  Lys
               2980                    2985                    2990

Arg  Asn  Leu  Ser  Asp  Ile  Asp  Gln  Ser  Phe  Asp  Lys  Val  Ala  Glu  Arg
               2995                    3000                    3005

Val  Leu  Met  Arg  Leu  Gln  Glu  Lys  Leu  Lys  Gly  Val  Glu  Glu  Gly  Thr
          3010                    3015                    3020
```

```
            Val  Leu  Ser  Val  Gly  Gly  Gln  Val  Asn  Leu  Leu  Ile  Gln  Gln  Ala  Ile
            3025                3030                3035                          3040

Asp  Pro  Lys  Asn  Leu  Ser  Arg  Leu  Phe  Pro  Gly  Trp  Lys  Ala  Trp  Val
                                3045                     3050               3055
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
            His  Glu  Pro  Ala  Asn  Ser  Ser  Ala  Ser  Gln  Ser  Thr  Asp  Leu  Cys
            1                   5                        10                         15
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
            Cys  Lys  Arg  Asn  Leu  Ser  Asp  Ile  Asp  Gln  Ser  Phe  Asp  Lys  Val
            1                   5                        10                         15
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
            Pro  Glu  Asp  Glu  Thr  Glu  Leu  His  Pro  Thr  Leu  Asn  Ala  Asp  Asp  Gln
            1                   5                        10                         15

Glu  Cys
```

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
            Cys  Lys  Ser  Leu  Ala  Ser  Phe  Ile  Lys  Lys  Pro  Phe  Asp  Arg  Gly  Glu
            1                   5                        10                         15

Val  Glu  Ser  Met  Glu  Asp  Asp  Thr  Asn  Gly
                            20                    25
```

( 2 ) INFORMATION FOR SEQ ID NO:8:

( i ) SEQUENCE CHARACTERISTICS:

(A) LENGTH: 3607 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (ix) FEATURE:
(A) NAME/KEY: 3'UTR
(B) LOCATION: 1..3607

(xi) SEQUENCE DESCRIPTION: SEQ ID NO:8:

```
TCTTCAGTAT ATGAATTACC CTTTCATTCA GCCTTTAGAA ATTATATTTT AGCCTTTATT      60
TTTAACCTGC CAACATACTT TAAGTAGGGA TTAATATTTA AGTGAACTAT TGTGGGTTTT     120
TTTGAATGTT GGTTTTAATA CTTGATTTAA TCACCACTCA AAAATGTTTT GATGGTCTTA     180
AGGAACATCT CTGCTTTCAC TCTTTAGAAA TAATGGTCAT TCGGGCTGGG CGCAGCGGCT     240
CACGCCTGTA ATCCCAGCAC TTTGGGAGGC CGAGGTGAGC GGATCACAAG GTCAGGAGTT     300
CGAGACCAGC CTGGCCAAGA GACCAGCCTG GCCAGTATGG TGAAACCCTG TCTCTACTAA     360
AAATACAAAA ATTAGCCGAG CATGGTGGCG GGCACCTGTA ATCCCAGCTA CTCGAGAGGC     420
TGAGGCAGGA GAATCTCTTG AACCTGGGAG GTGAAGGTTG CTGTGGGCCA AAATCATGCC     480
ATTGCACTCC AGCCTGGGTG ACAAGAGCGA AACTCCATCT CAAAAAAAAA AAAAAAAAAC     540
AGAAACTTAT TTGGATTTTT CCTAGTAAGA TCACTCAGTG TTACTAAATA ATGAAGTTGT     600
TATGGAGAAC AAATTTCAAA GACACAGTTA GTGTAGTTAC TATTTTTTA AGTGTGTATT      660
AAAACTTCTC ATTCTATTCT CTTTATCTTT TAAGCCCTTC TGTACTGTCC ATGTATGTTA     720
TCTTTCTGTG ATAACTTCAT AGATTGCCTT CTAGTTCATG AATTCTCTTG TCAGATGTAT     780
ATAATCTCTT TTACCCTATC CATTGGGCTT CTTCTTTCAG AAATTGTTTT TCATTTCTAA     840
TTATGCATCA TTTTTCAGAT CTCTGTTTCT TGATGTCATT TTTAATGTTT TTTTAATGTT     900
TTTTATGTCA CTAATTATTT TAAATGTCTG TACCTGATAG ACACTGTAAT AGTTCTATTA     960
AATTTAGTTC CTGCTGTTTA TATCTGTTGA TTTTTGTATT TGATAGGCTG TTCATCCAGT    1020
TTTGTCTTTT TGAAAAGTGA GTTTATTTTC AGCAAGGCTT TATCTATGGG AATCTTGAGT    1080
GTCTGTTTAT GTCATATTCC CAGGGCTGTT GCTGCACACA AGCCCATTCT TATTTTAATT    1140
TCTTGGCTTT AGGGTTTCCA TACCTGAAGT GTAGCATAAA TACTGATAGG AGATTTCCCA    1200
GGCCAAGGCA AACACACTTC CTCCTCATCT CCTTGTGCTA GTGGGCAGAA TATTTGATTG    1260
ATGCCTTTTT CACTGAGAGT ATAAGCTTCC ATGTGTCCCA CCTTTATGGC AGGGGTGGAA    1320
GGAGGTACAT TTAATTCCCA CTGCCTGCCT TTGGCAAGCC CTGGGTTCTT TGCTCCCCAT    1380
ATAGATGTCT AAGCTAAAAG CCGTGGGTTA ATGAGACTGG CAAATTGTTC CAGGACAGCT    1440
ACAGCATCAG CTCACATATT CACCTCTCTG GTTTTTCATT CCCCTCATTT TTTTCTGAGA    1500
CAGAGTCTTG CTCTGTCACC CAGGCTGGAG TGCAGTGGCA TGATCTCAGC TCACTGAAAC    1560
CTCTGCCTCC TGGGTTCAAG CAATTCTCCT GCCTCAGCCT CCCGAGTAGC TGGGACTACA    1620
GGCGTGTGCC AACACGCCCG GCTAATTTTT TGTATTTTTA TTAGAGACGG AGTTTCACCG    1680
TGTTAGCCAG GATGGTCTCG ATCGCTTGAC CTCGTGATCC ACCTCCTCG GCCTCCCAAA     1740
GTGCTGGGAT TACAGGTGTG AGCCACCGCG CCCGGCCTCA TTCCCCTCAT TTTTGACCGT    1800
AAGGATTTCC CCTTTCTTGT AAGTTCTGCT ATGTATTTAA AAGAATGTTT TCTACATTTT    1860
ATCCAGCATT TCTCTGTGTT CTGTTGGAAG GGAAGGGCTT AGGTATCTAG TTTGATACAT    1920
```

| AGGTAGAAGT | GGAACATTTC | TCTGTCCCCC | AGCTGTCATC | ATATAAGATA | AACATCAGAT | 1980 |
| AAAAAGCCAC | CTGAAAGTAA | AACTACTGAC | TCGTGTATTA | GTGAGTATAA | TCTCTTCTCC | 2040 |
| ATCCTTAGGA | AAATGTTCAT | CCCAGCTGCG | GAGATTAACA | AATGGGTGAT | TGAGCTTTCT | 2100 |
| CCTCGTATTT | GGACCTTGAA | GGTTATATAA | ATTTTTTTCT | TATGAAGAGT | TGGCATTTCT | 2160 |
| TTTTATTGCC | AATGGCAGGC | ACTCATTCAT | ATTTGATCTC | CTCACCTTCC | CCTCCCCTAA | 2220 |
| AACCAATCTC | CAGAACTTTT | TGGACTATAA | ATTTCTTGGT | TTGACTTCTG | GAGAACTGTT | 2280 |
| CAGAATATTA | CTTTGCATTT | CAAATTACAA | ACTTACCTTG | GTGTATCTTT | TTCTTACAAG | 2340 |
| CTGCCTAAAT | GAATATTTGG | TATATATTGG | TAGTTTTATT | ACTATAGTAA | ATCAAGGAAA | 2400 |
| TGCAGTAAAC | TTAAAATGTC | TTTAAGAAAG | CCCTGAAATC | TTCATGGGTG | AAATTAGAAA | 2460 |
| TTATCAACTA | GATAATAGTA | TAGATAAATG | AATTTGTAGC | TAATTCTTGC | TAGTTGTTGC | 2520 |
| ATCCAGAGAG | CTTTGAATAA | CATCATTAAT | CTACTCTTTA | GCCTTGCATG | GTATGCTATG | 2580 |
| AGGCTCCTGT | TCTGTTCAAG | TATTCTAATC | AATGGCTTTG | AAAAGTTTAT | CAAATTTACA | 2640 |
| TACAGATCAC | AAGCCTAGGA | GAAATAACTA | ATTCACAGAT | GACAGAATTA | AGATTATAAA | 2700 |
| AGATTTTTTT | TTGGTAATTT | TAGTAGAGAC | AGGGTTGCCA | TTGTATTCCA | GCCTTGGCGA | 2760 |
| CAGAGCAAGA | CTCTGCCTCA | AAAAAAAAAA | AAAAAAGGTT | TTGCCAAGCT | GGAACTCTTT | 2820 |
| CTGCAAATGA | CTAAGATAGA | AAACTGCCAA | GGACAAATGA | GGAGTAGTTA | GATTTTGAAA | 2880 |
| ATATTAATCA | TAGAATAGTT | GTTGTATGCT | AAGTCACTGA | CCCATATTAT | GTACAGCATT | 2940 |
| TCTGATCTTT | ACTTTGCAAG | ATTAGTGATA | CTATGCCAAT | ACACTGCTGG | AGAAATCAGA | 3000 |
| ATTTGGAGAA | ATAAGTTGTC | CAAGGCAAGA | AGATAGTAAA | TTATAAGTAC | AAGTGTAATA | 3060 |
| TGGACAGTAT | CTAACTTGAA | AAGATTTCAG | GCGAAAAGAA | TCTGGGGTTT | GCCAGTCAGT | 3120 |
| TGCTCAAAAG | GTCAATGAAA | ACCAAATAGT | GAAGCTATCA | GAGAAGCTAA | TAAATTATAG | 3180 |
| ACTGCTTGAA | CAGTTGTGTC | CAGATTAAGG | GAGATAATAG | CTTTCCCACC | CTACTTTGTG | 3240 |
| CAGGTCATAC | CTCCCCAAAG | TGTTTACCTA | ATCAGTAGGT | TCACAAACTC | TTGGTCATTA | 3300 |
| TAGTATATGC | CTAAAATGTA | TGCACTTAGG | AATGCTAAAA | ATTAAATAT | GGTCTAAAGC | 3360 |
| AAATAAAAGC | AAAGAGGAAA | AACTTTGGAC | ATCGTAAAGA | CTAGAATAGT | CTTTTAAAAA | 3420 |
| GAAAGCCAGT | ATATTGGTTT | GAAATATAGA | GATGTGTCCC | AATTTCAAGT | ATTTTAATTG | 3480 |
| CACCTTAATG | AAATTATCTA | TTTTCTATAG | ATTTTAGTAC | TATTGAATGT | ATTACTTTAC | 3540 |
| TGTTACCTGA | ATTTATTATA | AAGTGTTTTT | GAATAAATAA | TTCTAAAAGC | AAAAAAAAAA | 3600 |
| AAAAAAA | | | | | | 3607 |

( 2 ) INFORMATION FOR SEQ ID NO:9:

( i ) SEQUENCE CHARACTERISTICS:
        ( A ) LENGTH: 884 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: 5'UTR
        ( B ) LOCATION: 1..884

( x i ) SEQUENCE DESCRIPTION: SEQ ID NO:9:

| TCCTCCTTTT | AAACGCCCTG | AATTGAACCC | TGCCTCCTGC | GCATCCTCTT | TTTGTGTCAC | 60 |

-continued

| | | | | | |
|---|---|---|---|---|---|
| CTTAGGGTTC | AGATTTAACT | ACGCGACTTG | ACTAGTCATC | TTTTGATCTC | TCTCTCGTAT | 120
| TTAGTACTTT | TAGTCAGCGA | GCATTTATTG | ATATTTCAAC | TTCAGCCTCG | CGGTTAAGAG | 180
| CTTGGGCTCT | GGAATCATAC | GGCTGGAATT | GGAATTCTGT | CAGTCGTGTG | GCCGCTCTCT | 240
| ACTGTCTTGT | GAAGATAAGT | GAGATAATCT | TGACCTGTGG | TGAGCACTCG | TGAGCGTTAG | 300
| CTGCTGTATT | TACCAGGTAC | AGATAAGACA | ACTACAGTGG | ATGATAATGT | ATGTGGTGAT | 360
| AGGGGAGTAC | TCTGATGGTA | GAGGAGTGAC | TTTGGTTCTC | TGCAAACTCA | GCCTGAGACT | 420
| ATCAATTCAG | TTTGTGGTGA | GACCTCGCAG | TGTTACCTTG | GCAGATGGTA | GAAGCCTTCC | 480
| AGATGGAAGG | AAAAATGCGT | GTAAAGGCAC | AAAGTGTAGA | AGGACCCTGA | AGCTCCAGCG | 540
| TGAGGCCTGG | CATTGAATGA | AATATATTTT | GTGGGTTTTC | AGCTGCTGAA | GTCATAGGAA | 600
| TGGATGAGAC | CAAGAAAACA | AAGCTGTTTT | TGAGGTATGA | GCGGAAGAAG | AGATATCAGG | 660
| AGACTTTCGA | AACAGTCATA | ACGGAAGTTA | ATATGATCAT | TGCTAACATT | TGCTGTGTTT | 720
| CAGGCACTGT | AAGCATGTAT | ATGGGTCCTT | AAAGGGACTC | ATAGAGAGGC | ATACATCACA | 780
| ATTTGGAATT | ATGCATTGGT | TTATCAATTT | ACTGTTTAT | TGTCACCCTG | CTGCCCAGAT | 840
| ATGACTTCAT | GAGGACAGTG | ATGTGTGTTC | TGAAATTGTG | AACC | | 884

( 2 ) INFORMATION FOR SEQ ID NO:10:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| | | | | | |
|---|---|---|---|---|---|
| AGGTAGCTGC | GTGGCTAACG | GAGAAAAGAA | GCCGTGGCCA | CGGGAGGAGG | CGAGAGGAGT | 60
| CGGGATCTGC | GCTGCAGCCA | CCGCCGCGGT | TGATACTACT | TTGACCTTCC | GAGTGCAGTG | 120

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GTAGGGCGC GGAGGCAACG CAGCGGCTTC     30

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GTATGAGCGG AAGAAGAGAT ATCAGGAGAC     30

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GTATGAGCGG AAGAAGAGAT ATCAGGAGAC 30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GTAGGTACTA GTATTGTTTT TCCTTTTATC 30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TTTTCTATTA CTGTGTTTTT GTTTCCTCAG 30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GTAGGATTTG TATCTGTTTA GTTCATTATT 30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TATATATACC TATATGTATT TTTTTACAG 30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GTAGTAAATT ACTTAAATTC AATTTTTCCT 30

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

AACCCATTAT TATTTCCTTT TTATTTTCAG 30

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GTATTCTATT CAAATTTATT TTACTGTCTT 30

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

TTTCTGAAAT TGCATTTTGT TTTCTTGAAG 30

( 2 ) INFORMATION FOR SEQ ID NO:22:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GTAAGTGATG TTATAAATTA TAAATAAATG GC 32

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GTTTTTCTTT ATTTGTTTAT TTGAAATAG 30

( 2 ) INFORMATION FOR SEQ ID NO:24:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

GTATGTTTTG AAGGTTGTTG TTTGTGAATT TTT 33

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CATGACTAAT AATTTTTTTT TTTTTTTAAG 30

( 2 ) INFORMATION FOR SEQ ID NO:26:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GTAATCTAAT CTCTTTTTCT TTTGTTTTGT ATTG     34

( 2 ) INFORMATION FOR SEQ ID NO:27:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CCCAGTTGAG CTTGTTTGTT TCTTCACAG     29

( 2 ) INFORMATION FOR SEQ ID NO:28:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GTATAAAGGA AATGTTTACT GTTTTGAATT T     31

( 2 ) INFORMATION FOR SEQ ID NO:29:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

AAAAATTACA TTTTAATTTT TTGGATTACA G     31

( 2 ) INFORMATION FOR SEQ ID NO:30:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GTACAGTAAG TAGGTCATGT CACATTTAGA     30

( 2 ) INFORMATION FOR SEQ ID NO:31:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

GAAAAAAGTG GATTTATTTT TATTTTACAG     30

( 2 ) INFORMATION FOR SEQ ID NO:32:

( i ) SEQUENCE CHARACTERISTICS:
   ( A ) LENGTH: 30 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:32:

GTAAAGTGTT ACCATTTTCT CATTCAGTGT    30

( 2 ) INFORMATION FOR SEQ ID NO:33:

( i ) SEQUENCE CHARACTERISTICS:
   ( A ) LENGTH: 30 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:33:

TTCCAAATAA CCCTTTTTTT TTTTTTTAG    30

( 2 ) INFORMATION FOR SEQ ID NO:34:

( i ) SEQUENCE CHARACTERISTICS:
   ( A ) LENGTH: 30 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:34:

GTAAGTTCAG CATGCATTAT GTCTGACTTA    30

( 2 ) INFORMATION FOR SEQ ID NO:35:

( i ) SEQUENCE CHARACTERISTICS:
   ( A ) LENGTH: 30 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:35:

TTTTCACAAT TGTCCTTTGT TTTGTTATAG    30

( 2 ) INFORMATION FOR SEQ ID NO:36:

( i ) SEQUENCE CHARACTERISTICS:
   ( A ) LENGTH: 30 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:36:

GTAATTTAAG TTCATTAGCA TGCTGCTGTT    30

( 2 ) INFORMATION FOR SEQ ID NO:37:

( i ) SEQUENCE CHARACTERISTICS:
   ( A ) LENGTH: 30 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:37:

CTAAGTGAAG CTTTTTGTTT TTCTTTGTAG    30

( 2 ) INFORMATION FOR SEQ ID NO:38:

( i ) SEQUENCE CHARACTERISTICS:

(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:38:

GTATGTTATC TAATAATGCT CTTTATCATT 30

(2) INFORMATION FOR SEQ ID NO:39:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:39:

TTATATATTA AAGATCTTAC TTTCTTGAAG 30

(2) INFORMATION FOR SEQ ID NO:40:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:40:

GTGAGATTTT TTAAAAAAG AACTAAGCTT 30

(2) INFORMATION FOR SEQ ID NO:41:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:41:

TATATATTTT TATTTGTGGT TTACTTTAAG 30

(2) INFORMATION FOR SEQ ID NO:42:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:42:

GTAGGAGAAT TTATACTAAT AAAGTTTCGG 30

(2) INFORMATION FOR SEQ ID NO:43:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:43:

AATTTGCATT TTTCCTTCTA TTCACAATAG 30

(2) INFORMATION FOR SEQ ID NO:44:

(i) SEQUENCE CHARACTERISTICS:
(A) LENGTH: 30 base pairs
(B) TYPE: nucleic acid ( C ) STRANDEDNESS: single
( D ) TOPOLOGY: linear ( x i ) SEQUENCE DESCRIPTION: SEQ ID NO:44:

GTAAGATTTT CTTCTTCTTG TTTTGTTTTT 30

( 2 ) INFORMATION FOR SEQ ID NO:45:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

TTGCTTGGTT CTTTGTTTGT CTTAATTGCA G 31

( 2 ) INFORMATION FOR SEQ ID NO:46:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

GTAAGTATGC TTCCTGTTTT GCTATCATAT 30

( 2 ) INFORMATION FOR SEQ ID NO:47:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

CTTGAACATC TTTGTTTCTC TTCCTTGAAG 30

( 2 ) INFORMATION FOR SEQ ID NO:48:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GTAAATACAT ATTTACTACT TGGGATTTCT 30

( 2 ) INFORMATION FOR SEQ ID NO:49:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

TTAGTGTTAA TGAGTGCTTT TTATTTTTAG 30

( 2 ) INFORMATION FOR SEQ ID NO:50:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GTGAGTTACG TTAAATGAAG AAGCTCTTGG 30

( 2 ) INFORMATION FOR SEQ ID NO:51:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

CCTGATTTTT TTCCCTCCTA CCATCTTAG 29

( 2 ) INFORMATION FOR SEQ ID NO:52:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GTAAGAAATT AAAACCTTAT GTTATGTTCA 30

( 2 ) INFORMATION FOR SEQ ID NO:53:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

AAGTTGAACT TTTTTTTTT TTTACCACA G 31

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GTAGGTACAG TCTATTTTGT GGTCCTATT 29

( 2 ) INFORMATION FOR SEQ ID NO:55:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

TTTAACTTTG GAAAACTTAC TTGATTTCAG 30

( 2 ) INFORMATION FOR SEQ ID NO:56:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GTGAGTTTTT GCATTTTTTT AGTAAGATCT                                                            30

( 2 ) INFORMATION FOR SEQ ID NO:57:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:57:

TCATATTTAA CCACAGTTCT TTTCCCGTAG                                                            30

( 2 ) INFORMATION FOR SEQ ID NO:58:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:58:

GTAATGGGTC AAATATTCAT GAAGTATTTG                                                            30

( 2 ) INFORMATION FOR SEQ ID NO:59:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:59:

TTTCATTGTT TCTTTCCTTC CTGTCTTAAG                                                            30

( 2 ) INFORMATION FOR SEQ ID NO:60:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:60:

GTAATTTTAA GTAACATGTA TTTGCTGTTA                                                            30

( 2 ) INFORMATION FOR SEQ ID NO:61:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:61:

TTACAATTTT TTTTTAAATT TCTTTTTAAG                                                            30

( 2 ) INFORMATION FOR SEQ ID NO:62:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:62:

GTATATATGG ATGAGTATTT TATTAGAAGC                                                            30

( 2 ) INFORMATION FOR SEQ ID NO:63:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CTTAACACAT TGACTTTTTG GTTCGTGCAG     30

( 2 ) INFORMATION FOR SEQ ID NO:64:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

GTAAGTTTAT ACATGACATA TGTGAAATTT     30

( 2 ) INFORMATION FOR SEQ ID NO:65:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

AACCTGTATT TTAAATTTTT CTATTTTTAG     30

( 2 ) INFORMATION FOR SEQ ID NO:66:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

GTATGGCTTC AATTTTTATG TACTTTTCAT     30

( 2 ) INFORMATION FOR SEQ ID NO:67:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

TAAATATATT TTAATTTTGT GCCCTTGCAG     30

( 2 ) INFORMATION FOR SEQ ID NO:68:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

GTATGTACAT TTTAAACTTA GAGAACTAGC     30

( 2 ) INFORMATION FOR SEQ ID NO:69:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

TGACTGTATT TTTTCCCTTA ACTCTGTTAG    30

( 2 ) INFORMATION FOR SEQ ID NO:70:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

GTAAGTATAC ATGATGAGTT TAATAATAGA    30

( 2 ) INFORMATION FOR SEQ ID NO:71:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

AAGTTTTTAC TAAATCTGTT TATTTCTAG    30

( 2 ) INFORMATION FOR SEQ ID NO:72:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

GTAAATAACA TATTTAGACC AATATATAAG    30

( 2 ) INFORMATION FOR SEQ ID NO:73:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

TTGTTGTTGT TTTTTTTCT CCCTATATTA G    31

( 2 ) INFORMATION FOR SEQ ID NO:74:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

GTAATTTTCT GACTCATCTT CAAAATGGTA    30

( 2 ) INFORMATION FOR SEQ ID NO:75:

-continued ( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:75:

TATAATTTTT TCTTTTTAAA TTATATTTAG     30

( 2 ) INFORMATION FOR SEQ ID NO:76:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

GTAATAAAAA TTTCATCATC TACTATTTTT     30

( 2 ) INFORMATION FOR SEQ ID NO:77:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

GTTAAAAGCA AGTTACATTT TCTCTTTTAG     30

( 2 ) INFORMATION FOR SEQ ID NO:78:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

GTGCTAATTT TAAATGACAT GGGCTATTT     29

( 2 ) INFORMATION FOR SEQ ID NO:79:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

TTAAACTAAT TTTAAAAAA TTATTTCTAG     30

( 2 ) INFORMATION FOR SEQ ID NO:80:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

GTAAACTACA GTCATGCGCT GCGTGACATT T     31

( 2 ) INFORMATION FOR SEQ ID NO:81:

( i ) SEQUENCE CHARACTERISTICS:
        ( A ) LENGTH: 24 base pairs (B) TYPE: nucleic acid
(C) STRANDEDNESS: single
(D) TOPOLOGY: linear (xi) SEQUENCE DESCRIPTION: SEQ ID NO:81:

CTGAAATAGA ATTTCTATAT GTAG 24

(2) INFORMATION FOR SEQ ID NO:82:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:82:

GTGAGTATTT ATTGATACCT TATATGTAAT 30

(2) INFORMATION FOR SEQ ID NO:83:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:83:

CTTGATAGGC ATTTGAATTG TTTTTTTCAG 30

(2) INFORMATION FOR SEQ ID NO:84:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:84:

GTCTCTTAAG TAATAAATGT TTATTGAATA 30

(2) INFORMATION FOR SEQ ID NO:85:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:85:

ATTTACATTT TCTAATCCCT TTCTTTCTAG 30

(2) INFORMATION FOR SEQ ID NO:86:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:86:

GTAAGAAGAT TAATTAGTCT GATATAATTC 30

(2) INFORMATION FOR SEQ ID NO:87:

(i) SEQUENCE CHARACTERISTICS:
(A) LENGTH: 29 base pairs
(B) TYPE: nucleic acid
(C) STRANDEDNESS: single (D) TOPOLOGY: linear (x i) SEQUENCE DESCRIPTION: SEQ ID NO:87:

TATTGGGTGG ATTTGTTTGT ATATTCTAG 29

(2) INFORMATION FOR SEQ ID NO:88:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:88:

GTATTCTATT AAATTTTTAA CATTAATACT 30

(2) INFORMATION FOR SEQ ID NO:89:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:89:

GGACTGAGGG GAGATATTTT TGTTTGTCAG 30

(2) INFORMATION FOR SEQ ID NO:90:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:90:

GTAATGTAAT GAGTGTTGCT TCTTACGTTT 30

(2) INFORMATION FOR SEQ ID NO:91:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:91:

TGAATGACAT TATATCTCAT TTTTCTTTAG 30

(2) INFORMATION FOR SEQ ID NO:92:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:92:

GTAATGGAAT TTAGAATTTT TGGTTTTTAA 30

(2) INFORMATION FOR SEQ ID NO:93:

(i) SEQUENCE CHARACTERISTICS:
        (A) LENGTH: 30 base pairs
        (B) TYPE: nucleic acid
        (C) STRANDEDNESS: single
        (D) TOPOLOGY: linear ( x i ) SEQUENCE DESCRIPTION: SEQ ID NO:93:

CATTAAAAGA GGTGTTCTTG TGACAAACAG 30

( 2 ) INFORMATION FOR SEQ ID NO:94:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:94:

GTAAATATTA GAGGCTCTAT TATTTATGAC 30

( 2 ) INFORMATION FOR SEQ ID NO:95:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

CTTCAATTTT TGTTGTTTCC ATGTTTTCAG 30

( 2 ) INFORMATION FOR SEQ ID NO:96:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

GTAAATTGCA TTTTTCTAAA CAACGGTATA G 31

( 2 ) INFORMATION FOR SEQ ID NO:97:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:97:

CCCAAAGCTA TTTTCACAAT CTTTTCTTAT AG 32

( 2 ) INFORMATION FOR SEQ ID NO:98:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:98:

GTACATTTTT TCCCAGATTT GGTAAAGCCA 30

( 2 ) INFORMATION FOR SEQ ID NO:99:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

AACTTAAAAA CAACAATAAC TCCTGTTTAG 30

(2) INFORMATION FOR SEQ ID NO:100:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:100:

GTAAGAAATT TGACTTGATT TTTTTTTTTT 30

(2) INFORMATION FOR SEQ ID NO:101:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:101:

GTATATTTTT TTCTTTGACT TATCTCACAG 30

(2) INFORMATION FOR SEQ ID NO:102:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:102:

GTATTATGAA AAGACAAAGT TACTGTATTT T 31

(2) INFORMATION FOR SEQ ID NO:103:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:103:

TTTCAGAGTG TCTTTCTTTT TTGCTACTAG 30

(2) INFORMATION FOR SEQ ID NO:104:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:104:

GTATGTAATT CGTATGACTT GGTTATCCTA 30

(2) INFORMATION FOR SEQ ID NO:105:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:105:

CTTACATGAA CTCTATGTCG TGGCATTCAG 30

( 2 ) INFORMATION FOR SEQ ID NO:106:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

GTAAATACAA TTTAAAACTA TGTCATCTTA 30

( 2 ) INFORMATION FOR SEQ ID NO:107:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

ATTTATTCCC ATATGTCATT TTCATTTCAG 30

( 2 ) INFORMATION FOR SEQ ID NO:108:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

GTTTGTTTTT TTTATTGGCT GGATTAGTGT 30

( 2 ) INFORMATION FOR SEQ ID NO:109:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

TATATTTTAA GATTTGCCT TTCTTATACA G 31

( 2 ) INFORMATION FOR SEQ ID NO:110:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

GTAAGATTTT TGGAGCAACC CTTAAGATAG 30

( 2 ) INFORMATION FOR SEQ ID NO:111:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:111:

TATAATTTAA ATTGGTTGTG TTTTCTTGAA G 31

( 2 ) INFORMATION FOR SEQ ID NO:112:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:112:

GTAACTAGGT TTCTACAAGT GACAATTTTA      30

( 2 ) INFORMATION FOR SEQ ID NO:113:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:113:

TTGTGTTTTA CCTTAATTAT TCTATGCAAG      30

( 2 ) INFORMATION FOR SEQ ID NO:114:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:114:

GCAAGTGTTA CTCAGCCCAA TATTCTACCC      30

( 2 ) INFORMATION FOR SEQ ID NO:115:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:115:

CTTAATTTTG TGTCTTTTTT TTAATGGTAG      30

( 2 ) INFORMATION FOR SEQ ID NO:116:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:116:

GTAAGTAAAC CTGAAAATCA AACCACAATA      30

( 2 ) INFORMATION FOR SEQ ID NO:117:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:117:

GTATTTGGAT TAAACATACG TACCTTTTAG      30

( 2 ) INFORMATION FOR SEQ ID NO:118:

( i ) SEQUENCE CHARACTERISTICS:

(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:118:

GTATTTGGAT TAAACATACG TACCTTTTAG 30

(2) INFORMATION FOR SEQ ID NO:119:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:119:

TATGTAATGT TTTTGTTTT TTATTAATAG 30

(2) INFORMATION FOR SEQ ID NO:120:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:120:

GTATGTTTTT TTTAAAGAAG AAACGTTACT 30

(2) INFORMATION FOR SEQ ID NO:121:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:121:

TCACTAAAAT CTCTTCATTT TTAAATACAG 30

(2) INFORMATION FOR SEQ ID NO:122:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:122:

GTAATTTGCA ATTAACTCTT GATTTTTTT 30

(2) INFORMATION FOR SEQ ID NO:123:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:123:

CTATTATCAA TCATGTTTAT ACTTTTATTA G 31

(2) INFORMATION FOR SEQ ID NO:124:

(i) SEQUENCE CHARACTERISTICS:
(A) LENGTH: 30 base pairs
(B) TYPE: nucleic acid (C) STRANDEDNESS: single
(D) TOPOLOGY: linear (xi) SEQUENCE DESCRIPTION: SEQ ID NO:124:

GTGAGCCTTC CCTTCTCTGG CTTAGCCCTT 30

(2) INFORMATION FOR SEQ ID NO:125:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:125:

ACTTGTTTAT TCATGCTTAA TTATTCTGAA G 31

(2) INFORMATION FOR SEQ ID NO:126:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:126:

GTAACTATTT GTACTTCTGT TAGTTCACCA 30

(2) INFORMATION FOR SEQ ID NO:127:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:127:

AATTAAAAGG TATTTAATCT GTAACTCCAG 30

(2) INFORMATION FOR SEQ ID NO:128:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:128:

GTGAGTGACA CCCAAAATTA AAGGTTATTG 30

(2) INFORMATION FOR SEQ ID NO:129:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:129:

AAAATAATTA TATATATTCT CTATTTAAAG 30

(2) INFORMATION FOR SEQ ID NO:130:

(i) SEQUENCE CHARACTERISTICS:
(A) LENGTH: 30 base pairs
(B) TYPE: nucleic acid
(C) STRANDEDNESS: single
(D) TOPOLOGY: linear ( x i ) SEQUENCE DESCRIPTION: SEQ ID NO:130:

GTAATCTTCT TGTACATATA GTAGATTGAG    30

( 2 ) INFORMATION FOR SEQ ID NO:131:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

TTTCAGATTG TTTGTTTCTT TTTTCTCCAG    30

( 2 ) INFORMATION FOR SEQ ID NO:132:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

GTAAGTAATA AAATCTATGT ATCTATTCTT    30

( 2 ) INFORMATION FOR SEQ ID NO:133:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

CCTCCTAACT TCACTGTATT CTTTACTTTA G    31

( 2 ) INFORMATION FOR SEQ ID NO:134:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:134:

GTAAGTGATA TGAAGTAAAG GAGGGAAAT    29

( 2 ) INFORMATION FOR SEQ ID NO:135:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:135:

ATCCGTATTT ATAATGTGTT TTGACTCTAG    30

( 2 ) INFORMATION FOR SEQ ID NO:136:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

```
GTAAAGTATT  TTATAAGGAG  GACTTTATTT  T                                            3 1
```

( 2 ) INFORMATION FOR SEQ ID NO:137:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

```
AAGAACAGAT  GTTCTCTCTG  TTTAG                                                    2 5
```

( 2 ) INFORMATION FOR SEQ ID NO:138:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

```
GTGAGCAGTA  TTTAAGAAG  GTCCTGTTGT                                                3 0
```

( 2 ) INFORMATION FOR SEQ ID NO:139:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

```
ACTGGAACCT  TTGTGTTTTT  GTCCTTAG                                                 2 8
```